US012622940B2

(12) United States Patent
    Stamets

(10) Patent No.: US 12,622,940 B2
(45) Date of Patent: *May 12, 2026

(54) COMBINED FUNGAL COMPOSITION FOR MODULATING AN INFLAMMATORY RESPONSE

(71) Applicant: TURTLE BEAR HOLDINGS, LLC, Shelton, WA (US)

(72) Inventor: Paul E. Stamets, Shelton, WA (US)

(73) Assignee: TURTLE BEAR HOLDINGS, LLC, Shelton, WA (US)

( * ) Notice: Subject to any disclaimer, the term of this patent is extended or adjusted under 35 U.S.C. 154(b) by 271 days.

This patent is subject to a terminal disclaimer.

(21) Appl. No.: 18/446,315

(22) Filed: Aug. 8, 2023

(65) Prior Publication Data

US 2023/0414687 A1    Dec. 28, 2023

Related U.S. Application Data

(62) Division of application No. 17/221,411, filed on Apr. 2, 2021, now Pat. No. 11,779,620.

(60) Provisional application No. 63/029,815, filed on May 26, 2020, provisional application No. 63/004,788, filed on Apr. 3, 2020.

(51) Int. Cl.

| | |
|---|---|
| *A61K 36/074* | (2006.01) |
| *A61K 31/716* | (2006.01) |
| *A61K 36/07* | (2006.01) |
| *A61K 45/06* | (2006.01) |
| *A61K 47/02* | (2006.01) |
| *A61K 47/10* | (2017.01) |
| *A61P 31/12* | (2006.01) |
| *A61P 37/06* | (2006.01) |

(52) U.S. Cl.

CPC .......... *A61K 36/074* (2013.01); *A61K 31/716* (2013.01); *A61K 36/07* (2013.01); *A61K 45/06* (2013.01); *A61K 47/02* (2013.01); *A61K 47/10* (2013.01); *A61P 31/12* (2018.01); *A61P 37/06* (2018.01)

(58) Field of Classification Search

CPC .................................................. A61K 36/074

See application file for complete search history.

(56) References Cited

U.S. PATENT DOCUMENTS

| | | | |
|---|---|---|---|
| 7,790,175 | B2 | 9/2010 | Eguchi et al. |
| 11,730,784 | B2 | 8/2023 | Stamets |
| 11,779,620 | B2 | 10/2023 | Stamets |
| 2009/0130138 | A1 | 5/2009 | Stamets et al. |
| 2010/0047269 | A1 | 2/2010 | Eguchi et al. |
| 2011/0189220 | A1 | 8/2011 | Yang et al. |
| 2012/0294897 | A1 | 11/2012 | Fiorentino Gomez et al. |
| 2014/0105928 | A1 | 4/2014 | Stamets et al. |
| 2014/0364499 | A1 | 12/2014 | Lau et al. |
| 2020/0023024 | A1 | 1/2020 | Jin |
| 2021/0308200 | A1 | 10/2021 | Stamets |
| 2021/0308201 | A1 | 10/2021 | Stamets |

FOREIGN PATENT DOCUMENTS

| | | |
|---|---|---|
| CN | 102792851 A | 11/2012 |
| WO | 2016161138 A1 | 10/2016 |
| WO | 2020014745 A1 | 1/2020 |

OTHER PUBLICATIONS

Australian Patent Office. Examination Report No. 1 for Application No. 2021246099, dated Feb. 28, 2025 (3 pages).

Australian Patent Office. Examination Report No. 1 for Application No. 2021246519, dated Feb. 28, 2025 (3 pages).

Ascherl et al., "Infection With Human Immunodeficiency Virus-1 Increases Expression of Vascular Endothelial Cell Growth Factor in T Cels: Implications for Acquired Immunodeficiency Syndrome-Assicated Vasculopathy", Blood, vol. 93, No. 12, 1999, pp. 4323-4241.

Bachstetter et al., "The p38 MAP Kinase Family as Regulators of Proinflammatory Cytokine Production in Degenerative Diseases of CNS", Aging and Disease, vol. 1, No. 3, 2010, pp. 199-211.

Baig et al., "Evidence of the COVID-19 Virus Targeting the CNS: Tissue Distribution, Host-Virus Interaction, and Proposed Neurotropic Mechanisms", ACS Chemical Neuroscience, vol. 11, 2020, pp. 995-998.

Benson et al., "The mycelium of the Trametes versicolor (Turkey tail) mushroom and its fermented substrate each show potent and complementary immune activating properties in vitro", BMC Complementary and Alternative Medicine, vol. 19, 2019, 14 pages.

Chen et al., "Measuring IL-6 and sIL-6R in serum from patients treated with tocilizumb and/or siltuximab following Car T cell therapy", J. Immunol. Meth., vol. 434, 2016, pp. 1-8.

Choi et al., "Antithrombotic and Antiplatelet Effects of Cordyceps militaris", Mycobiology, 2020, 5 pages.

Davis et al., "Differential Immune Activating, Anti-Inflammatory, and Regenerative Properties of the Aqueous, Ethanol, and Solid Fractions of a Medicinal Mushroom Blend", Journal of Inflammation Research, vol. 13, 2020, pp. 117-131.

De Lemos et al., "Neuroprotective Effects of the Absence of JNK1 or JNK3 Isoforms on Kainic Acid-Induced Temporal Lobe Epilepsy-Like Symptoms", Molecular Neurobiology, vol. 55, No. 5, 2018, pp. 4437-4452.

D'Elia et al., "Targeting the "Cytokine Storm" for Therapeutic Benefit", Clinical and Vaccine Immunology, vol. 20, No. 3, 2013, pp. 319-327.

Diao et al., "Reduction and Functional Exhaustion of T Cells In Patients with Coronavirus Disease", Frontiers in Immunology, vol. 11, 2020, pp. 1-8.

Fabian et al., "A small molecule-kinase interaction map for clinical kinase inhibitors", Nature Biotechnology, vol. 23, No. 3, 2005, pp. 329-336.

(Continued)

*Primary Examiner* — Terry A McKelvey
*Assistant Examiner* — Jacob A Boeckelman
(74) *Attorney, Agent, or Firm* — Michael Best & Friedrich LLP

(57) ABSTRACT

Described herein are combined fungal compositions for treating, prophylaxis of, or ameliorating symptoms of one or more adverse reactions triggered by an infectious disease or condition that causes an inflammatory response. In one aspect the composition comprises an aqueous or solid fraction of *Trametes versicolor* and *Fomitopsis officinalis* mycelium, fermented substrates thereof, or combinations thereof.

19 Claims, 29 Drawing Sheets

(56) References Cited

OTHER PUBLICATIONS

Gibbons et al., "Random Regression Models: A Comprehensive Approach to the Analysis of Longitudinal Psychiatric Data", Psychopharmacology Bulletin, vol. 24, No. 3, 1988, pp. 438-443.

Heagerty et al., "Time-Dependent ROC Curves for Censored Survival Data and a Diagnostic Marker", Biometrics, vol. 56, 2000, pp. 337-344.

Hedeker et al., "Random Regression Models for Multicenter Clinical Trials Data", Psychopharmacology Bulletin, vol. 27, No. 1, 1991, pp. 73-77.

International Search Report and Written Opinion for Application No. PCT/US21/25553 dated Aug. 6, 2021 (19 pages).

International Search Report and Written Opinion for Application No. PCT/US21/25564 dated Sep. 27, 2021 (18 pages).

Laird et al., "Random-Effects Models for Longitudinal Data", Biometrics, vol. 38, No. 4, 1982, pp. 963-974.

Liang et al., "The activation of BDNF reduced inflammation in a spinal cord injury model by TrkB/p38 MARK signaling", Experimental and Therapeutic Medicine, vol. 17, 2019, pp. 1688-1696.

Pleszczynska et al., "Fomitopsis betulina (formerly Piptoporus betulinus): the Iceman's polypore fungus with modern biotechnological potential", World J Microbiol Biotechnol, vol. 33, No. 83, 2017, 12 pages.

Prencipe et al., "Nerve Growth Factor Downregulates Inflammatory Response in Human Monocytes through TrkA", Journal of Immunology, vol. 192, No. 7, 2014, pp. 3345-3354.

Redondo-Castro et al., "Interleukin-1 primes human mesenchymal stem cells towards an anti-inflammatory and pro-trophic phenotype in vitro", Stem Cell Res. Ther., vol. 8, 2017, pp. 1-11.

Savory et al., "Viral Vascular Endothelial Growth Factor Plays a Critical Role in Orf Virus Infections", Journal of Virology, vol. 74, No. 20, 2000, p. 10699-10706.

Thevarajan et al., "Breadth of concomitant immune responses prior to patient recovery: ac ase report of non-severe COVID-19", Nature Medicine, vol. 26, 2020, pp. 453-456.

Torkelson et al., "Phase 1 Clinical Trial of Trametes versicolor in Women with Breast Cancer", ISRN Oncology, 2012, pp. 1-7.

Velazquez-Salinas et al., "The Role of Interleukin 6 During Viral Infections", Frontiers in Microbiology, vol. 10, No. 1067, 2019, pp. 1-6.

Zheng et al., "Functional exhaustion of antiviral lymphocytes in COVID-19 patients", Cellular & Molecular Immunology, 2020, 3 pages.

European Search Report for Application No. 21782406.9, dated May 6, 2024 (11 pages).

European Search Report for Application No. 21779226.6, dated Mar. 1, 2024 (16 pages).

Hsieh, T.-C., et al. "Effects of extracts of Coriolus versicolor (I'm-Yunity™) on cell-cycle progression and expression of interleukins-13,-6, and-8 in Promyelocytic HL-60 leukemic cells and mitogenically stimulated and nonstimulated human lymphocytes." The Journal of Alternative & Complementary Medicine 8.5 (2002): 591-602.

Ho, C. Y., et al. "Differential effect of Coriolus versicolor (Yunzhi) extract on cytokine production by murine lymphocytes in vitro." International immunopharmacology 4.12 (2004): 1549-1557.

Canada Patent Office Action for Application No. 3173635 dated Feb. 20, 2026 (8 pages).

| Initial substrate (Rice flour) | | Turkey Tail spawn |

Turkey Tail mycelium growing on substrate

| Initial substrate (Control) | Fermented substrate | Turkey Tail mycelium |

INF-γ induction by aqueous fractions

INF-γ induction by solid fractions

FIG. 9

CD3- CD56+ NK cells

CD3+ CD56+ NKT cells

Lymphocytes

Monocytes

CD3- CD56- Non-T Non-NK lymphocytes

CD3+ CD56- T cells

COMBINED FUNGAL COMPOSITION FOR MODULATING AN INFLAMMATORY RESPONSE

CROSS-REFERENCE TO RELATED APPLICATIONS

This application is a divisional of U.S. patent application Ser. No. 17/221,411, filed Apr. 2, 2021, which claims priority to U.S. Provisional Patent Application No. 63/004, 788, filed on Apr. 3, 2020 and U.S. Provisional Patent Application No. 63/029,815, filed on May 26, 2020, each of which are incorporated by reference herein in its entirety.

TECHNICAL FIELD

Described herein are mushroom compositions and methods for treating, prophylaxis of, or ameliorating symptoms of one or more adverse reactions triggered by an infectious disease or condition that increases an anti-inflammatory response in a subject with such compositions. In one aspect the composition comprises an aqueous or solid fraction of a mycelium, a fermented substrate thereof, or a combination thereof optionally combined with one or more buffering agents, ethanol, and water.

BACKGROUND

Mushrooms have been embraced for centuries due to their nutritional and medicinal properties. They have been historically used in the treatment of infectious disease, gastrointestinal disorders and asthmatic conditions, as well as to support overall wellbeing. Fungi now occupy their own kingdom, but they were once considered plants due to their resemblance and root-like structures. One of many characteristics that separate fungal from plant organisms is the cell wall structure. The cell walls of fungi contain chitin, a modified form of the polysaccharide cellulose. Chitin is comprised of $\beta$-(1→4)-linked N-acetylglucosamine monomers, whereas cellulose is comprised of $\beta$-(1→4)-linked glucose units. Chitin degrades into a mixture of shorter-chained polysaccharides along with monosaccharide products. This degradation can occur with a variety of processing techniques that implement heat and drying.

Contemporary research has mainly focused on the broad immune activity of mushrooms. Mushroom polysaccharides possess documented immunomodulatory properties, specifically through the activation of natural killer cells, macrophages, and neutrophils, as well as induction of innate immune cytokines and interleukins. $\beta$-glucans, proteoglycans, and heteroglucans are classes of polymers present in the cell walls of fungi. The generic term $\beta$-glucan refers to the polymeric form of glucose residues connected by $\beta$-(1→3), $\beta$-(1→4), and $\beta$-(1→6)-linkages. The type of $\beta$-glucans isolated from fungi consist mainly of a linear backbone of $\beta$-(1→3) glucose monomers and side branches comprised of $\beta$-(1→3) and $\beta$-(1→6)-linked oligosaccharides.

The most widely studied $\beta$-glucans are comprised of (1→3)-$\beta$, and (1,6)-$\beta$ linkages, which exhibit immunostimulatory and antitumor properties. These polysaccharides are ligands for the dectin-1 and toll-like receptor 2 (TLR-2) receptor systems expressed on macrophages and dendritic cells, inducing NK cells, neutrophils, T-cells, B-cells, as well as TNF-a, IL-4, and IL-6 signaling. The Complement Receptor-3 (CD11b/CD18) in context of extracellular matrix is also involved in immune responses to fungal $\beta$-glucans.

2

While the immune activating, pro-inflammatory properties of fungal water-insoluble $\beta$-glucans are well documented, the immune modulating effects of fungal non-$\beta$-glucan-fractions are less recognized.

While prior research on medicinal mushrooms has primarily focused on the solid, $\beta$-glucan-rich fraction, and $\beta$-glucan mediated responses are clearly important, focusing on this compound class in isolation clearly does not reflect the overall bioactivity of a complex blend when consumed for immune support. Emerging evidence suggests that a blend of mushrooms may provide additive or synergistic effects on the host immune response.

SUMMARY

One embodiment described herein is a composition for treating, prophylaxis of, or ameliorating symptoms of one or more adverse reactions triggered by an infectious disease or condition that increases an anti-inflammatory response in a subject, the composition comprising:

an aqueous or solid fraction of a mushroom mycelium and/or fruit body mixture; one or more buffering agents; ethanol; and water. In one aspect, the aqueous or solid fraction comprises beta-glucans. In another aspect, the buffering agent comprises phosphate buffered saline. In another aspect, the composition comprises an aqueous or solid fraction of *Trametes versicolor* mycelium. In another aspect, the composition comprises about 200 mg to about 10 g of *Trametes versicolor* mycelium. In another aspect, the composition further comprises one or more preservatives, flavorings, colorings, stabilizers, emulsifiers, or other pharmaceutically acceptable excipients. In another aspect, the infectious disease or condition increases expression of growth factors. In another aspect, the growth factors comprise one or more of basic fibroblast growth factor, or vascular endothelial growth factor. In another aspect, the mushroom mycelium and/or fruit body mixture comprises one or more of *Agaricus brasiliensis* f. *blazei*, *Cordyceps militaris*, *Flammulina velutipes*, *Fomes fomentarius*, *Fomitopsis officinalis*, *Ganoderma applanatum*, *Ganoderma lucidum* s.l., *Ganoderma oregonense* s.l., *Grifola frondosa*, *Hericium erinaceus*, *Inonotus obliquus*, *Lentinula edodes*, *Phellinus linteus*, *Piptoporus betulinus*, *Pleurotus ostreatus*, *Schizophyllum commune*, or *Trametes versicolor*.

Another embodiment described herein is a composition for treating, prophylaxis of, or ameliorating symptoms of one or more adverse reactions triggered by an infectious disease or condition that increases an anti-inflammatory response in a subject, the composition comprising: an aqueous or solid fraction of *Trametes versicolor* mycelium, a fermented substrate thereof, or a combination thereof; one or more buffering agents; ethanol; and water. In one aspect, the aqueous or solid fraction comprises beta-glucans. In another aspect, the buffering agent comprises phosphate buffered saline. In another aspect, the infectious disease or condition increases expression of growth factors. In another aspect, the growth factors comprise one or more of basic fibroblast growth factor or vascular endothelial growth factor. In another aspect, the composition comprises about 200 mg to about 10 g of *Trametes versicolor* mycelium. In another aspect, the infectious disease comprises a bacterial infection. In another aspect, the bacterial infection comprises one or more of *Streptococcus pneumoniae*, *Mycobacterium tuberculosis*, *Bordetella pertussis*, *Haemophilus influenzae*, *Moraxella catarrhalis*, *Pseudomonas aeruginosa*, *Stenotrophomonas maltophila*, *Staphylococcus aureus*, *Streptococcus pyogenes*, *Neisseria meningitidis*, *Klebsiella pneumo-*

*niae*, or Non-tuberculosis *Mycobacterium*. In another aspect, the infectious disease comprises a viral infection. In another aspect, the viral infection comprises one or more of Paramyxoviridae (respiratory syncytial virus (RSV), parainfluenza virus (PIV), metapneumovirus (MPV), enteroviruses), Picornaviridae (Rhinovirus, RV), Coronaviridae (CoV), Adenoviridae (Adenovirus), Parvoviridae (HBoV), Orthomyxoviridae (influenza A, B, C, D, Isavirus, Thogotovirus, Quaranjavirus), or Herpesviridae (human herpes viruses, *Varicella zoster* virus, Epstein-Barr virus, cytomegalovirus). In another aspect, the CoV comprises one or more of Severe Acute Respiratory Syndrome (SARS-CoV), Middle East Respiratory Syndrome (MERS-CoV), COVID-19 (2019-nCoV, SARS-CoV-2), 229E, NL63, OC43, or HKU1.

Another embodiment described herein is a composition comprising an aqueous, hydroethanolic, or ethanolic extract of *Trametes versicolor* mycelium.

Another embodiment described herein is a use of a composition as described herein for modulating an inflammatory response comprising administering an effective amount of the composition to a subject in need thereof. In one aspect, the inflammatory response comprises release of anti-inflammatory and pro-inflammatory cytokines. In another aspect, the pro-inflammatory cytokines comprise one or more of interleukin-1β, interleukin-2, interleukin-4, interleukin-5, interleukin-6, interleukin-7, interleukin-8, interleukin-9, interleukin-12p70, interleukin-13, interleukin-15, interleukin-17A, tumor necrosis factor-α, interferon-γ, monocyte chemoattractant protein 1, eotaxin, interferon gamma-induced protein 10, granulocyte colony-stimulating factor, macrophage inflammatory protein 1α, macrophage inflammatory protein 1β, or RANTES. In another aspect, the anti-inflammatory cytokines comprise one or more of interleukin-1 receptor antagonist, interleukin-2, interleukin-4, interleukin-7, interleukin-9 interleukin-10, or interleukin-15.

Another embodiment described herein is a means for modulating an inflammatory response comprising administering to a subject in need thereof an effective amount of a composition described herein. In one embodiment, the inflammatory response comprises release of anti-inflammatory and pro-inflammatory cytokines.

Another embodiment described herein is a method for treating, prophylaxis of, or ameliorating symptoms of an infectious disease comprising: administering to a subject in need thereof an effective amount of a composition comprising: an aqueous or solid fraction of a mycelium, a fermented substrate thereof, or a combination thereof; one or more buffering agents; ethanol; and water. In one aspect, the mycelium comprises one or more of *Agaricus brasiliensis* f. *blazei, Cordyceps militaris, Flammulina velutipes, Fomes fomentarius, Fomitopsis officinalis, Ganoderma applanatum, Ganoderma lucidum* s.l., *Ganoderma oregonense* s.l., *Grifola frondosa, Hericium erinaceus, Inonotus obliquus, Lentinula edodes, Phellinus linteus, Piptoporus betulinus, Pleurotus ostreatus, Schizophyllum commune*, or *Trametes versicolor*. In another aspect, the mycelium is *Trametes versicolor* mycelium. In another aspect, the composition comprises about 200 mg to about 10 g of *Trametes versicolor* mycelium. In another aspect, the aqueous or solid fraction comprises beta-glucans. In another aspect, the composition comprises an aqueous or solid fraction of *Trametes versicolor* mycelium. In another aspect, the composition further comprises one or more preservatives, flavorings, colorings, stabilizers, emulsifiers, or other pharmaceutically acceptable excipients. In another aspect, the infectious disease comprises one or more symptoms comprising shortness of breath, wheezing, coughing, yellow mucus, green mucus, blood-tinged mucus, chest pain, breathlessness, rapid breathing, hypoxia, inflammation of the lung tissue, rapid heart rate, or increased blood pressure, or decreased blood pressure. In another aspect, the infectious disease comprises a bacterial infection. In another aspect, the bacterial infection comprises one or more of *Streptococcus pneumoniae, Mycobacterium tuberculosis, Bordetella pertussis, Haemophilus influenzae, Moraxella catarrhalis, Pseudomonas aeruginosa, Stenotrophomonas maltophila, Staphylococcus aureus, Streptococcus pyogenes, Neisseria meningitidis, Klebsiella pneumoniae*, or Non-tuberculosis *Mycobacterium*. In another aspect, the infectious disease comprises a viral infection. In another aspect, the viral infection comprises one or more of Paramyxoviridae (respiratory syncytial virus (RSV), parainfluenza virus (PIV), metapneumovirus (MPV), enteroviruses), Picornaviridae (Rhinovirus, RV), Coronaviridae (CoV), Adenoviridae (Adenovirus), Parvoviridae (HBoV), Orthomyxoviridae (influenza A, B, C, D, Isavirus, Thogotovirus, Quaranjavirus), or Herpesviridae (human herpes viruses, *Varicella zoster* virus, Epstein-Barr virus, cytomegalovirus). In another aspect, the CoV comprises one or more of Severe Acute Respiratory Syndrome (SARS-CoV), Middle East Respiratory Syndrome (MERS-CoV), COVID-19 (2019-nCoV, SARS-CoV-2), 229E, NL63, OC43, or HKU1.

Another embodiment described herein is a method for treating, prophylaxis of, or ameliorating symptoms of a bacterial or viral infection comprising administering an effective amount of an aqueous or solid extract of *Trametes versicolor*.

Another embodiment described herein is a method for modulating an inflammatory response associated with a bacterial or viral infection comprising administering an effective amount of an aqueous or solid extract of *Trametes versicolor*.

Another embodiment described herein is a method of manufacturing a composition as described herein, the method comprising: growing a mushroom on a substrate; and, separating the mushroom mycelium from a fruitbody and the substrate. In one aspect, the method further comprises incubating the mycelium with a solvent, forming a solution; extracting an aqueous fraction from the solution; and extracting a solid fraction from the solution. In another aspect, the method further comprises freeze-drying the mycelium; and grinding the dried mycelium into a powder. In another aspect, a pressure of about 1,500 mbar to about 2,000 mbar is applied to the mycelium during freeze-drying. In another aspect, a temperature of about 75° C. to 95° C. is applied to the mycelium. In another aspect, the substrate comprises one or more of rice, oat, straw, or sawdust. In another aspect, the mushroom is grown on a substrate at about 15° C. to about 30° C. for about 20 to about 120 days. In another aspect, the mushroom is grown on a substrate at about 20° C. to about 25° C. for about 40 days. In another aspect, the solvent is cold water.

Another embodiment described herein is a method for manufacturing a composition as described herein, the method comprising: incubating a powder of the mushroom mycelium and/or fruit body mixture in a solvent, forming a solution; extracting aqueous compounds from the solution in a buffered solution; extracting non-aqueous compounds from the solution in an ethanol solution; and extracting a solid fraction from the solution. In one aspect, the buffered solution comprises phosphate buffered saline. In another aspect, the ethanol solution comprises about 95% ethanol. In another aspect, the solid fraction comprises insoluble fractions of the powder of the mushroom mycelium and/or fruit body mixture.

Another embodiment described herein is a method for treating or lessening the severity of any type of pain in a subject in need thereof comprising: administering to the subject an effective amount of a composition comprising: an aqueous or solid fraction of a mycelium, a fermented substrate thereof, or a combination thereof; one or more buffering agents; ethanol; and water. In one aspect, the mycelium comprises one or more of *Agaricus brasiliensis* f. *blazei, Cordyceps militaris, Flammulina velutipes, Fomes fomentarius, Fomitopsis officinalis, Ganoderma applanatum, Ganoderma lucidum* s.l., *Ganoderma oregonense* s.l., *Grifola frondosa, Hericium erinaceus, Inonotus obliquus, Lentinula edodes, Phellinus linteus, Piptoporus betulinus, Pleurotus ostreatus, Schizophyllum commune*, or *Trametes versicolor*. In another aspect, the mycelium is *Trametes versicolor* mycelium. In another aspect, the composition comprises about 200 mg to about 10 g of *Trametes versicolor* mycelium. In another aspect, the aqueous or solid fraction comprises beta-glucans. In another aspect, the composition comprises an aqueous or solid fraction of *Trametes versicolor* mycelium. In another aspect, the composition further comprises one or more preservatives, flavorings, colorings, stabilizers, emulsifiers, or other pharmaceutically acceptable excipients. In another aspect, the pain comprises one or more types of neuropathic pain, somatic pain, visceral pain, and other types of pain as described herein.

Another embodiment described herein is a method for enhancing a viral therapy comprising: administering to a subject an effective amount of a composition comprising: an aqueous or solid fraction of a mycelium, a fermented substrate thereof, or a combination thereof; one or more buffering agents; ethanol; and water. In one aspect, the viral therapy comprises a vaccine, an antiviral drug, or a combination thereof. In another aspect, the mycelium comprises one or more of *Agaricus brasiliensis* f. *blazei, Cordyceps militaris, Flammulina velutipes, Fomes fomentarius, Fomitopsis officinalis, Ganoderma applanatum, Ganoderma lucidum* s.l., *Ganoderma oregonense* s.l., *Grifola frondosa, Hericium erinaceus, Inonotus obliquus, Lentinula edodes, Phellinus linteus, Piptoporus betulinus, Pleurotus ostreatus, Schizophyllum commune*, or *Trametes versicolor*. In another aspect, the mycelium is *Trametes versicolor* mycelium. In another aspect, the composition comprises about 200 mg to about 10 g of *Trametes versicolor* mycelium.

DESCRIPTION OF THE DRAWINGS

FIG. 2A is a diagram showing the origin of the three test products compared:

Initial substrate (rice flour), fermented substrate, and Tv mycelium. FIG. 2B is a photo of the three powders: Initial substrate (left) is plain rice flour prior to use as a substrate for growing the Tv mycelium. The fermented substrate (center) is the dried residual powder where the mycelium has been removed. The mycelium (right) is the collection of fungal hyphae, removed from the fermented substrate on which it was grown.

FIG. 9 shows the production of test fractions. The medicinal mushroom blend was supplied as a powder, and suspended in PBS at a concentration of 100 g/L. The aqueous extraction was performed over 1 hour at ambient temperature under constant agitation. The post-aqueous solid fraction was extracted using ethanol under similar conditions. Both the aqueous and post-aqueous ethanol extracts were filtered through 0.22-micron cellulose acetate filters before adding to bioassays. The remaining post-extraction solids were homogenized but not filtered prior to testing in bioassays.

FIG. 14A shows IL-1β: 772±28 pg/mL; FIG. 14B shows TNF-α: 7,073±185 pg/mL.

US 12,622,940 B2

Figure 15A:
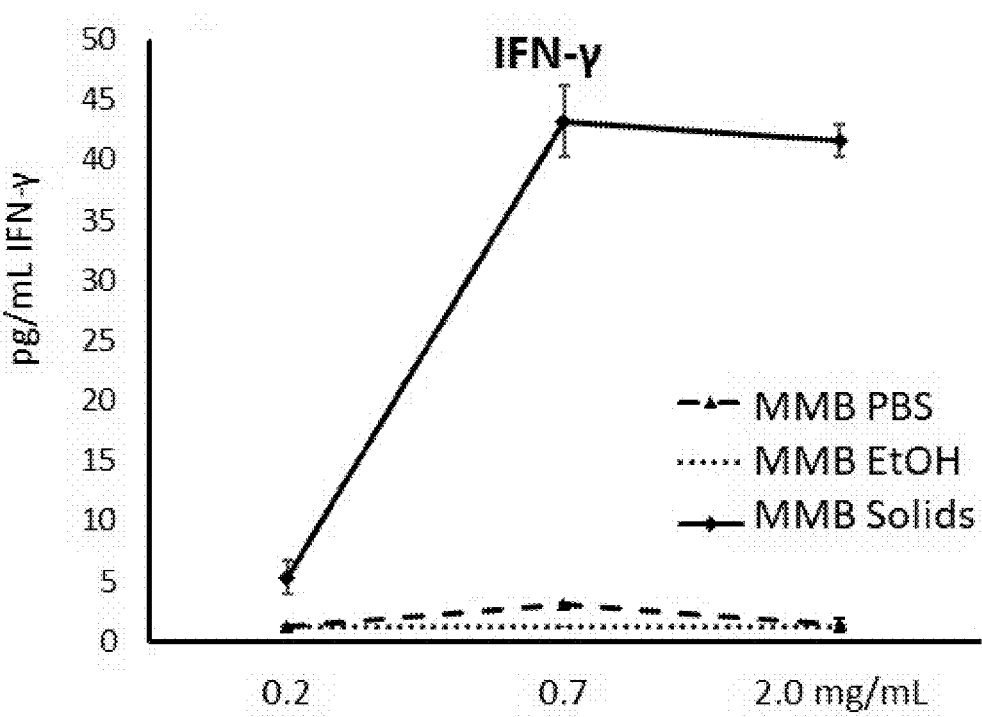
FIG. 15A-D show changes in anti-viral cytokine levels in human PBMC cultures. Changes in cytokine levels in human PBMC cultures treated for 24 hours with serial dilutions of MMB aqueous extract in PBS (MMB PBS), MMB post-aqueous ethanol extract (MMB EtOH), and the solid fraction (MMB solids). Data are presented as picogram per milliliter (pg/mL) based on the mean±standard deviation from triplicate cultures and represents one of three experiments using PBMC from three different healthy human
Figure 15B:
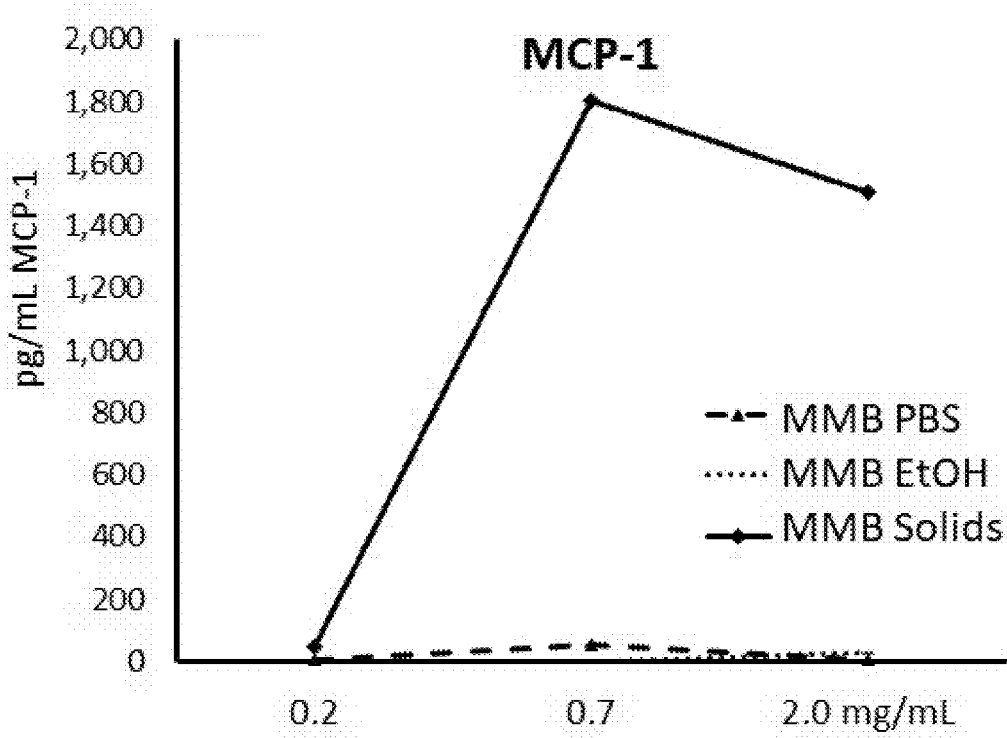
Figure 15C:
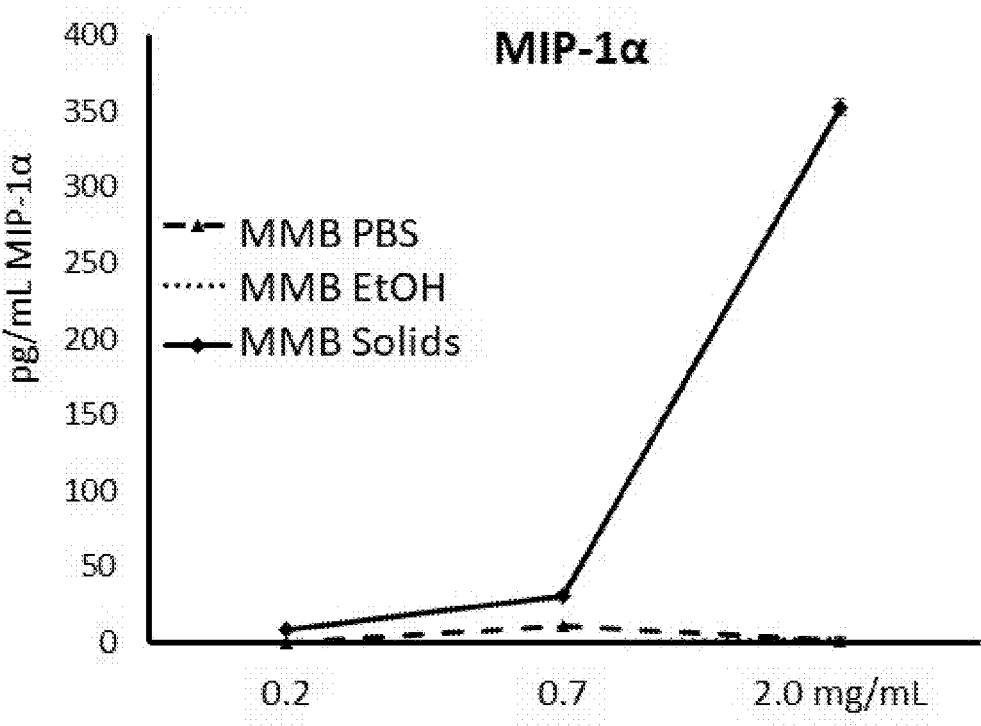
Figure 15D:
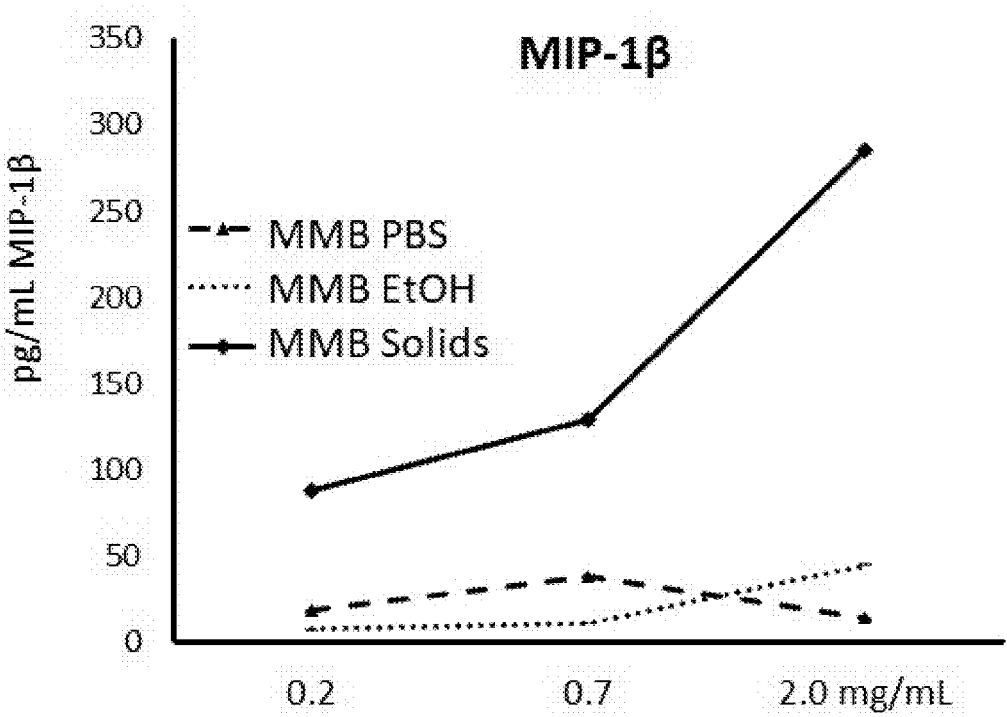

9
10 donors. Cytokine levels for LPS-treated control cultures were as follows: FIG. 15A shows IFN-γ: 71±2 pg/mL; FIG. 15B shows MCP-1: 2,052±35 pg/mL; FIG. 15C shows MIP-1α: 2,116±0 pg/mL; FIG. 15D shows MIP-1β: 6,497±814 pg/mL.

Figures 16A, 16B:
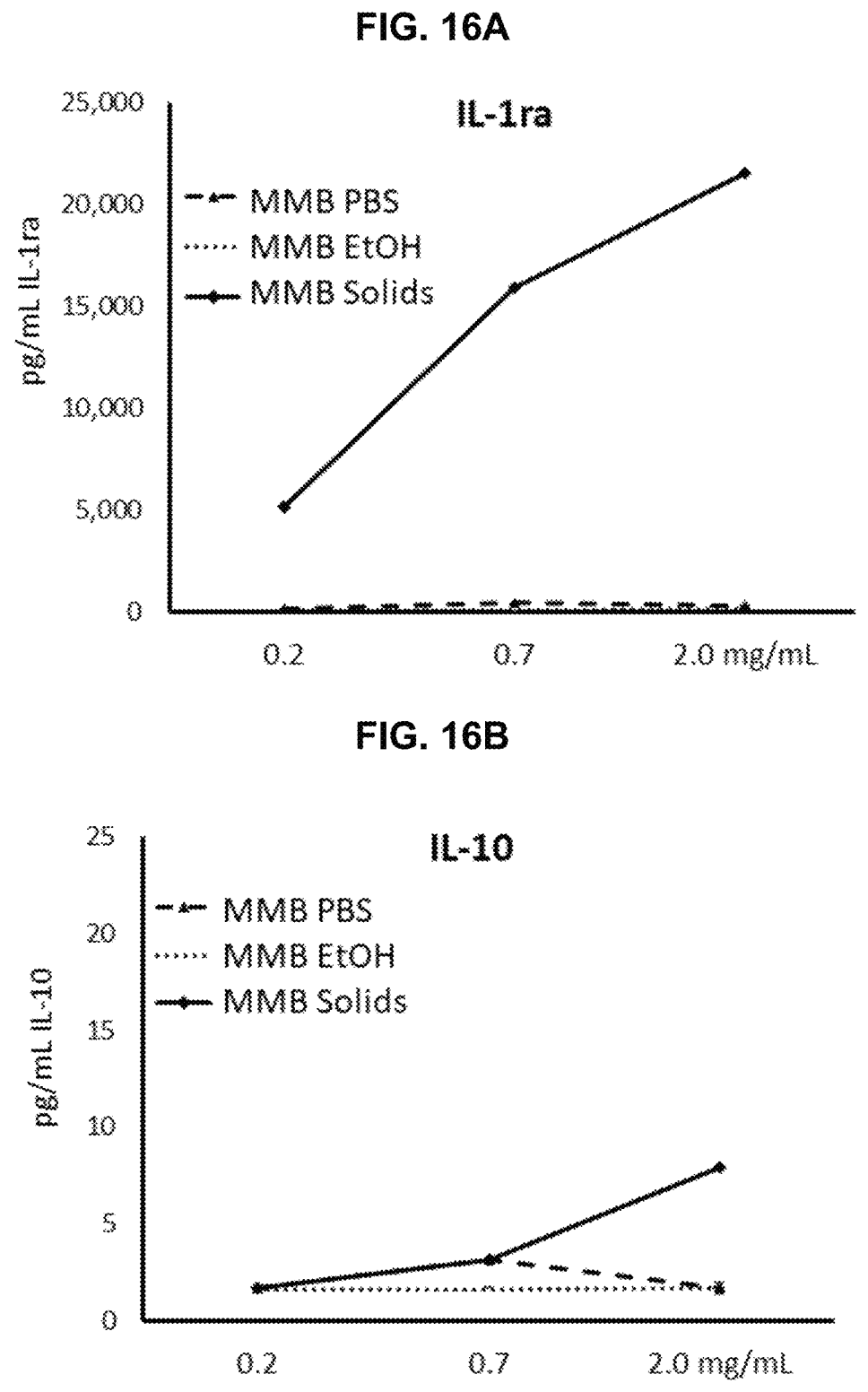

FIG. 16A and FIG. 16B show changes in anti-inflammatory cytokines. Changes in cytokine levels in human PBMC cultures treated for 24 hours with serial dilutions of MMB aqueous extract in PBS (MMB PBS), MMB post-aqueous ethanol extract (MMB EtOH), and the solid fraction (MMB Solids). Data are presented as picogram per milliliter (pg/mL) based on the mean±standard deviation from triplicate cultures and represents one of three experiments using PBMC from three different healthy human donors. Note the 1000-fold difference in the scales on the Y-axes. Cytokine levels for LPS-treated control cultures were as follows: FIG. 16A shows IL-1ra: 8,134±473 pg/mL; FIG. 16B shows IL-10: 301±15 pg/mL.

Figure 17A:
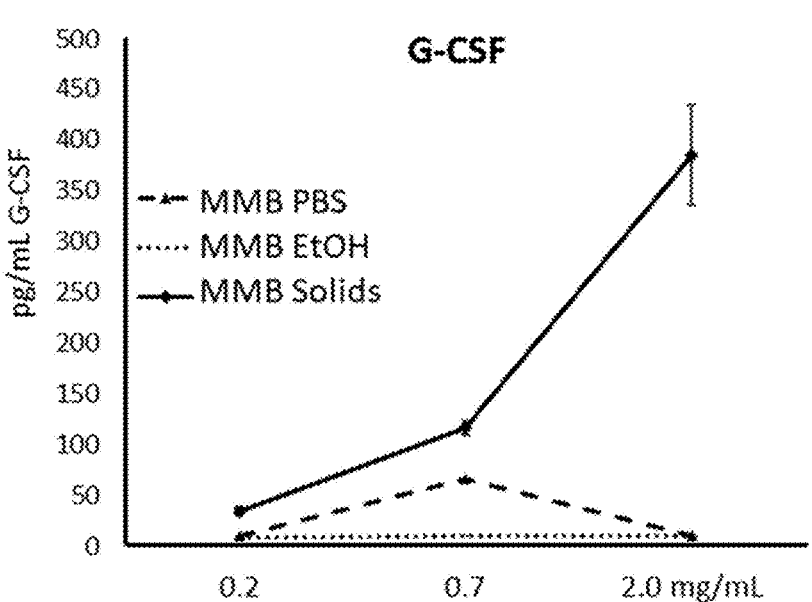
Figure 17B:
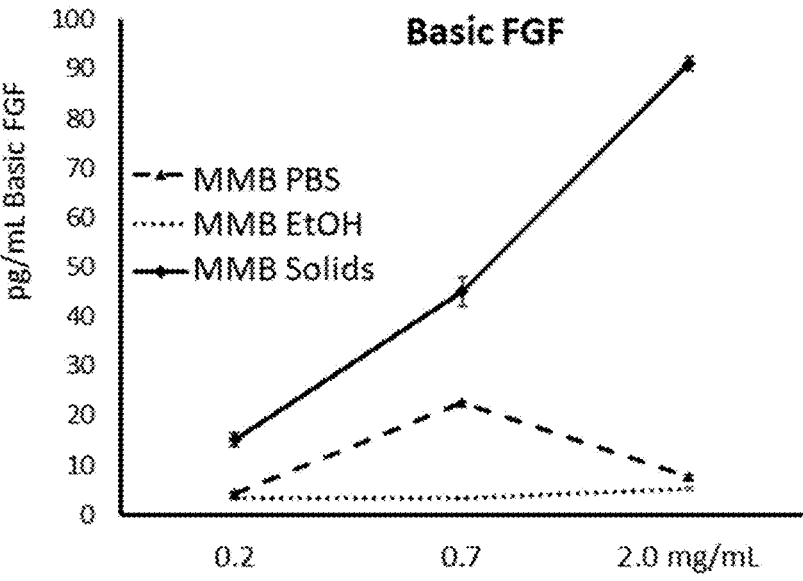
Figure 17C:
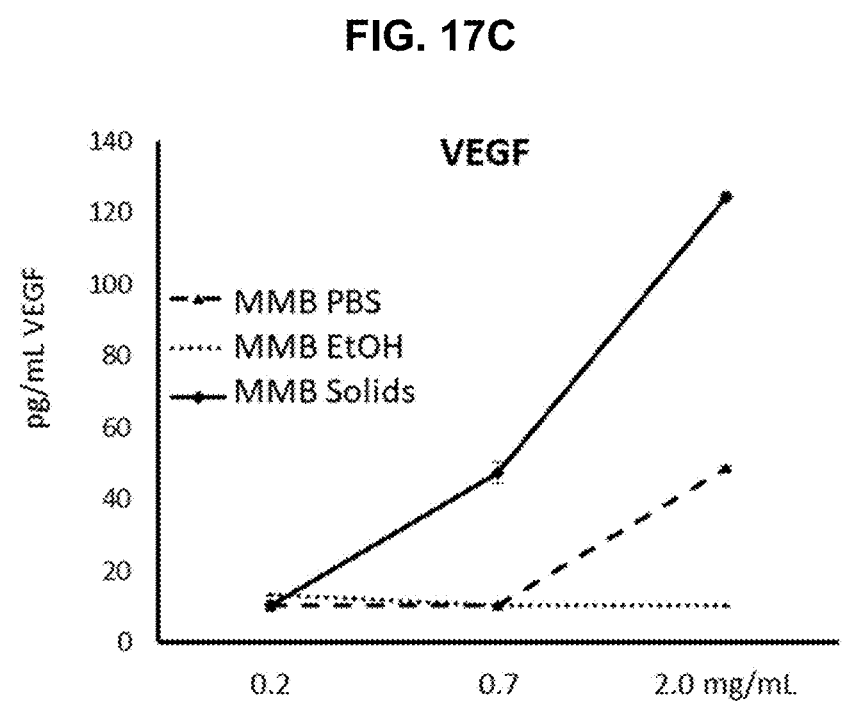

FIG. 17A-C show changes in cytokines with effects on regenerative functions. Changes in cytokine levels in human PBMC cultures treated for 24 hours with serial dilutions of MMB aqueous extract in PBS (MMB PBS), MMB post-aqueous ethanol extract (MMB EtOH), and the solid fraction (MMB Solids). Data are presented as picogram per milliliter (pg/mL) based on the mean±standard deviation from triplicate cultures and represents one of three experiments using PBMC from three different healthy human donors. Cytokine levels for LPS-treated control cultures were as follows: FIG. 17A shows G-CSF: 1,458±58 pg/mL; FIG. 17B shows bFGF: 221±8 pg/mL; FIG. 17C shows VEGF: 421±17 pg/mL.

Figure 18:
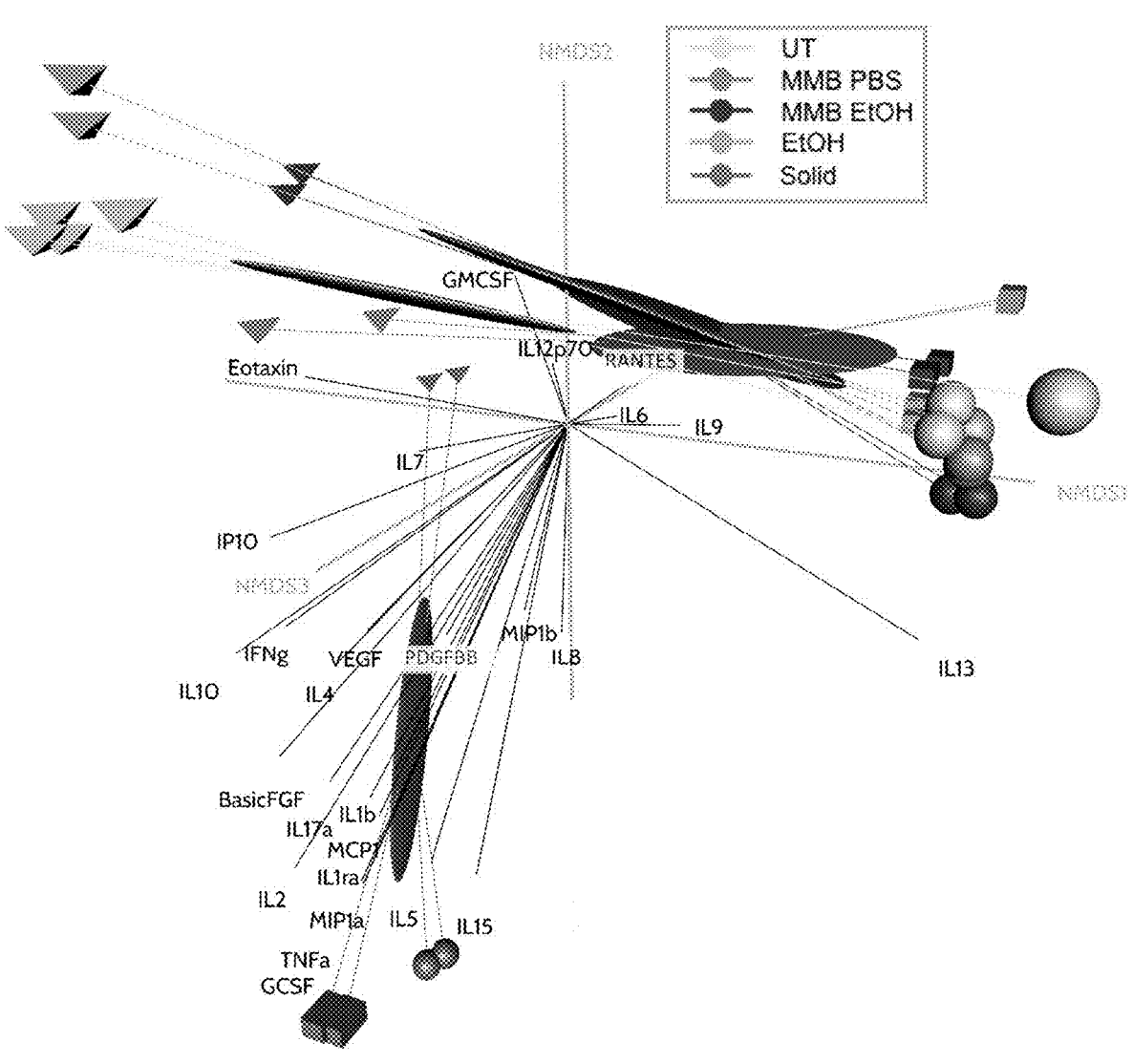

FIG. 18 shows NMDS ordination plot of changes to cytokine and growth factor expression in PBMC cultures. Ordination plot of NMDS site scores representing Bray-Curtis distance dissimilarities between each treatment. The three-dimensions of the plot provide an excellent representation of the data in reduced dimensions (stress<0.05).

DETAILED DESCRIPTION

Described herein are compositions and methods for treating and/or alleviating symptoms of adverse reactions, such as an increased anti-inflammatory response, triggered by infectious diseases or conditions. Current therapies for the treatment of increased anti-inflammatory responses, such as cytokine storm, aim to dampen the immune system response. The treatments include blocking specific cytokines, such as IL-6 with tocilizumab or siltuximab, and generalized immunosuppressive drugs, such as corticosteroids. However, immunosuppressive drugs are accompanied by many negative side effects such as increasing susceptibility to infections and can interfere with anti-cancer immunotherapies. Recently, COVID-19 has been shown to cause cytokine storm and potentially cause death. Thus, there remains a need for alternative medicines that have decreased side effects and can be used in all patients. Polysaccharides in mushrooms have been shown to initiate an immune response, sparking activity of TNF-α, IL-1β, IL-6, and other pro-inflammatory proteins involved in acute immune activation. Concern has been raised regarding isolated polysaccharide extracts and induction of IL-1β, an inflammatory cytokine that may exacerbate the runaway inflammatory presentations in later stages of COVID-19. However, we have shown that other biologically active compounds in mushrooms and mycelium (such as the sterols, phenols, and other terpenoid compounds) are important for the resolution of this inflammatory response, inducing anti-inflammatory cytokines such as IL-10 and IL-1ra. Therefore, it is surprising that an unextracted whole mushroom mycelium complex impacts the immune system in a balanced and modulatory manner and may decrease cytokine storm.

As used herein, the terms "comprise(s)," "include(s)," "having," "has," "can," "contain(s)," and variants thereof, to be open-ended transitional phrases, terms, or words that do not preclude the possibility of additional acts or structures. As used herein, the terms "a," "an," "the" and similar terms used in the context of the disclosure (especially in the context of the claims) are to be construed to cover both the singular and plural unless otherwise indicated herein or clearly contradicted by the context. In addition, "a," "an," or "the" means "one or more" unless otherwise specified. The term "or" can be conjunctive or disjunctive. The present disclosure also contemplates other embodiments "comprising," "consisting of," and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

As used herein, the term "about" or "approximately" as applied to one or more values of interest, refers to a value that is similar to a stated reference value, or within an acceptable error range for the particular value as determined by one of ordinary skill in the art, which will depend in part on how the value is measured or determined, such as the limitations of the measurement system. The term "about" as used herein refers to any values, including both integers and fractional components that are within a variation of up to ±10% of the value modified by the term "about." In certain aspects, the term "about" refers to a range of values that fall within 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). Alternatively, "about" can mean within 3 or more than 3 standard deviations, per the practice in the art. Alternatively, such as with respect to biological systems or processes, the term "about" can mean within an order of magnitude, in some embodiments within 5-fold, and in some embodiments within 2-fold, of a value.

As used herein, all percentages (%) used for compositions or formulations refer to mass (or weight, w/w) percent unless noted otherwise.

The terms "active ingredient" or "active pharmaceutical ingredient" as used herein refer to a pharmaceutical agent, active ingredient, compound, or substance, compositions, or mixtures thereof, that provide a pharmacological, often beneficial, effect.

As used herein, the terms "administering," "providing" and "introducing" are used interchangeably herein and refer to the placement of the compositions of the disclosure into a subject by a method or route which results in at least partial localization of the composition to a desired site. The compositions can be administered by any appropriate route which results in delivery to a desired location in the subject.

As used herein, the terms "control," "reference level," and "reference" are used interchangeably and refer to a predetermined value or range, which is employed as a benchmark against which to assess the measured result. "Control group"

as used herein refers to a group of control subjects. The predetermined level may be a cutoff value from a control group. The predetermined level may be an average from a control group. Cutoff values (or predetermined cutoff values) may be determined by Adaptive Index Model (AIM) methodology. Cutoff values (or predetermined cutoff values) may be determined by a receiver operating curve (ROC) analysis from biological samples of a patient group. ROC analysis, as generally known in the biological arts, is a determination of the ability of a test to discriminate one condition from another, e.g., to determine the performance of each marker in identifying a patient having COVID-19. A description of ROC analysis is provided in P. J. Heagerty et al., *Biometrics* 56: 337-44 (2000), the disclosure of which is hereby incorporated by reference in its entirety. Alternatively, cutoff values may be determined by a quartile analysis of biological samples of a patient group. For example, a cutoff value may be determined by selecting a value that corresponds to any value in the $25^{th}$-$75^{th}$ percentile range, in some embodiments a value that corresponds to the $25^{th}$ percentile, the percentile or the $75^{th}$ percentile, and in some embodiments the $75^{th}$ percentile. Such statistical analyses may be performed using any method known in the art and can be implemented through any number of commercially available software packages (e.g., from Analyse-it Software Ltd., Leeds, UK; StataCorp LP, College Station, TX; SAS Institute Inc., Cary, NC.). The healthy or normal levels or ranges for a target or for a protein activity may be defined in accordance with standard practice. A control may be a subject or cell without an agonist as detailed herein. A control may be a subject, or a sample therefrom, whose disease state is known. The subject, or sample therefrom, may be healthy, diseased, diseased prior to treatment, diseased during treatment, or diseased after treatment, or a combination thereof.

The term "dose" as used herein denotes any form of the active ingredient formulation or composition that contains an amount sufficient to produce a therapeutic effect with at least a single administration. "Formulation" and "composition" are used interchangeably herein.

The term "dosage" as used herein refers to the administering of a specific amount, number, and frequency of doses over a specified period of time, typically 1 day.

As used herein, the terms "effective amount," "therapeutically effective amount," or "therapeutically effective rate (s)" refers to a substantially non-toxic, but sufficient amount or delivery rates of an agent or a composition or combination of compositions being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. It is understood that various biological factors may affect the ability of an agent to perform its intended task. Therefore, an "effective amount," "therapeutically effective amount," or "therapeutically effective rate(s)" may be dependent in some instances on such biological factors. For example, the precise determination of what would be considered an effective dose may be based on factors individual to each patient, including, but not limited to, the patient's age, size, type or extent of disease, stage of the disease, route of administration, the type or extent of supplemental therapy used, ongoing disease process and type of treatment desired (e.g., aggressive vs. conventional treatment). Further, while the achievement of therapeutic effects may be measured by a physician or a qualified medical practitioner using evaluations known in the art, it is recognized that individual variation and response to treatments may make the achievement of therapeutic effects a subjective decision. An appropriate "effective" amount in any individual case may be determined using techniques, such as a dose escalation study. The dose could be administered in one or more administrations. The determination of a therapeutically effective amount or delivery rate is well within the ordinary skill in the art of pharmaceutical sciences and medicine.

As used herein, "formulation" and "composition" can be used interchangeably and refer to a combination of at least two ingredients. In some embodiments, at least one ingredient may be an active agent or otherwise have properties that exert physiologic activity when administered to a subject. For example, a mixture including at least two ingredients (e.g., water and Tv) and is itself a composition or formulation.

As used herein, the terms "inhibit," "inhibition," or "inhibiting" refer to the reduction or suppression of a given condition, symptom, or disorder, or disease, or a significant decrease in the baseline activity of a biological activity or process.

As used herein, a subject is "in need of" a treatment if such subject would benefit biologically, medically, or in quality of life from such treatment.

As used herein, the term "preventing" refers to a reduction in the frequency of, or delay in the onset of, symptoms of the condition or disease.

As used herein, the term "prophylaxis" refers to preventing or reducing the progression of a disorder, either to a statistically significant degree or to a degree detectable to one skilled in the art.

As used herein, the terms "sample" or "test sample" refers any sample in which the presence and/or level of a target is to be detected or determined or any sample treated with the compositions as detailed herein. Samples may include liquids, solutions, emulsions, or suspensions. Samples may include a medical sample. Samples may include any biological fluid or tissue, such as blood, whole blood, fractions of blood such as plasma and serum, muscle, interstitial fluid, sweat, saliva, urine, tears, synovial fluid, bone marrow, cerebrospinal fluid, nasal secretions, sputum, amniotic fluid, bronchoalveolar lavage fluid, gastric lavage, emesis, fecal matter, lung tissue, peripheral blood mononuclear cells, total white blood cells, lymph node cells, spleen cells, tonsil cells, cancer cells, tumor cells, bile, digestive fluid, skin, or combinations thereof. In some embodiments, the sample comprises an aliquot. In other embodiments, the sample comprises a biological fluid. Samples can be obtained by any means known in the art. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

As used herein, the terms "subject," "study participant," "participant," and "patient" interchangeably refer to any vertebrate, including, but not limited to, a mammal that wants or is in need of the herein described compositions or methods. The subject may be a human or a non-human. The subject may be a vertebrate. The subject may be a mammal. The mammal may be a primate or a non-primate. The mammal can be a non-primate such as, for example, cow, pig, camel, llama, hedgehog, anteater, platypus, elephant, alpaca, horse, goat, rabbit, sheep, hamsters, guinea pig, cat, dog, rat, and mouse. The mammal can be a primate such as a human. The mammal can be a non-human primate such as, for example, monkey, cynomolgus monkey, rhesus monkey, chimpanzee, gorilla, orangutan, and gibbon. The subject may be of any age or stage of development, such as, for example, an adult, an adolescent, or an infant. The subject may be male. The subject may be female. In some embodiments, the subject has a specific genetic marker. The subject may be undergoing other forms of treatment.

As used herein, the term "substantially" means to a great or significant extent, but not completely.

As used herein, the terms "therapeutic composition" and "pharmaceutical composition" can be used interchangeably and refer to a combination of at least two ingredients.

As used herein, the terms "treat," "treating," or "treatment" of any disease or disorder refer to ameliorating the disease or disorder (i.e., slowing or arresting or reducing the development of the disease or at least one of the clinical symptoms thereof). In an embodiment, "treat," "treating," or "treatment" refers to alleviating or ameliorating at least one physical parameter including those which may not be discernible by a subject.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, mycology, immunology, microbiology, genetics, and protein and nucleic acid chemistry described herein are those that are well known and commonly used in the art. The meaning and scope of the terms should be clear; in the event however of any latent ambiguity, definitions provided herein take precedent over any dictionary or extrinsic definition. Further, unless otherwise required by context, singular terms shall include pluralities and plural terms shall include the singular.

Various embodiments of the disclosure are described herein. It will be recognized that features specified in each embodiment may be combined with other specified features, including as indicated in the embodiments below, to provide further embodiments of the present disclosure.

It is understood that in the following embodiments, combinations of substituents or variables of the depicted formulae are permissible only if such combinations result in stable compounds.

Cytokine Storm

The term "increased anti-inflammatory response" as used herein refers to an exacerbated immune response to an infection, therapeutic, or autologous or allogeneic cells and tissues. The increased anti-inflammatory response may be a dysregulated pro-inflammatory cytokine response to an infection, therapeutic, or autologous or allogeneic cells and tissues. The increased anti-inflammatory response includes the rapid release of pro-inflammatory and anti-inflammatory cytokines, where the release of these initial cytokines can lead to an inflammatory cascade. The increased anti-inflammatory response may be a cytokine storm.

As used herein, the terms "cytokine storm," "cytokine release syndrome," "macrophage activation syndrome," and "hemophagocytic lymphohistiocytosis" interchangeably refer to the dysregulation of pro-inflammatory and anti-inflammatory cytokines leading to disease. A cytokine storm may be referred to as being part of a sequence because one cytokine typically leads to the production of multiple other cytokines that can reinforce and amplify the immune response. Cytokine storm is a potentially life-threatening cytokine-associated toxicity. Diagnosing and management of cytokine storm is routinely based on clinical parameters and symptoms, such as identifying biomarkers (e.g., gene products (e.g., polypeptides, gene expression and/or protein expression profiles), or other analytes). Cytokine storm results from high-level immune activation when large numbers of lymphocytes and/or myeloid cells release inflammatory cytokines upon activation. The severity of the cytokine storm and the timing of onset of symptoms can vary depending on the magnitude of immune cell activation. The pro-inflammatory mediators involved in cytokine storm are divided into two subgroups: early mediators and late mediators. The transcription factor interferon regulatory factor 5 (IRF5) is critical for pro-inflammatory cytokine production. The inflammatory response to influenza infection is known to increase glucose metabolism. Glucose metabolism is required for activating IRF5-induced cytokine production, specifically the hexosamine biosynthesis pathway. Hexosamine biosynthesis results in the end product uridine diphosphate N-acetylglucosamine (UDP-GlcNAc). Through O-GlcNAcylation, UDP-GlcNAc is added to proteins to modify their activity. It has been shown that O-GlcNAcylation of IRF5 is necessary for IRF5-mediated cytokine production. It also has been shown that influenza patients have higher blood glucose levels and more O-GlcNacylation of IRF5 than healthy controls and that blood glucose levels are highly correlated with levels of inflammatory cytokines. Therefore, glucose metabolism plays a role in the development of cytokine storm.

Disease conditions commonly associated with a cytokine storm include but are not limited to: sepsis, systemic inflammatory response syndrome (SIRS), cachexia, septic shock syndrome, traumatic brain injury (e.g., cerebral cytokine storm), graft versus host disease (GVHD), or the result of treatment with activated immune cells, e.g., IL-2 activated T cells, T cells activated with anti-CD19 Chimeric Antigen Receptor (CAR) T cells. Infectious diseases commonly associated with cytokine storm include viral, bacterial, and parasitic infections. The viral infectious diseases include, but are not limited to, Paramyxoviridae (respiratory syncytial virus (RSV), parainfluenza virus (PIV), metapneumovirus (MPV), enteroviruses), Picornaviridae (Rhinovirus, RV), Coronaviridae (CoV), Adenoviridae (Adenovirus), Parvoviridae (H BoV), Orthomyxoviridae (influenza A, B, C, D, Isavirus, Thogotovirus, Quaranjavirus), Herpesviridae (human herpes viruses, *Varicella zoster* virus, Epstein-Barr virus, cytomegalovirus), avian influenza, smallpox, pandemic influenza, adult respiratory distress syndrome (ARDS). CoV can include one or more of Severe Acute Respiratory Syndrome (SARS-CoV), Middle East Respiratory Syndrome (MERS-CoV), COVID-19 (2019-nCoV, SARS-CoV-2), 229E, NL63, OC43, or HKU1. The bacterial infectious diseases include, but are not limited to, *Streptococcus pneumoniae, Mycobacterium tuberculosis, Bordetella pertussis, Haemophilus influenzae, Moraxella catarrhalis, Pseudomonas aeruginosa, Stenotrophomonas maltophila, Staphylococcus aureus, Streptococcus pyogenes, Neisseria meningitidis, Klebsiella pneumoniae,* or Non-tuberculosis *Mycobacterium*. The parasitic infectious diseases include, but are not limited to, malaria.

Coronaviruses (CoVs), are enveloped positive-sense RNA viruses, which are surrounded by crown-shaped, club-like spikes projection on the outer surface. Coronaviruses' spike proteins are glycoproteins that are embedded over the viral envelope. This spike protein attaches to specific cellular receptors and initiates structural changes of spike protein, and causes penetration of cell membranes, which results in the release of the viral nucleocapsid into the cell. These spike proteins determine host trophism. Coronaviruses have a large RNA genome, ranging in size from 26 to 32 kilobases and capable of obtaining distinct ways of replication. Like other RNA viruses, coronaviruses under-go replication of the genome and transcription of mRNAs upon infection. Coronavirus infection in a subject can result in significant and long-term damage of the lungs, leading to possibly sever respiratory issues.

As used herein "2019-nCoV" is a betacoronavirus (Beta-CoV or β-CoV). In particular, 2019-nCoV is a Beta-CoV of lineage B. 2019-nCoV may also be known as SARS-CoV-2 or 2019 novel coronavirus. Betacoronaviruses are one of four genera of coronaviruses and are enveloped, positive-sense, single-stranded RNA viruses of zoonotic origin. Betacoronaviruses mainly infect bats, but they also infect other species like humans, camels, and rabbits. 2019-nCoV may be transferable between animals, such as between humans. As used herein "viral transmission" is the process by which viruses spread between host subjects. Transmission occurs from person to person by direct or indirect contact or exposure. Examples of direct contact include, but are not limited to, the exchange of body fluids between a subject infected with the virus and someone else. Indirect contact includes, but is not limited to, exposure to bodily fluid droplets produced by a subject infected by the virus during coughing and/or sneezing. Beta-CoVs may induce fever and respiratory symptoms in humans. The overall structure of β-CoV genome contains an ORF1ab replicase polyprotein (rep, pp1ab) preceding other elements. This polyprotein is cleaved into many nonstructural proteins. 2019-nCoV has a phenylalanine in the (F486) in the flexible loop of the receptor binding domain, flexible glycyl residues, and a four amino acid insertion at the boundary between the S1 and S2 subunits that results in the introduction of a furin cleavage site. The furin cleavage site may result in 2019-nCoV tissue tropism, increase transmissibility, and alter pathogenicity.

Diagnosis of 2019-nCoV may comprise a positive test for 2019-nCoV and/or onset of 2019-nCoV symptoms, or combinations thereof. Symptoms of 2019-nCoV include, but are not limited to, one or more of the following symptoms: nasal congestion, sore throat, fever, body aches, exhaustion, dry cough, difficulty breathing, loss of taste, loss of smell, or a combination thereof. The methods and compositions herein can recover or aid in the recovery of taste and smell. Subjects may also experience long-term effects from COVID-19, where symptoms can persist for weeks or months after the initial infection and disappear and reappear after infection. Long-term COVID-19 symptoms include, but are not limited to, one or more of shortness of breath, cough, fatigue, joint pain, chest pain, difficulty with thinking and/or concentration (i.e. "brain fog"), depression, anxiety, changes in mood, muscle pain, headache, intermittent fever, heart palpitations, inflammation of the heart, lung function abnormalities, acute kidney injury, rash, hair loss, smell and/or taste problems, sleep issues, and difficulty with memory. Subjects who experience long-term effects from COVID-19 are known as long-haulers. The methods and compositions herein may treat long-term COVID-19 or decrease the symptoms thereof. Subjects at higher risk of developing complications may be immunocompromised (e.g., undergoing cancer treatment, bone marrow or organ transplantation, immune deficiencies, poorly controlled HIV or AIDS, prolonged use of corticosteroids or immune weakening medications), have an underlying medical condition (e.g., diabetes, renal failure, liver disease), are pregnant, are at least 65 years of age, have a chronic lung disease, have a heart disease, or combinations thereof.

Symptoms of cytokine storm can include neurologic toxicity, disseminated intravascular coagulation, cardiac dysfunction, adult respiratory distress syndrome, renal failure, and/or hepatic failure. For example, symptoms of cytokine storm can include fever with or without rigors, fatigue, malaise, myalgias, vomiting, headache, nausea, anorexia, arthralgias, diarrhea, rash, hypoxemia, tachypnea, hypotension, widened pulse pressure, potentially diminished cardiac output (late), increased cardiac output (early), azotemia, hypofibrinogenemia with or without bleeding, elevated D-dimer, hyperbilirubinemia, transaminitis, confusion, delirium, mental status changes, hallucinations, tremor, seizures, altered gait, word finding difficulty, frank aphasia, elevated heart rate, coagulopathy, MODS (multiple organ dysfunction syndrome), cardiovascular dysfunction, distributive shock, cardiomyopathy, hepatic dysfunction, renal dysfunction, encephalopathy, clinical seizures, respiratory failure, tachycardia, or dysmetria.

IL-6 is thought to be a mediator of cytokine storm toxicity. High IL-6 levels may initiate a proinflammatory IL-6 signaling cascade, leading to one or more of the cytokine storm symptoms. IL-6 and soluble IL-6 receptor (sIL-6R) levels can be measured for example, by methods described in Chen et al. Chen et al., *J. Immunol. Meth.* 434:1-8 (2016). In some cases, the level of C-reactive protein (CRP) (a biomolecule produced by the liver, e.g., in response to IL-6) can be a measure of IL-6 activity. In some cases, CRP levels may increase several-fold (e.g., several logs or orders of magnitude) during cytokine storm. CRP levels can be measured using standard methods available in the art. Spiking IL-6 is dangerous for COVID-19 as it potentiates a cytokine storm, therefore current clinical trials aim to suppress IL-6 in COVID-19 patients. The compositions described herein spike IL-6 while simultaneously spiking IL-10 and IL-1ra, and therefore surprisingly reduces cytokine storms, neuroinflammation, and blood clotting.

Rapidly proliferating and highly activated T-cells or natural killer (NK) cells that result in the exaggerated release of cytokines during a cytokine storm can include more than 150 inflammatory mediators such as cytokines, oxygen free radicals, and coagulation factors. Both pro-inflammatory cytokines (such as TNF-α, IL-1, and IL-6) and anti-inflammatory cytokines (such as IL-10, and IL-1 receptor antagonist (IL-1RA)) become greatly elevated in, for example, serum. It is this excessive release of inflammatory mediators that triggers the cytokine storm.

A "pro-inflammatory cytokine" or a "pro-inflammatory mediator" is an immuno-regulatory cytokine that induces inflammation. A pro-inflammatory cytokine may upregulate or increase the synthesis of secondary pro-inflammatory mediators and other pro-inflammatory cytokines by immune cells. In addition, pro-inflammatory cytokines can stimulate production of acute phase proteins that mediate inflammation and attract inflammatory cells. Pro-inflammatory cytokines that are generally responsible for early immune responses include IL-1, IL-6, and TNF-α. IL-1, IL-6, and TNF-α are also considered endogenous pyrogens as they contribute to increasing body temperature. Other examples of pro-inflammatory cytokines or pro-inflammatory mediators include IL-2, IL-4, IL-5, IL-6, IL-7, IL-8, IL-9, IL-11, IL-12p70, IL-13, IL-15, IL-17A, IL-18, interferon (IFN)-γ, monocyte chemoattractant protein (MCP) 1, eotaxin, interferon gamma-induced protein (IP) 10, granulocyte colony-stimulating factor (GM-CSF), macrophage inflammatory protein (MIP) 1α, MIP 1β, RANTES, leukemia, inhibitory factors (LIF), oncostatin M (OSM), and a variety of chemokines that attract inflammatory cells.

IL-1 is an important pro-inflammatory cytokine. IL-1 is a soluble protein having a mass of approximately 17 kilo-Daltons (kD). IL-1 is produced by a variety of cells, for example macrophages, white blood cells, lymphocytes, monocytes, dendritic cells, and accessory cells that are involved in activation of T-lymphocytes and B-lymphocytes. IL-1 is typically released by such cells during an immune response. IL-1 is generally considered to be a pro-inflammatory cytokine. The original members of the IL-1 superfamily are IL-1α, IL-β, and IL-1 receptor antagonist (IL-1RA). Both IL-1α and IL-1β play important roles in the inflammatory response of the body against pathogens or infection and recognize the same IL-1 receptor and perform similar biological functions. IL-1α is predominantly a cell-associated molecule whereas IL-1β is generally a secreted molecule. The term "IL-1" as used herein includes one or both of IL-1α and IL-1β. IL-1 can increase the expression of adhesion factors on endothelial cells to enable transmigration of leukocytes to sites of infection. In addition, IL-1 can stimulate the hypothalamus thermoregulatory center to cause an increase in body temperature (e.g., a fever). In particular, IL-1β is involved in a range of cellular activities such as cell proliferation, cell differentiation, cell apoptosis, and pain. TNF-α is involved in systemic inflammation and works in tandem with a variety of other cytokines to stimulate the acute phase immune reaction. TNF-α can induce apoptotic cell death as well as inhibit tumorigenesis and viral replication. TNF-α and IL-1 can work simultaneously and synergistically in stimulating and sustaining inflammation within the body.

"Anti-inflammatory cytokines" or "anti-inflammatory mediators" refer generally to immuno-regulatory cytokines that inhibit or counteract various aspects of inflammation. In other words, anti-inflammatory cytokines counteract various biological effects of pro-inflammatory cytokines and pro-inflammatory mediators. Anti-inflammatory cytokines can control or mitigate the magnitude of inflammation. Functions of anti-inflammatory cytokines include inhibiting production of pro-inflammatory cytokines and inhibiting cell activation. Examples of anti-inflammatory cytokines include, but are not limited to, IL-1RA, IL-2, IL-4, IL-7, IL-9, IL-10, IL-13, or IL-15. IL-2 is a variably glycosylated single protein molecule having as mass of approximately 15.5 kD. IL-2 is generally produced by activated T helper cells (also known as effector T cells) during an immune response. Pathogens (also known as antigens) that invade or are introduced within the body bind to receptors that are found on the surfaces of lymphocytes. Binding of such pathogens or antigens to T cell receptors (TCR) stimulates secretion of IL-2. IL-2 mediates its effects by binding to IL-2 receptor molecules, which are expressed by lymphocytes. The binding of IL-2 to its receptor molecule triggers a signaling cascade, for example Ras/MAPK, JAK/Stat, and PI 3-kinase/Akt signaling modules. IL-2 has numerous functions including facilitating production of immunoglobulins (Ig) by B cells. In addition, IL-2 induces differentiation and proliferation of NK cells and stimulates growth, differentiation, and proliferation of antigen-selected cytotoxic T cells via induction gene expression. IL-2 is considered to be important for the development of T cell immunologic memory and is necessary during T cell development in the thymus for enabling the maturation of regulatory T cells.

Given the mutability of viruses as they jump from host to host, many variants of viruses can evolve and emerge, with some becoming more damaging and deadlier. Although vaccines and antiviral drugs can be effective against one strain of virus when they are designed and tested, these continuous mutations can result in vaccine evasion or loss in drug potency. Viruses or other pathogens that can evade the efficacy of vaccines and drugs, make these disease agents more virulent, more contagious, and ultimately more deadly to those infected. Hence, by augmenting immunity while downregulating specific cytokines can help not only lessen the degree of infection but also prevent cytokine storms, making vaccines, anti-viral drugs and other treatments more effective. The methods and compositions described herein, in conjunction with conventional therapies such as vaccines and antiviral drugs, may potentiate the recovery of patients infected with viruses such as COVID, flu viruses and other known viruses, due to the immune enhancement properties coupled with the anti-inflammatory effects of the methods and compositions described herein, and the stimulation of IL-10 and IL1ra by the methods and compositions described herein. Moreover, the use of the methods and compositions as described herein can help enhance innate immunity of patients who suffer from viruses that are immune evasive. Examples of immune evasion include but are not limited to cancer-causing viruses (oncoviruses) that are responsible for Merkel Cell Carcinoma, and the many forms of human papillomavirus (HPV) and Herpes induced cancers. In essence, these mushroom adjuvant therapies described herein can enhance innate immune system, helping decloak or sensitize these disease agents and in some cases the cancers they cause, while augmenting better immune detection, targeting, and vaccine/drug efficacy—enhancing recovery. The methods and compositions herein can enhance a wide range of conventional therapies currently in practice for fighting viral and microbial diseases. Conventional viral therapies include, but are not limited to, vaccines such as live attenuated virus vaccines, attenuated virus vaccines, mRNA vaccines, cell-based vaccines, recombinant vaccines, adjuvant vaccines, or quadrivalent vaccines; and antiviral drugs such as oseltamivir (Tamiflu), zanamivir (Relenza), peramivir (Rapivab) or baloxavir (Xofluza).

Pain and Cytokines

A unique combination of molecular and cellular factors can lead to acute and chronic pain conditions with varying pathologies. Pain can be categorized into the following broad categories: inflammatory, neuropathic, and syndrome-based (e.g., fibromyalgia). There is overlap between these generalized categories. For example, inflammation can result in nerve damage, nerve injury involves inflammation, and syndrome-based pain can be neuropathic or inflammatory or both. Inflammatory pain occurs with peripheral tissue damage and the resulting tissue inflammation. Alternatively, neuropathic pain results from direct damage to nerves in the peripheral or central nervous systems. Postoperative pain has both inflammatory and neuropathic qualities. It is widely recognized that postoperative pain occurs as a result of the direct cutting of tissues and peripheral nerves at the surgical site. Examples of pain conditions include pain associated with psychological conditions, pain associated with infections (e.g., bacterial or viral infections), abdominal pain, abnormal gastrointestinal motility pain, acute herpes zoster pain, acute inflammatory pain, acute intermittent pain, acute musculoskeletal pain, acute obstetric pain, acute pain, acute post-operative pain (e.g., bunionectomy pain; abdominoplasty pain; knee pain from a total knee replacement; hip pain from a total hip replacement; pain from a laminectomy; pain from a hernia repair; or hemorrhoid removal pain), acute tendonitis pain, acute visceral pain, adiposis dolorosa pain, amyotrophic lateral sclerosis pain, angina-induced pain, anti-retroviral therapy induced neuralgia, anxiety pain, appendicitis pain, arrhythmia pain, arthritis pain, ataxia pain, back pain, Behcet's disease pain, bipolar disorder pain, bladder and urogenital disease pain, bone pain, bowel obstruction pain, brachial plexus avulsion injury pain, breakthrough pain, burn pain, burning mouth syndrome pain, bursitis pain, cancer chemotherapy induced neuralgia, cancer pain, cardiac arrhythmia pain, cardiac pain, carpal tunnel syndrome pain, central pain, cerebral ischemia, Cesarean-section pain, Charcot-Marie Tooth neuropathic pain, chemotherapy induced neuropathic pain, chest pain, cholecystitis pain, chronic and acute headache pain, chronic and acute neuropathic pain, chronic arthritis, chronic pain, chronic visceral pain, cluster headache pain, cold pain, complex regional pain syndrome, Crohn's disease pain, dental pain (e.g., third molar extraction), depression pain, diabetic neuralgia, diabetic neuropathic pain, diabetic peripheral neuropathic pain, drug therapy induced neuralgia, ectopic proximal and distal discharge pain, endometriosis pain, epilepsy pain, erythromelalgia pain, exercise induced angina pain, exercise induced pain, exercise pain, Fabry's disease pain, femur cancer pain, fibromyalgia pain, general neuralgias, granuloma annulare pain, Guillain-Barre pain, gut pain, Haglund syndrome pain, head pain, headache pain, hereditary sensory neuropathic pain, hernia pain, herpetic neuralgia pain, HIV-associated neuropathic pain, HIV-associated sensory neuropathic pain, hyperactivity bladder pain, hypertension pain, idiopathic pain, idiopathic sensory neuropathic pain, idiopathic small-fiber neuropathic pain, incontinence pain, inflammatory bowel disease pain, inflammatory pain, injury pain, interstitial cystitis (IC) pain, intestinal obstruction pain, intractable pain, irritable bowel syndrome pain, joint pain, labor pain, leprosy pain, lipoidica pain, malignancy pain, mechanical low back pain, migraine pain, Morton's neuroma pain, movement disorder pain, multiple sclerosis (MS) pain, musculoskeletal pain, myofascial pain syndrome pain, myotonia pain, neck pain, necrobiosis pain, nerve avulsion injury pain, nerve entrapment injury pain, neurodegenerative disorder pain, neuroendocrine disorder pain, neuropathic low back pain, neuropathic pain, nociceptive pain, non-malignant chronic bone pain, orofacial pain, osteoarthritis pain, painful bladder syndrome, painful legs, painful moving toes, painful neuromas, palpitations, pancreatic pain, paroxysmal extreme pain, pathological cough pain, pelvic pain, peripheral nerve injury pain, phantom pain, phlebitic pain, post spinal cord injury pain, post-amputation pain, post-herpetic neuralgia, post-mastectomy pain, post-stroke pain, postsurgical pain, premenstrual pain, prostatitis pain, pruritis pain, psychiatric disorder associated pain, pyelonephritis pain, radicular pain, radiculopathy, radiotherapy-induced neuropathic pain, renal colic pain, rheumatoid arthritis pain, sarcoidosis pain, sciatica pain, severe pain, shingles pain, sickle cell anemia pain, sinusitis pain, soft tissue pain, spinal cord injury pain, spinal stenosis pain, sports injury pain, stress-induced angina pain, stress-induced pain, stroke pain, temporomandibular joint pain, tendonitis pain, tension headache pain, thalamic pain, tinnitus pain, trauma pain, traumatic brain injury pain, traumatic neuroma, trigeminal autonomic cephalalgia, trigeminal neuralgia, tumor pain, urinary incontinence pain, visceral pain, widespread pain, or other types of pain.

There is a robust immune response in pain conditions and following injury that includes infiltration of neutrophils, macrophages, and lymphocytes. The immune response aids in wound healing, but also results in sensitization of sensory neurons to various stimuli such as mechanical and heat stimuli. When an injury occurs in the periphery, the immune response begins at the site of tissue damage and moves proximally to the dorsal root ganglia and spinal cord. Immune cells interact with sensory neurons and activate canonical immune receptors expressed by neurons in both the peripheral and central nervous systems. For example, neurons express immune receptors such as toll-like receptors (e.g., TLR4, TLR9) and cytokine receptors for cytokines such as TNF-α, IL-1, IL-6, IL-10, IL-1RA, etc. Components of the innate immune system have emerged as crucial mediators in the development and maintenance of hypersensitivity following nerve injury.

Compounds

In one embodiment described herein, the composition comprises an aqueous or solid fraction of a mycelium or fruit body, a fermented substrate thereof, or a combination thereof. In one aspect, the extract comprises a mixture of compounds or isolated compounds comprising one or more of acetovanillone, baeocystin, (4-phosphoryloxy-N-methyl-tryptamine), beta-sitosterol, caffeic acid, cannabidiol, cannabichromene, cannabigerol, Δ8-tetrahydrocannabinol, Δ9-tetrahydrocannabinol, cannabinol, tetrahydrocannabivarin, cannabidiol-2',6'-dimethyl ether, chrysin, cordycepin, cordysinin, davallialactone, dehydrosulphurenic acid, eburicoic acid, ellagic acid, ergosterols, Erinacine A, Erinacine B, Erinacine C, Erinacine D, Erinacine E, Erinacine F, Erinacine G, Erinacine H, Erinacine I, Erinacine J, Erinacine K, Erinacine P, Erinacine Q, Erinacine R, erinacines, erinacol, ethyl 7-chloro-2-oxo-4-phenyl-2H-chromen-3-carboxylate, ethyl vanillin, eugenol, ferulic acid, gallic acid, guaiacol, glucans, β-glucans, harmane, harmine, harmol, Hericenone A, Hericenone B, Hericenone C, Hericenone D, Hericenone E, Hericenone F, Hericenone G, Hericenone H, hericenones, hexanal, hispidin, hispolons, 4-hydroxybenzoic acid, 4-hydroxytryptamine, hypholomine B, inoscavin A, inotodiol, lanosterol, linoleic acids, N,N-dimethyltryptamine, norbaeocystin (4-phosphoryloxy-tryptamine), norharmine, norpsilocin (4-hydroxy-N-methyl-tryptamine), p-coumaric acid, perlolyrine, phelligridin D, p-hydroxybenzaldehyde, p-hydroxybenzoic acid, protocatechuic acid, psilocin (4-hydroxy-N,N-dimethyltryptamine), psilocybin (4-phosphoryloxy-N,N-dimethyltryptamine), quercetin, rutin, shikimic acid, sinapinic acid, stigmasterol, sulphurenic acid, syringic acid, trametenolic acid, trans-cinnamic acid, trans-coumaric acid, trans-ferulic acid, tryptamines, vanillic acid, β-carbolines, alkaloids, amino acids, anthranilic acid alkaloids, apiole, (+)-aromanderndrene, asarone, aurones, benzofuranoids, benzofurans, benzophenones, benzopyranoids, benzopyrans, benztropolones, cis-α-bergamotene, trans-α-bergamotene, α-bisabolol, borneol, γ-cadinene, caffeic acid, camphor, carbohydrates, carotenoids, 3-carene, β-carbolines, trans-β-caryophyllene, catechins, chalcones, chavicol, chavicols, chromones, cineol, cinnamic acid, cinnamic aldehydes, cinnamic monolignols, conferyl alcohol, coniferyl alcohol, cordysinin, coumarins, coumaric acid, coumaryl alcohol, cutin, depsides, depsidones, dillapiole, diterpenes, diterpenoids, γ-elemene, elemicin, eleutherosides, esterterpenoids, estragole, eudesman-3,7(11)-diene, β-eudesmol, γ-eudesmol, eugenol, trans-β-farnesene, ferulic acid, haramane, harmine, norharmine, harmol, α-humuline, β-fenchol, 5-hydroxyferulic acid, fla-
vonoids, glycopeptides, hydroxycinnamic acids, hydroxy-
lated fatty acids, imidazole alkaloids, isoflavonoids, isoqui-
noline alkaloids, β-lactams, lignans, limonoids, R-limonene,
(−)-linalool, lipids, lysine alkaloids, meroterpenoids, methyl
eugenol, miscellaneous terpenoids, monoterpenoid indole
alkaloids, monoterpenoids, myrcene, myristicin, nerolidol,
nicotinic acid alkaloids, cis-ocimene, 1-octanol, ornithine
alkaloids, otenoids, oxazole alkaloids, oxygen heterocycles,
peptides, phellanderene, phenolics, phenylalanine alkaloids,
phenylpropanoids, phenylpropanoids., phenylpropenes, per-
lolyrine, pinene, polycyclic aromatic natural products,
polyketide alkaloids, polyketides, polypyrroles, ptteridines,
purines, putrescine alkaloids, pyrazine alkaloids, pyrimi-
dines, pyrrole alkaloids, quassinoids, quinonemethides, qui-
nones, quinoxaline alkaloids, resveratrol, trans-resveratrol,
cis-sabinene hydrate, safrole, γ-selinene, semiochemicals,
septide alkaloids, sesquiterpenes, sesquiterpenoids, simple
aromatic natural products, sinapic acid, sinapyl alcohols,
spermidine alkaloids, spermine alkaloids, sporopollenin,
steroidal alkaloids, steroids, sterols, stilbenes, stilbenoids,
suberin, tannins, terpenoid alkaloids, terpenoids, γ-ter-
pinene, α-terpineol, terpinolene, tetraterpenoids, thiazole
alkaloids, triterpenes, triterpenoids, tryptophan alkaloids,
tyrosine alkaloids, umbelliferone, xanthone, or pharmaceu-
tically acceptable salts, hydrates, solvates, prodrugs, stereoi-
somers, or tautomers thereof, or combinations thereof.

Pharmaceutically Acceptable Salts

Pharmaceutically acceptable salts of the compounds
described herein are also contemplated for the uses
described herein. As used herein, the terms "salt" or "salts"
refer to an acid addition or base addition salt of a compound
described herein. "Salts" include in particular "pharmaceu-
tical acceptable salts." The term "pharmaceutically accept-
able salts" refers to salts that retain the biological effective-
ness and properties of the compounds disclosed herein and,
which typically are not biologically or otherwise undesir-
able. In many cases, the compounds disclosed herein can
form acid and/or base salts by virtue of the presence of
amino and/or carboxyl groups or groups similar thereto.

Pharmaceutically acceptable acid addition salts can be
formed with inorganic acids and organic acids.

Inorganic acids from which salts can be derived include,
for example, hydrochloric acid, hydrobromic acid, sulfuric
acid, nitric acid, phosphoric acid, and the like.

Organic acids from which salts can be derived include, for
example, acetic acid, propionic acid, glycolic acid, oxalic
acid, maleic acid, malonic acid, succinic acid, fumaric acid,
tartaric acid, citric acid, benzoic acid, mandelic acid, meth-
anesulfonic acid, ethanesulfonic acid, toluenesulfonic acid,
sulfosalicylic acid, and the like.

Pharmaceutically acceptable base addition salts can be
formed with inorganic and organic bases. Inorganic bases
from which salts can be derived include, for example,
ammonium salts and metals from columns I to XII of the
periodic table. In certain embodiments, the salts are derived
from sodium, potassium, ammonium, calcium, magnesium,
iron, silver, zinc, and copper; particularly suitable salts
include ammonium, potassium, sodium, calcium, and mag-
nesium salts.

Organic bases from which salts can be derived include,
for example, primary, secondary, and tertiary amines, sub-
stituted amines including naturally occurring substituted
amines, cyclic amines, basic ion exchange resins, and the
like. Certain organic amines include isopropylamine, benzathine, cholinate, diethanolamine, diethylamine, lysine,
meglumine, piperazine, and tromethamine.

Another embodiment is one or more compounds extracted
from or isolated from *Agaricus blazei, Cordyceps militaris,
Flammulina velutipes, Fomes fomentarius, Fomitopsis offi-
cinalis, Ganoderma applanatum* s.l., *Ganoderma lucidum*
s.l., *Ganoderma oregonense* s.l., *Grifola frondosa, Hericium
erinaceus, Inonotus obliquus, Lentinula edodes, Phellinus
linteus, Piptoporus betulinus, Pleurotus ostreatus, Schizo-
phyllum commune, Trametes versicolor* can be formulated as
an acetate, ascorbate, adipate, aspartate, benzoate, besylate,
bromide/hydrobromide, bicarbonate/carbonate, bisulfate/
sulfate, camphorsulfonate, caprate, chloride/hydrochloride,
chlortheophyllonate, citrate, ethandisulfonate, fumarate,
gluceptate, gluconate, glucuronate, glutamate, glutarate,
glycolate, hippurate, hydroiodide/iodide, isethionate, lac-
tate, lactobionate, laurylsulfate, malate, maleate, malonate,
mandelate, mesylate, methylsulphate, mucate, naphthoate,
napsylate, nicotinate, nitrate, octadecanoate, oleate, oxalate,
palmitate, pamoate, phosphate/hydrogen phosphate/dihy-
drogen phosphate, polygalacturonate, propionate, sebacate,
stearate, succinate, sulfosalicylate, sulfate, tartrate, tosylate,
trifenatate, trifluoroacetate, or xinafoate salt form.

Pharmaceutical Compositions

Another embodiment is a pharmaceutical composition
comprising an aqueous or solid fraction of a mycelium or
fruit body, a fermented substrate thereof, or a combination
thereof, one or more compounds described herein or a
pharmaceutically acceptable salt, hydrate, solvate, prodrug,
stereoisomer, or tautomer thereof, and one or more pharma-
ceutically acceptable carrier(s). The term "pharmaceutically
acceptable carrier" refers to a pharmaceutically acceptable
material, composition or vehicle, such as a liquid or solid
filler, diluent, excipient, solvent or encapsulating material,
involved in carrying or transporting any subject composition
or component thereof. Each carrier must be "acceptable" in
the sense of being compatible with the subject composition
and its components and not injurious to the subject.

Pharmaceutical excipients useful for the compositions as
described herein comprise: acidifying agents (acetic acid,
glacial acetic acid, citric acid, fumaric acid, hydrochloric
acid, diluted hydrochloric acid, malic acid, nitric acid,
phosphoric acid, diluted phosphoric acid, sulfuric acid,
tartaric acid); alkalizing agents (ammonia solution, ammo-
nium carbonate, diethanolamine, diisopropanolamine,
potassium hydroxide, sodium bicarbonate, sodium borate,
sodium carbonate, sodium hydroxide, trolamine); antifoam-
ing agents (dimethicone, simethicone); antimicrobial preser-
vatives (benzalkonium chloride, benzalkonium chloride
solution, benzethonium chloride, benzoic acid, benzyl alco-
hol, butylparaben, cetylpyridinium chloride, chlorobutanol,
chlorocresol, cresol, dehydroacetic acid, ethylparaben,
methylparaben, methylparaben sodium, phenol, phenylethyl
alcohol, phenylmercuric acetate, phenylmercuric nitrate,
potassium benzoate, potassium sorbate, propylparaben, pro-
pylparaben sodium, sodium benzoate, sodium dehydroac-
etate, sodium propionate, ascorbic acid, thimerosal, thymol);
antioxidants (ascorbic acid, ascorbyl palmitate, butylated
hydroxyanisole, butylated hydroxytoluene, hypophospho-
rous acid, monothioglycerol, propyl gallate, sodium form-
aldehyde sulfoxylate, sodium metabisulfite, sodium thiosul-
fate, sulfur dioxide, tocopherol, tocopherols excipient);
buffering agents (acetic acid, ammonium carbonate, ammo-
nium phosphate, boric acid, citric acid, lactic acid, phos-
phoric acid, potassium citrate, potassium metaphosphate, potassium phosphate monobasic, sodium acetate, sodium citrate, sodium lactate solution, dibasic sodium phosphate, monobasic sodium phosphate, phosphate buffer saline); chelating agents (edetate disodium, ethylenediaminetetraacetic acid and salts, edetic acid); coating agents (sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyvinyl acetate phthalate, shellac, sucrose, titanium dioxide, carnauba wax, microcrystalline wax, zein); colorants (caramel, red, yellow, black or blends, ferric oxide); complexing agents (ethylenediaminetetraacetic acid and salts (EDTA), edetic acid, gentisic acid ethanolamide, oxyquinoline sulfate); desiccants (calcium chloride, calcium sulfate, silicon dioxide); emulsifying and/or solubilizing agents (acacia, cholesterol, diethanolamine (adjunct), glyceryl monostearate, lanolin alcohols, mono- and di-glycerides, monoethanolamine (adjunct), lecithin, oleic acid (adjunct), oleyl alcohol (stabilizer), poloxamer, polyoxyethylene 50 stearate, polyoxyl 35 castor oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, diacetate, monostearate, sodium lauryl sulfate, sodium stearate, sorbitan monolaurate, sorbitan monooleate, sorbitan monopalmitate, sorbitan monostearate, stearic acid, trolamine, emulsifying wax); filtering aids (powdered cellulose, purified siliceous earth); flavors and perfumes (anethole, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, vanillin); humectants (glycerol, hexylene glycol, sorbitol); plasticizers (e.g., castor oil, diacetylated monoglycerides, diethyl phthalate, glycerol, mono- and di-acetylated monoglycerides, propylene glycol, triacetin, triethyl citrate); polymers (e.g., cellulose acetate, alkyl celluloses, hydroxyalkyl, acrylic polymers and copolymers); solvents (acetone, alcohol, diluted alcohol, amylene hydrate, benzyl benzoate, butyl alcohol, carbon tetrachloride, chloroform, corn oil, cottonseed oil, ethyl acetate, glycerol, hexylene glycol, isopropyl alcohol, methyl alcohol, methylene chloride, methyl isobutyl ketone, mineral oil, peanut oil, propylene carbonate, sesame oil, water for injection, sterile water for injection, sterile water for irrigation, purified water); sorbents (powdered cellulose, charcoal, purified siliceous earth); carbon dioxide sorbents (barium hydroxide lime, soda lime); stiffening agents (hydrogenated castor oil, cetostearyl alcohol, cetyl alcohol, cetyl esters wax, hard fat, paraffin, polyethylene excipient, stearyl alcohol, emulsifying wax, white wax, yellow wax); suspending and/or viscosity-increasing agents (acacia, agar, alginic acid, aluminum monostearate, bentonite, purified bentonite, magma bentonite, carbomer, carboxymethylcellulose calcium, carboxymethylcellulose sodium, carboxymethylcellulose sodium carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, alginate, silicon dioxide, colloidal silicon dioxide, sodium alginate, tragacanth, xanthan gum); sweetening agents (aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup); surfactants (simethicone); tablet binders (acacia, alginic acid, sodium carboxymethylcellulose, microcrystalline cellulose, dextrin, ethylcellulose, gelatin, liquid glucose, guar gum, hydroxypropyl methylcellulose, methylcellulose, polyethylene oxide, povidone, pregelatinized starch, syrup); tablet and/or capsule diluents (calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, confectioner's sugar); tablet disintegrants (alginic acid, microcrystalline cellulose, croscarmellose sodium, crospovidone, polacrilin potassium, sodium starch glycolate, starch, pregelatinized starch); tablet and/or capsule lubricants (calcium stearate, glyceryl behenate, magnesium stearate, light mineral oil, sodium stearyl fumarate, stearic acid, purified stearic acid, talc, hydrogenated vegetable oil, zinc stearate); thickening agents (gelatin having a bloom strength of 50-100); tonicity agent (dextrose, glycerol, mannitol, potassium chloride, sodium chloride); vehicle: flavored and/or sweetened (aromatic elixir, compound benzaldehyde elixir, iso-alcoholic elixir, peppermint water, sorbitol solution, syrup, tolu balsam syrup); vehicle: oleaginous (almond oil, corn oil, cottonseed oil, ethyl oleate, isopropyl myristate, isopropyl palmitate, mineral oil, light mineral oil, myristyl alcohol, octyl dodecanol, olive oil, peanut oil, persic oil, sesame oil, soybean oil, squalane); vehicle: solid carrier (sugar spheres); vehicle: sterile (bacteriostatic water for injection, bacteriostatic sodium chloride injection); viscosity-increasing (see suspending agent); water repelling agents (cyclomethicone, dimethicone, simethicone); and/or solubilizing agent (benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaurate, sorbitan monooleate, sorbitan monopalmitate, sorbitan monostearate, tyloxapol). This list is not meant to be exclusive, but instead merely representative of the classes of excipients and the particular excipients that may be used in, for example, oral dosage forms as described herein. See *Remington's Essentials of Pharmaceutics*, Pharmaceutical Press Publishing Company, London, UK, 1$^{st}$ Edition, 2013, and the *Handbook of Pharmaceutical Excipients,* 8$^{th}$ Edition, Pharmaceutical Press Publishing Company London, UK, 2017, each of which is incorporated by reference herein for such teachings.

Certain compounds described herein may exist in particular geometric or stereoisomeric forms. A particular enantiomer of a compound described herein may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Another embodiment is a method for manufacturing a dosage form comprising formulating a composition as described herein comprising sprays, capsules, tablets, elixirs, emulsions, lozenges, suspensions, syrups, pills, lotions, epidermal patches, suppositories, inhalers, or injectables. Any methods known to the art for formulating extracts or active principal ingredients into lotions, soaps, etc. may be utilized. In some embodiments, the composition may be in the form of a capsule.

The compositions described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In some embodiments, the compositions of the disclosure are administered orally, intraperitoneally, or intravenously. Sterile injectable forms of the compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tween®, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions described herein may be orally administered in any orally acceptable dosage form including, but not limited to, capsules, tablets, aqueous suspensions, or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring, or coloring agents may also be added.

Alternatively, the pharmaceutically acceptable compositions of this disclosure may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax, and polyethylene glycols.

The pharmaceutically acceptable compositions of this disclosure may also be administered topically, especially when the target of treatment includes areas or organs readily accessible by topical application, including diseases of the eye, the skin, or the lower intestinal tract. Suitable topical formulations are readily prepared for each of these areas or organs. Topical application for the lower intestinal tract can be administered using a rectal suppository formulation (see above) or a suitable enema formulation. Topically transdermal patches may also be used.

For topical applications, the pharmaceutically acceptable compositions may be formulated in a suitable ointment containing the active component suspended or dissolved in one or more carriers. Carriers for topical administration of the compounds of this disclosure include, but are not limited to, mineral oil, liquid petrolatum, white petrolatum, propylene glycol, polyoxyethylene, polyoxypropylene compound, emulsifying wax, and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol, and water.

The pharmaceutically acceptable compositions of this disclosure may also be administered by nasal aerosol or inhalation. Such compositions are prepared according to techniques known in the art of pharmaceutical formulation and may be prepared as solutions in saline, employing benzyl alcohol or other suitable preservatives, absorption promoters to enhance bioavailability, fluorocarbons, or other conventional solubilizing or dispersing agents. The amount of the compounds of the present disclosure that may be combined with the carrier materials to produce a composition in a single dosage form will vary depending upon the host treated and the mode of administration. Preferably, the compositions should be formulated so that a dosage of between 0.01-100 mg/kg body weight/day of the active ingredient can be administered to a patient receiving these compositions.

In some embodiments, the composition may include an aqueous or solid fraction of a mycelium or fruit body, a fermented substrate thereof, or a combination thereof. The mycelium or fruit body may be one or more of *Agaricus blazei, Cordyceps militaris, Flammulina velutipes, Fomes fomentarius, Fomitopsis officinalis, Ganoderma applanatum* s.l., *Ganoderma lucidum* s.l., *Ganoderma oregonense* s.l., *Grifola frondosa, Hericium erinaceus, Inonotus obliquus, Lentinula edodes, Phellinus linteus, Piptoporus betulinus, Pleurotus ostreatus, Schizophyllum commune, Trametes versicolor, Psilocybe cubensis, Psilocybe azurescens*, or *Psilocybe cyanescens*. The mycelium or fruit body may be *Trametes versicolor*. The aqueous or solid fraction of the mycelium, fermented substrate, or combination thereof may include beta-glucans. In one embodiment, the composition is described in Table 1.

TABLE 1

| Exemplary Compositions | | |
| --- | --- | --- |
| Component | Example | Dosage |
| Aqueous or solid fraction of a mushroom mycelium and/or fruit body mixture | *Agaricus blazei, Cordyceps militaris, Flammulina velutipes, Fomes fomentarius, Fomitopsis officinalis, Ganoderma applanatum s.l., Ganoderma lucidum s.l., Ganoderma oregonense s.l., Grifola frondosa, Hericium erinaceus, Inonotus obliquus, Lentinula edodes, Phellinus linteus, Piptoporus betulinus, Pleurotus ostreatus, Schizophyllum commune, Trametes versicolor* | 200 mg-10 g |
| Aqueous ethyl acetate, or solid fraction of a mycelium, a fermented substrate thereof, or a combination thereof | *Agaricus blazei, Cordyceps militaris, Flammulina velutipes, Fomes fomentarius, Fomitopsis officinalis, Ganoderma applanatum s.l., Ganoderma lucidum s.l., Ganoderma oregonense s.l., Grifola frondosa, Hericium erinaceus, Inonotus obliquus, Lentinula edodes, Phellinus linteus, Piptoporus betulinus, Pleurotus ostreatus, Schizophyllum commune, Trametes versicolor, Psilocybe cubensis, Psilocybe azurescens, or Psilocybe cyanescens* | 200 mg-10 g |
| Aqueous, hydroethanolic, or ethanolic extract of a mycelium | *Agaricus blazei, Cordyceps militaris, Flammulina velutipes, Fomes fomentarius, Fomitopsis officinalis, Ganoderma applanatum s.l., Ganoderma lucidum s.l., Ganoderma oregonense s.l., Grifola frondosa, Hericium erinaceus, Inonotus obliquus, Lentinula edodes, Phellinus linteus, Piptoporus betulinus, Pleurotus ostreatus, Schizophyllum commune, Trametes versicolor, Psilocybe cubensis, Psilocybe azurescens, or Psilocybe cyanescens* | 200 mg-10 g |
| Dried mycelium powder | *Agaricus blazei, Cordyceps militaris, Flammulina velutipes, Fomes fomentarius, Fomitopsis officinalis, Ganoderma applanatum s.l., Ganoderma lucidum s.l., Ganoderma oregonense s.l., Grifola frondosa, Hericium erinaceus, Inonotus obliquus, Lentinula edodes, Phellinus linteus, Piptoporus betulinus, Pleurotus ostreatus, Schizophyllum commune, Trametes versicolor, Psilocybe cubensis, Psilocybe azurescens, or Psilocybe cyanescens* | 200 mg-10 g |
| Optional pharmaceutical excipients | Fillers, binders, solvents, diluents, vehicles, lubricants, preservatives, flavors, colors, buffering agents, etc. | 0.05-75% by weight |

Compositions can be liquid, suspensions, emulsions, dry powder admixtures, or combinations thereof.

In another embodiment, the composition may include an aqueous or solid fraction of a mycelium or fruit body, a fermented substrate thereof, or a combination thereof combined with an extract of one or more of *Agaricus augustus, Agaricus blazei, Agaricus bonardii, Agaricus brasiliensis, Agaricus campestris, Agaricus lilaceps, Agaricus subrufescens, Agaricus sylvicola, Agrocybe aegerita, Agrocybe arvalis, Agrocybe pediades, Agrocybe praecox, Antrodia cinnamonea, Clitocybe odora, Conocybe cyanopus, Conocybe lacteus, Conocybe rickenii, Conocybe smithii, Conocybe tenera, Coprinopsis lagopus, Coprinopsis nivea, Coprinus comatus, Coprinus micaceus, Fomitiporia robusta, Fomitopsis officinalis (Laricifomes officinalis), Ganoderma atrum, Ganoderma brownii, Ganoderma curtisii, Ganoderma lingzhi, Ganoderma oregonense, Ganoderma tsugae, Gymnopus hydrophilus, Gymnopus peronatus, Hericium erinaceus, Hericium coralloides, Hericium ramosum, Heterobasidion annosum, Hypholoma aurantiaca (Leratiomyces ceres), Hypholoma capnoides, Hypholoma sublateritium, Hypsizygus marmoreus, Hypsizygus tessulatus, Hypsizygus ulmarius, Inonotus andersonii, Inonotus dryadeus, Inonotus hispidus, Laetiporus cincinnatus, Laetiporus conifericola, Laetiporus sulphureus, Lentinus ponderosus, Lenzites betulina, Lepiota procera (Macrolepiota procera), Lepiota rachodes (Chlorophyllum rachodes), Lepista nuda, Mycena alcalina, Mycena aurantiadisca, Mycena pura, Panaeolus foenisecii, Panaeolus subbalteatus, Panellus serotinus, Panellus serotinus, Panellus stipticus, Phellinus igniarius, Phellinus linteus, Phellinus pini, Piptoporus betulinus, Pleurotus columbinus, Pleurotus cystidiosus, Pleurotus ostreatus, Pleurotus pulmonarius, Pleurotus sapidus, Pleurotus tuberregium, Pluteus cervinus, Polyporus elegans, Psathyrella aquatica, Psathyrella condolleana, Psathyrella hydrophila, Psilocybe allenii, Psilocybe azurescens, Psilocybe caerulescens, Psilocybe coprophila, Psilocybe cubensis, Psilocybe cyanescens, Psilocybe ovoideocystidiata, Psilocybe stuntzii, Psilocybe subaeruginosa, Stereum complicatum, Stereum hirsutum, Stereum ostrea, Stropharia aeruginosa, Stropharia cyanea, Stropharia rugoso-annulata, Stropharia semiglobata, Stropharia semigloboides, Stropharia squamosa, Stropharia thrausta, Stropharia umbonotescens, Termitomyces robusta, Trametes aesculi, Trametes cingulata, Trametes ectypa, Trametes elegans, Trametes gibbosa, Trametes hir-*

*suta, Trametes ochracea, Trametes pubescens, Trametes villosa, Volvaria bombycina, Volvariella volvacea, Woffiporia cocos*, or combinations thereof.

In another embodiment, the composition may include an aqueous or solid fraction of a mycelium or fruit body, a fermented substrate thereof, or a combination thereof combined with one or more extracts or pure chemicals from plant species comprising one or more of *Bacopa* species (*Bacopa monnien*), Gotu kola (*Centella asiatica*), and Gingko (*Gingko biloba*, Ginger (*Zingiber officinale*), Holy Basil (*Ocimum sanctum*), Hu Zhang (*Polygonum cuspidatum*), Oregano (*Origanum vulgare, Origanum onites*), Rosemary (*Rosmarinus officinalis, Rosmarinus eriocalyx*, species in the genus *Rosmarinus*), Turmeric (*Curcuma longa*), Green Tea (*Camellia sinensis*), lavender (*Lavandula spica* and related species in the genus *Lavandula*), skullcap (*Scutellaria lateriflora*) oat straw (*Avena sativa, Avena byzantina*), *Salvia divinorum*, aka Diviner's Sage, *Banisteriopsis caapi* and *Psychotria* species, plants containing ibogaine (*Tabemanthe iboga, Voacanga africana* and *Tabemaemontana undulate*), peyote (*Lophophora williamsii*), the seeds of morning glory (*Ipomoea tricolor* and related species) and Hawaiian baby wood rose (*Argyreia nervosa*), *Acacia confusa, Acacia obtusifolia, Acacia simplicifolia, Desmanthus Illinoensis*, or Cannabis (*Cannabis sativa, C. indica* and *C. ruderalis*).

Dosages

Toxicity and therapeutic efficacy of compounds described herein, including pharmaceutically acceptable salts and deuterated variants, can be determined by standard pharmaceutical procedures in cell cultures or experimental animals. The $LD_{50}$ is the dose lethal to 50% of the population. The $ED_{50}$ is the dose therapeutically effective in 50% of the population. The dose ratio between toxic and therapeutic effects ($LD_{50}/ED_{50}$) is the therapeutic index. Compounds that exhibit large therapeutic indexes are preferred. While compounds that exhibit toxic side effects may be used, care should be taken to design a delivery system that targets such compounds to the site of affected tissue in order to minimize potential damage to uninfected cells and thereby reduce side effects.

Data obtained from the cell culture assays and animal studies can be used in formulating a range of dosage for use in humans. The dosage of such compounds may lie within a range of circulating concentrations that include the $ED_{50}$ with little or no toxicity. The dosage may vary within this range depending upon the dosage form employed and the route of administration utilized. For any compound, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated.

The amount of a compound described herein in the composition will also depend upon the particular compound in the composition.

In one embodiment, the pharmaceutical compositions described herein provide a dosage form of the pharmaceutical compositions described here for administration to a subject. In one embodiment, the subject is suffering from or has the symptoms of one or more neurologic diseases or disorders or wishes to enhance one or more cognitive or sensory motor traits. The dosage form can be administered, for example, to a subject, or a subject in need thereof. In one aspect, the subject is a mammal, or a mammal in need thereof. In one aspect, the subject is a human, or human in need thereof. In one aspect, the subject is a human or a human in need thereof. In one aspect, the subject is a child (~0-9 years old) or an adolescent (~10-17 years old). In one aspect, the subject is from about 0 to about 9 years of age. In another aspect, the subject is from about 10 years to about 17 years of age. In another aspect, the subject is over 17 years of age. In another aspect, the subject is an adult (≥18 years of age).

One or more dosage forms of the compositions described herein can be administered, for example, 1×, 2×, 3×, 4×, 5×, 6×, or even more times per day. One or more dosage forms can be administered, for example, for 1, 2, 3, 4, 5, 6, 7 days, or even longer. One or more dosage forms can be administered, for example, for 1, 2, 3, 4 weeks, or even longer. One or more dosage forms can be administered, for example, for 1, 2, 3, 4, 5, 6, 7, 8, 9, 10, 11, 12 months, 1 year, 2, years, 3 years, 4 years, 5 years, over 5 years, a decade, multiple decades, or even longer. One or more dosage forms can be administered at a regular interval until the subject or subject in need thereof, does not require treatment, prophylaxis, or amelioration of any disease or condition including but not limited to a neurological or neurodegenerative disease or disorder.

In one embodiment, the compositions described herein can be administered as dosage forms in various regimens, including one dose per day (QD), two doses per day (BID), three doses per day (TID), or four times per day (QID) to achieve a total daily dosage. In another embodiment, any of the foregoing doses comprise a total daily dosage.

Methods of Treatment

Methods for treating, prophylaxis of, or ameliorating symptoms of an infectious disease including administering an effective amount of the compositions detailed herein are contemplated. Methods for treating, prophylaxis of, or ameliorating symptoms of a bacterial or viral infection or modulating a bacterial or viral infection that includes administering an effective amount of an aqueous or solid extract of one or more of *Agaricus brasiliensis* f. *blazei, Cordyceps militaris, Flammulina velutipes, Fomes fomentarius, Fomitopsis officinalis, Ganoderma applanatum, Ganoderma lucidum* s.l., *Ganoderma oregonense* s.l., *Grifola frondosa, Hericium erinaceus, Inonotus obliquus, Lentinula edodes, Phellinus linteus, Piptoporus betulinus, Pleurotus ostreatus, Schizophyllum commune*, and/or *Trametes versicolor* are also contemplated. Another embodiment described herein is a method of treating a subject suffering from or having the symptoms of an infectious disease or disorder by orally administering one or more of the pharmaceutical compositions described herein to the subject. The composition may be administered in one or more doses, one or more times per day for a total daily dosage. In one aspect, the compositions described herein are effective to at least partially treat, alleviate, prevent, or ameliorate symptoms of an infectious disease. Further, provided herein are means for modulating an inflammatory response that includes administering to a subject an effective amount of the composition described herein.

In some embodiments, a dose of the composition may be administered to the subject 1 time per day, 2 times per day, 3 times per day, 4 times per day, or 5 times per day. In some embodiments, the dose includes at least 1 capsule, at least 2 capsules, at least 3 capsules, at least 4 capsules, at least 5 capsules, at least 6 capsules, at least 7 capsules, at least 8 capsules. In some embodiments, the composition may be administered to the subject for about 1 to 30 consecutive days, about 5 to 30 consecutive days, about 10 to 30 consecutive days, about 15 to 30 consecutive days, about 1 to 15 consecutive days, about 5 to 15 consecutive days, or about 10 to 15 consecutive days. In some embodiments, the composition may be administered to the subject for about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, or about 30 days.

For example, administration of the composition to the subject may result in inhibition or slowing of the infectious disease. In another example, administration of the composition to the subject may result in inhibition or slowing of the normal rate of increase of viral load as compared to an untreated subject. As used herein, the term "viral load" is a measurement of the amount of a virus in a subject. In some embodiments, the infectious disease may cause lung inflammation. The lung inflammation may be associated with, but not limited to, respiratory failure, respiratory distress, pulmonary disease, cystic fibrosis, asthma, bronchitis, inflammation/swelling of the lungs, chronic obstructive pulmonary disease (COPD), pneumonia, restrictive lung disease, bronchiectasis, pulmonary fibrosis, sarcoidosis, allergies, smoking, emphysema, acute respiratory distress syndrome (ARDS), interstitial lung disease (ILD), pneumoconiosis or lung cancer. The lung diseases may affect the alveoli, trachea, interstitium, pluera, bronchi and/or bronchioles. The lung disease may cause diffuse alveolar damage, denuded alveolar lining cells with reactive type II pneumocyte hyperplasia, intra-alveolar fibrinous exudates, loose interstitial fibrosis, intra-alveolar loose fibrous plugs of organizing pneumonia, intra-alveolar organizing fibrin, damaged alveolar epithelial cells, desquamated cells within the alveolar space, cellular fibromyxoid exudates, desquamation of pneumocytes, hyaline membrane formation (e.g. indication of ARDS), pulmonary oedema, (e.g. early-phase ARDS). The lung disease may also cause chronic inflammation such as interstitial mononuclear inflammatory infiltrates dominated by lymphocytes. The lung disease may cause infiltration of the intra-alveolar spaces in the lung by multinucleated syncytial cells with atypical enlarged pneumocytes characterized by large nuclei, amphophilic granular cytoplasm, and/or prominent nucleoli that show viral cytopathic-like changes. The lung disease may cause increased inflammatory FCN1+ macrophages that replace FABP4+ macrophages in severe disease. The lung disease may cause highly expanded and functional competent tissue resident clonal CD8+ T cells in mild disease. Blood vessels or interstitial areas between alveoli may not be affected by the lung disease. In some embodiments, the infectious disease may include one or more symptoms such as shortness of breath, wheezing, coughing, yellow mucus, green mucus, blood-tinged mucus, chest pain, breathlessness, rapid breathing, hypoxia, inflammation of the lung tissue, rapid heart rate, or increased blood pressure, or decreased blood pressure. In some embodiments, the subject may have COPD, cardiovascular disease, diabetes mellitus, hypertension, or a combination thereof. In some embodiments, the subject may be at least 1 year old, at least 2 years old, at least 3 years old, at least 4 years old, at least 5 years old, at least 6 years old, at least 7 years old, at least 8 years old, at least 9 years old, at least 10 years old, at least 11 years old, at least 12 years old, at least 13 years old, at least 14 years old, at least 15 years old, at least 16 years old, at least 17 years old, at least 18 years old, at least 19 years old, at least 20 years old, at least 21 years old, at least 22 years old, at least 23 years old, at least 24 years old, at least 25 years old, at least 26 years old, at least 27 years old, at least 28 years old, at least 29 years old, at least 30 years old, at least 31 years old, at least 32 years old, at least 33 years old, at least 34 years old, at least 35 years old, at least 36 years old, at least 37 years old, at least 38 years old, at least 39 years old, at least 40 years old, at least 41 years old, at least 42 years old, at least 43 years old, at least 44 years old, at least 45 years old, at least 46 years old, at least 47 years old, at least 48 years old, at least 49 years old, at least 50 years old, at least 51 years old, at least 52 years old, at least 53 years old, at least 54 years old, at least 55 years old, at least 56 years old, at least 57 years old, at least 58 years old, at least 59 years old, at least 60 years old, at least 61 years old, at least 62 years old, at least 63 years old, at least 64 years old, at least 65 years old, at least 66 years old, at least 67 years old, at least 68 years old, at least 69 years old, at least 70 years old, at least 71 years old, at least 72 years old, at least 73 years old, at least 74 years old, at least 75 years old, at least 76 years old, at least 77 years old, at least 78 years old, at least 79 years old, at least 80 years old, at least 81 years old, at least 82 years old, at least 83 years old, at least 84 years old, at least 85 years old, at least 86 years old, at least 87 years old, at least 88 years old, at least 89 years old, at least 90 years old, at least 91 years old, at least 92 years old, at least 93 years old, at least 94 years old, at least 95 years old, at least 96 years old, at least 97 years old, at least 98 years old, at least 99 years old, at least 100 years old, or even older.

In some embodiments, the infectious disease or condition may increase expression of growth factors. In some embodiments, the growth factors may be basic fibroblast growth factor and/or vascular endothelial growth factor. In some embodiments, the methods herein comprise administering a therapy for one of the symptoms or conditions associated with cytokine storm. For instance, if the subject develops coagulopathy, the method may comprise administering cryoprecipitate. In some embodiments, if the subject develops cardiovascular dysfunction, the method may comprise administering vasoactive infusion support. In some embodiments, if the subject develops distributive shock, the method may comprise administering alpha-agonist therapy. In some embodiments, if the subject develops cardiomyopathy, the method may comprise administering milrinone therapy. In some embodiments, if the subject develops respiratory failure, the method may comprise performing mechanical ventilation (e.g., invasive mechanical ventilation or noninvasive mechanical ventilation). In some embodiments, if the subject develops shock, the method may comprise administering crystalloid and/or colloid fluids.

In the absence of prompt intervention, such as that provided herein, a cytokine storm can result in permanent lung damage and, in many cases, death. The end stage symptoms of the cytokine storm include but are not limited to hypotension, tachycardia, dyspnea, fever, ischemia or insufficient tissue perfusion, uncontrollable hemorrhage, severe metabolism dysregulation, and multisystem organ failure. Deaths from infectious diseases such as COVID-19, are not caused by the virus itself, but rather, the cytokine storm that causes uncontrollable hemorrhaging; severe metabolism dysregulation; hypotension; tachycardia; dyspnea; fever; ischemia or insufficient tissue perfusion; and multisystem organ failure.

Methods for treating, prophylaxis of, or ameliorating symptoms of any type of pain known in the art in a subject in need thereof including administering an effective amount of the compositions detailed herein are contemplated. In one aspect, the pain comprises one or more of pain associated with psychological conditions, pain associated with infections (e.g., bacterial or viral infections), abdominal pain, abnormal gastrointestinal motility pain, acute herpes zoster pain, acute inflammatory pain, acute intermittent pain, acute musculoskeletal pain, acute obstetric pain, acute pain, acute post-operative pain (e.g., bunionectomy pain; abdominoplasty pain; knee pain from a total knee replacement; hip pain from a total hip replacement; pain from a laminectomy; pain from a hernia repair; or hemorrhoid removal pain), acute tendonitis pain, acute visceral pain, adiposis dolorosa pain, amyotrophic lateral sclerosis pain, angina-induced pain, anti-retroviral therapy induced neuralgia, anxiety pain, appendicitis pain, arrhythmia pain, arthritis pain, ataxia pain, back pain, Behcet's disease pain, bipolar disorder pain, bladder and urogenital disease pain, bone pain, brachial plexus avulsion injury pain, breakthrough pain, burn pain, burning mouth syndrome pain, bursitis pain, cancer chemotherapy induced neuralgia, cancer pain, cardiac arrhythmia pain, cardiac pain, carpal tunnel syndrome pain, central pain, cerebral ischemia, Cesarean-section pain, Charcot-Marie Tooth neuropathic pain, chemotherapy induced neuropathic pain, chest pain, cholecystitis pain, chronic and acute headache pain, chronic and acute neuropathic pain, chronic arthritis, chronic pain, chronic visceral pain, cluster headache pain, cold pain, complex regional pain syndrome, Crohn's disease pain, dental pain (e.g., third molar extraction), depression pain, diabetic neuralgia, diabetic neuropathic pain, diabetic peripheral neuropathic pain, drug therapy induced neuralgia, ectopic proximal and distal discharge pain, endometriosis pain, epilepsy pain, erythromelalgia pain, exercise induced angina pain, exercise induced pain, exercise pain, Fabry's disease pain, femur cancer pain, fibromyalgia pain, general neuralgias, granuloma annulare pain, Guillain-Barre pain, gut pain, Haglund syndrome pain, head pain, headache pain, hereditary sensory neuropathic pain, hernia pain, herpetic neuralgia pain, HIV-associated neuropathic pain, HIV-associated sensory neuropathic pain, hyperactivity bladder pain, hypertension pain, idiopathic pain, idiopathic sensory neuropathic pain, idiopathic small-fiber neuropathic pain, incontinence pain, inflammatory bowel disease pain, inflammatory pain, injury pain, interstitial cystitis (IC) pain, intestinal obstruction pain, intractable pain, irritable bowel syndrome pain, joint pain, labor pain, leprosy pain, lipoidica pain, malignancy pain, mechanical low back pain, migraine pain, Morton's neuroma pain, movement disorder pain, multiple sclerosis (MS) pain, musculoskeletal pain, myofascial pain syndrome pain, myotonia pain, neck pain, necrobiosis pain, nerve avulsion injury pain, nerve entrapment injury pain, neurodegenerative disorder pain, neuroendocrine disorder pain, neuropathic low back pain, neuropathic pain, nociceptive pain, non-malignant chronic bone pain, orofacial pain, osteoarthritis pain, painful bladder syndrome, painful legs, painful moving toes, painful neuromas, palpitations, pancreatic pain, paroxysmal extreme pain, pathological cough pain, pelvic pain, peripheral nerve injury pain, phantom pain, phlebitic pain, post spinal cord injury pain, post-amputation pain, post-herpetic neuralgia, post-mastectomy pain, post-stroke pain, postsurgical pain, premenstrual pain, prostatitis pain, pruritis pain, psychiatric disorder associated pain, pyelonephritis pain, radicular pain, radiculopathy, radiotherapy-induced neuropathic pain, renal colic pain, rheumatoid arthritis pain, sarcoidosis pain, sciatica pain, severe pain, shingles pain, sickle cell anemia pain, sinusitis pain, spinal cord injury pain, spinal stenosis pain, sports injury pain, stress-induced angina pain, stress-induced pain, stroke pain, temporomandibular joint pain, tendonitis pain, tension headache pain, thalamic pain, tinnitus pain, trauma pain, traumatic brain injury pain, traumatic neuroma, trigeminal autonomic cephalalgia, trigeminal neuralgia, urinary incontinence pain, visceral pain, widespread pain, or other types of pain.

Methods for treating, prophylaxis of, or ameliorating symptoms of any type of pain known in the art in a subject in need thereof that includes administering an effective amount of an aqueous or solid extract of one or more of *Agaricus brasiliensis* f. *blazei, Cordyceps militaris, Flammulina velutipes, Fomes fomentarius, Fomitopsis officinalis, Ganoderma applanatum, Ganoderma lucidum* s.l., *Ganoderma oregonense* s.l., *Grifola frondosa, Hericium erinaceus, Inonotus obliquus, Lentinula edodes, Phellinus linteus, Piptoporus betulinus, Pleurotus ostreatus, Schizophyllum commune,* and/or *Trametes versicolor* are also contemplated. Another embodiment described herein is a method of treating a subject suffering from or having the symptoms of any type of pain known in the art by orally administering one or more of the pharmaceutical compositions described herein to the subject. The composition may be administered in one or more doses, one or more times per day for a total daily dosage. In one aspect, the compositions described herein are effective to at least partially treat, alleviate, prevent, or ameliorate symptoms of any type of pain known in the art.

Methods of Use

Another embodiment is a method of treating or preventing an infectious disease or disorder in a subject in need thereof, the method comprising administering to the subject a therapeutically effective amount of an extract, a compound, or formulation disclosed herein. Another embodiment is a method of treating or lessening the severity of any type of pain in a subject in need thereof, the method comprising administering to the subject a therapeutically effective amount of an extract, a compound, or formulation disclosed herein.

Another embodiment is a composition comprising *Agaricus brasiliensis* f. *blazei, Cordyceps militaris, Flammulina velutipes, Fomes fomentarius, Fomitopsis officinalis, Ganoderma applanatum, Ganoderma lucidum* s.l., *Ganoderma oregonense* s.l., *Grifola frondosa, Hericium erinaceus, Inonotus obliquus, Lentinula edodes, Phellinus linteus, Piptoporus betulinus, Pleurotus ostreatus, Schizophyllum commune, Psilocybe cubensis, Psilocybe azurescens, Psilocybe cyanescens,* and/or *Trametes versicolor* extracts thereof, compounds isolated therefrom, or pharmaceutically acceptable salts, hydrates, solvates, prodrugs, stereoisomers, or tautomers thereof, or combinations thereof, and a pharmaceutically acceptable carrier, for use in treating an infectious disease or disorder in a subject in need thereof. Another embodiment is a composition comprising *Agaricus brasiliensis* f. *blazei, Cordyceps militaris, Flammulina velutipes, Fomes fomentarius, Fomitopsis officinalis, Ganoderma applanatum, Ganoderma lucidum* s.l., *Ganoderma oregonense* s.l., *Grifola frondosa, Hericium erinaceus, Inonotus obliquus, Lentinula edodes, Phellinus linteus, Piptoporus betulinus, Pleurotus ostreatus, Schizophyllum commune, Psilocybe cubensis, Psilocybe azurescens, Psilocybe cyanescens*, and/or *Trametes versicolor* extracts thereof, compounds isolated therefrom, or pharmaceutically acceptable salts, hydrates, solvates, prodrugs, stereoisomers, or tautomers thereof, or combinations thereof, and a pharmaceutically acceptable carrier, for use in treating or lessening the severity of any type of pain in a subject in need thereof.

Another embodiment is a composition comprising *Trametes versicolor* extracts thereof, compounds isolated therefrom, or pharmaceutically acceptable salts, hydrates, solvates, prodrugs, stereoisomers, or tautomers thereof, or combinations thereof and a pharmaceutically acceptable carrier, for use in treating an infectious disease or disorder in a subject in need thereof. Another embodiment is a composition comprising *Trametes versicolor* extracts thereof, compounds isolated therefrom, or pharmaceutically acceptable salts, hydrates, solvates, prodrugs, stereoisomers, or tautomers thereof, or combinations thereof and a pharmaceutically acceptable carrier, for use in treating or lessening the severity of any type of pain in a subject in need thereof.

Another embodiment is a composition comprising *Agaricus brasiliensis* f. *blazei, Cordyceps militaris, Flammulina velutipes, Fomes fomentarius, Fomitopsis officinalis, Ganoderma applanatum, Ganoderma lucidum* s.l., *Ganoderma oregonense* s.l., *Grifola frondosa, Hericium erinaceus, Inonotus obliquus, Lentinula edodes, Phellinus linteus, Piptoporus betulinus, Pleurotus ostreatus, Schizophyllum commune, Psilocybe cubensis, Psilocybe azurescens, Psilocybe cyanescens*, and/or *Trametes versicolor*, extracts thereof, compounds isolated therefrom, or pharmaceutically acceptable salts, hydrates, solvates, prodrugs, stereoisomers, or tautomers thereof, or combinations thereof for use in treating an infectious disease in a subject in need thereof. Another embodiment is a composition comprising *Agaricus brasiliensis* f. *blazei, Cordyceps militaris, Flammulina velutipes, Fomes fomentarius, Fomitopsis officinalis, Ganoderma applanatum, Ganoderma lucidum* s.l., *Ganoderma oregonense* s.l., *Grifola frondosa, Hericium erinaceus, Inonotus obliquus, Lentinula edodes, Phellinus linteus, Piptoporus betulinus, Pleurotus ostreatus, Schizophyllum commune, Psilocybe cubensis, Psilocybe azurescens, Psilocybe cyanescens*, and/or *Trametes versicolor*, extracts thereof, compounds isolated therefrom, or pharmaceutically acceptable salts, hydrates, solvates, prodrugs, stereoisomers, or tautomers thereof, or combinations thereof for use in treating or lessening the severity of any type of pain in a subject in need thereof.

Another embodiment is a composition comprising *Trametes versicolor* extracts thereof, compounds isolated therefrom, or pharmaceutically acceptable salts, hydrates, solvates, prodrugs, stereoisomers, or tautomers thereof, or combinations thereof for use in treating an infectious disease in a subject in need thereof. Another embodiment is a composition comprising *Trametes versicolor* extracts thereof, compounds isolated therefrom, or pharmaceutically acceptable salts, hydrates, solvates, prodrugs, stereoisomers, or tautomers thereof, or combinations thereof for use in treating or lessening the severity of any type of pain in a subject in need thereof.

Another embodiment is the use of a composition comprising *Agaricus brasiliensis* f. *blazei, Cordyceps militaris, Flammulina velutipes, Fomes fomentarius, Fomitopsis officinalis, Ganoderma applanatum, Ganoderma lucidum* s.l., *Ganoderma oregonense* s.l., *Grifola frondosa, Hericium erinaceus, Inonotus obliquus, Lentinula edodes, Phellinus linteus, Piptoporus betulinus, Pleurotus ostreatus, Schizophyllum commune, Psilocybe cubensis, Psilocybe azurescens, Psilocybe cyanescens*, and/or *Trametes versicolor* extracts thereof, compounds isolated therefrom, or pharmaceutically acceptable salts, hydrates, solvates, prodrugs, stereoisomers, or tautomers thereof, or combinations thereof in the manufacture of a medicament for treating an infectious disease or disorder. Another embodiment is the use of a composition comprising *Agaricus brasiliensis* f. *blazei, Cordyceps militaris, Flammulina velutipes, Fomes fomentarius, Fomitopsis officinalis, Ganoderma applanatum, Ganoderma lucidum* s.l., *Ganoderma oregonense* s.l., *Grifola frondosa, Hericium erinaceus, Inonotus obliquus, Lentinula edodes, Phellinus linteus, Piptoporus betulinus, Pleurotus ostreatus, Schizophyllum commune, Psilocybe cubensis, Psilocybe azurescens, Psilocybe cyanescens*, and/or *Trametes versicolor* extracts thereof, compounds isolated therefrom, or pharmaceutically acceptable salts, hydrates, solvates, prodrugs, stereoisomers, or tautomers thereof, or combinations thereof in the manufacture of a medicament for treating or lessening the severity of any type of pain.

Another embodiment is the use of a composition comprising *Trametes versicolor* in the manufacture of a medicament for treating an infectious disease or disorder. Another embodiment is the use of a composition comprising *Trametes versicolor* in the manufacture of a medicament for treating or lessening the severity of any type of pain.

Another embodiment is the use of a pharmaceutical composition comprising *Agaricus brasiliensis* f. *blazei, Cordyceps militaris, Flammulina velutipes, Fomes fomentarius, Fomitopsis officinalis, Ganoderma applanatum, Ganoderma lucidum* s.l., *Ganoderma oregonense* s.l., *Grifola frondosa, Hericium erinaceus, Inonotus obliquus, Lentinula edodes, Phellinus linteus, Piptoporus betulinus, Pleurotus ostreatus, Schizophyllum commune, Psilocybe cubensis, Psilocybe azurescens, Psilocybe cyanescens*, and/or *Trametes versicolor* extracts thereof, compounds isolated therefrom, or pharmaceutically acceptable salts, hydrates, solvates, prodrugs, stereoisomers, or tautomers thereof, or combinations thereof and a pharmaceutically acceptable carrier, in the manufacture of a medicament for treating an infectious disease in a subject in need thereof. Another embodiment is the use of a pharmaceutical composition comprising *Agaricus brasiliensis* f. *blazei, Cordyceps militaris, Flammulina velutipes, Fomes fomentarius, Fomitopsis officinalis, Ganoderma applanatum, Ganoderma lucidum* s.l., *Ganoderma oregonense* s.l., *Grifola frondosa, Hericium erinaceus, Inonotus obliquus, Lentinula edodes, Phellinus linteus, Piptoporus betulinus, Pleurotus ostreatus, Schizophyllum commune, Psilocybe cubensis, Psilocybe azurescens, Psilocybe cyanescens*, and/or *Trametes versicolor* extracts thereof, compounds isolated therefrom, or pharmaceutically acceptable salts, hydrates, solvates, prodrugs, stereoisomers, or tautomers thereof, or combinations thereof and a pharmaceutically acceptable carrier, in the manufacture of a medicament for treating or lessening the severity of any type of pain in a subject in need thereof.

Another embodiment is the use of a pharmaceutical composition comprising *Trametes versicolor* and a pharmaceutically acceptable carrier, in the manufacture of a medicament for treating an infectious disease in a subject in need thereof. Another embodiment is the use of a pharmaceutical composition comprising *Trametes versicolor* and a pharmaceutically acceptable carrier, in the manufacture of a medicament for treating or lessening the severity of any type of pain in a subject in need thereof.

Another embodiment is a use of a composition comprising *Agaricus brasiliensis* f. *blazei, Cordyceps militaris, Flammulina velutipes, Fomes fomentarius, Fomitopsis officinalis, Ganoderma applanatum, Ganoderma lucidum* s.l., *Ganoderma oregonense* s.l., *Grifola frondosa, Hericium erinaceus, Inonotus obliquus, Lentinula edodes, Phellinus linteus, Piptoporus betulinus, Pleurotus ostreatus, Schizophyllum commune, Psilocybe cubensis, Psilocybe azurescens,* or *Psilocybe cyanescens,* and/or *Trametes versicolor,* extracts thereof, compounds isolated therefrom, or pharmaceutically acceptable salts, hydrates, solvates, prodrugs, stereoisomers, or tautomers thereof, or combinations thereof in the manufacture of a medicament for treating or preventing an infectious disease or disorder in a subject in need thereof. Another embodiment is a use of a composition comprising *Agaricus brasiliensis* f. *blazei, Cordyceps militaris, Flammulina velutipes, Fomes fomentarius, Fomitopsis officinalis, Ganoderma applanatum, Ganoderma lucidum* s.l., *Ganoderma oregonense* s.l., *Grifola frondosa, Hericium erinaceus, Inonotus obliquus, Lentinula edodes, Phellinus linteus, Piptoporus betulinus, Pleurotus ostreatus, Schizophyllum commune, Psilocybe cubensis, Psilocybe azurescens,* or *Psilocybe cyanescens,* and/or *Trametes versicolor,* extracts thereof, compounds isolated therefrom, or pharmaceutically acceptable salts, hydrates, solvates, prodrugs, stereoisomers, or tautomers thereof, or combinations thereof in the manufacture of a medicament for treating or lessening the severity of any type of pain in a subject in need thereof.

Another embodiment is a use of a composition comprising *Trametes versicolor,* or a pharmaceutically acceptable salt, hydrate, solvate, prodrug, stereoisomer, or tautomer thereof, a combination thereof in the manufacture of a medicament for treating or preventing an infectious disease or disorder in a subject in need thereof. Another embodiment is a use of a composition comprising *Trametes versicolor,* or a pharmaceutically acceptable salt, hydrate, solvate, prodrug, stereoisomer, or tautomer thereof, a combination thereof in the manufacture of a medicament for treating or lessening the severity of any type of pain in a subject in need thereof.

Another embodiment is a method for treating or preventing an infectious disease or disorder in a subject in need thereof comprising administering a composition comprising *Agaricus brasiliensis* f. *blazei, Cordyceps militaris, Flammulina velutipes, Fomes fomentarius, Fomitopsis officinalis, Ganoderma applanatum, Ganoderma lucidum* s.l., *Ganoderma oregonense* s.l., *Grifola frondosa, Hericium erinaceus, Inonotus obliquus, Lentinula edodes, Phellinus linteus, Piptoporus betulinus, Pleurotus ostreatus, Schizophyllum commune, Trametes versicolor, Psilocybe cubensis, Psilocybe azurescens,* or *Psilocybe cyanescens,* extracts thereof, compounds isolated therefrom, or pharmaceutically acceptable salts, hydrates, solvates, prodrugs, stereoisomers, or tautomers thereof, or combinations thereof to the subject. Another embodiment is a method for treating or lessening the severity of any type of pain in a subject in need thereof comprising administering a composition comprising *Agari-*

*cus brasiliensis* f. *blazei, Cordyceps militaris, Flammulina velutipes, Fomes fomentarius, Fomitopsis officinalis, Ganoderma applanatum, Ganoderma lucidum* s.l., *Ganoderma oregonense* s.l., *Grifola frondosa, Hericium erinaceus, Inonotus obliquus, Lentinula edodes, Phellinus linteus, Piptoporus betulinus, Pleurotus ostreatus, Schizophyllum commune, Trametes versicolor, Psilocybe cubensis, Psilocybe azurescens,* or *Psilocybe cyanescens,* extracts thereof, compounds isolated therefrom, or pharmaceutically acceptable salts, hydrates, solvates, prodrugs, stereoisomers, or tautomers thereof, or combinations thereof to the subject.

Another embodiment is a method for treating or preventing an infectious disease or disorder in a subject in need thereof comprising administering a composition comprising *Trametes versicolor,* extracts thereof, compounds isolated therefrom, or pharmaceutically acceptable salts, hydrates, solvates, prodrugs, stereoisomers, or tautomers thereof, or combinations thereof to the subject. Another embodiment is a method for treating or lessening the severity of any type of pain in a subject in need thereof comprising administering a composition comprising *Trametes versicolor,* extracts thereof, compounds isolated therefrom, or pharmaceutically acceptable salts, hydrates, solvates, prodrugs, stereoisomers, or tautomers thereof, or combinations thereof to the subject.

Methods of Manufacturing

In an embodiment, is a method of manufacturing a composition comprising one or more of *Agaricus brasiliensis* f. *blazei, Cordyceps militaris, Flammulina velutipes, Fomes fomentarius, Fomitopsis officinalis, Ganoderma applanatum, Ganoderma lucidum* s.l., *Ganoderma oregonense* s.l., *Grifola frondosa, Hericium erinaceus, Inonotus obliquus, Lentinula edodes, Phellinus linteus, Piptoporus betulinus, Pleurotus ostreatus, Schizophyllum commune,* and/or *Trametes versicolor,* extracts thereof, compounds isolated therefrom, or pharmaceutically acceptable salts, hydrates, solvates, prodrugs, stereoisomers, or tautomers thereof, or combinations thereof. In another embodiment, is a method of manufacturing a composition comprising *Trametes versicolor* or a pharmaceutically acceptable salt, hydrate, solvate, prodrug, stereoisomer, or tautomer thereof, or a combination thereof. The method may include growing a mushroom on a substrate, separating the mushroom mycelium from a fruitbody and the substrate, incubating the mycelium with a solvent, forming a solution, extracting an aqueous fraction from the solution, extracting a solid fraction from the solution. The substrate may be one or more of rice, oat, straw, or sawdust.

In one embodiment, the mushroom may be grown on a substrate at about 15° C. to about 30° C. for about 20 to about 120 days, at about 10° C. to about 40° C. for about 10 to about 100 days, at about 20° C. to about 30° C. for about 15 to about 60 days, or at about 15° C. to about 30° C. for about 1 to about 100 days, at about 15° C. to about 30° C. for about 30 to about 50 days, at about 20° C. to about 30° C. for about 30 to about 50 days. The mushroom may be grown on a substrate at about 20° C. to about 25° C. for about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, about 30 days, about 31 days, about 32 days, about 33 days, about 34 days, about 35 days, about 36 days, about 37 days, about 38 days, about 39 days, about 40 days, about 41 days, about 42 days, about 43 days, about 44 days, about 45 days, about 46 days, about 47 days, about 48 days, about 49 days, about 50 days, about 51 days, about 52 days, about 53 days, about 54 days, about 55 days, about 56 days, about 57 days, about 58 days, about 59 days, about 60 days, about 61 days, about 62 days, about 63 days, about 64 days, about 65 days, about 66 days, about 67 days, about 68 days, about 69 days, about 70 days, about 71 days, about 72 days, about 73 days, about 74 days, about 75 days, about 76 days, about 77 days, about 78 days, about 79 days, about 80 days, about 81 days, about 82 days, about 83 days, about 84 days, about 85 days, about 86 days, about 87 days, about 88 days, about 89 days, about 90 days, about 91 days, about 92 days, about 93 days, about 94 days, about 95 days, about 96 days, about 97 days, about 98 days, about 99 days, about 100 days, about 101 days, about 102 days, about 103 days, about 104 days, about 105 days, about 106 days, about 107 days, about 108 days, about 109 days, about 110 days, about 111 days, about 112 days, about 113 days, about 114 days, about 115 days, about 116 days, about 117 days, about 118 days, about 119 days, or about 120 days. In some embodiments, the solvent is cold water.

The mycelium as described herein may be flash frozen at about −18° C. The frozen mycelium may be freeze-dried and ground into a powder. The mycelium may be freeze-dried at a pressure of about 500 mbar to about 3,000 mbar, about 1,000 mbar to about 3,000 mbar, about 1,000 mbar to about 2,000 mbar, about 1,500 mbar to about 2,000 mbar, or about 1,500 mbar to about 3,000 mbar. Heat of about 60° C. to 100° C., about 65° C. to 100° C., about 70° C. to 100° C., about 75° C. to 100° C., about 75° C. to 95° C., about 75° C. to 90° C., about 75° C. to 85° C., or about 75° C. to 80° C. may be applied to the mycelium. The freezer-dried mycelium may be milled to a fineness of about 50 microns to about 1,000 microns, about 100 microns to about 1,000 microns, about 150 microns to about 1,000 microns, about 160 microns to about 1,000 microns, about 170 microns to about 1,000 microns, about 180 microns to about 1,000 microns, about 190 microns to about 1,000 microns, about 200 microns to about 1,000 microns, about 500 microns to about 1,000 microns, about 50 microns to about 950 microns, about 100 microns to about 950 microns, about 150 microns to about 950 microns, about 160 microns to about 950 microns, about 170 microns to about 950 microns, about 180 microns to about 950 microns, about 190 microns to about 950 microns, about 200 microns to about 950 microns, about 500 microns to about 950 microns, about 50 microns to about 900 microns, about 100 microns to about 900 microns, about 150 microns to about 900 microns, about 160 microns to about 900 microns, about 170 microns to about 900 microns, about 180 microns to about 900 microns, about 190 microns to about 900 microns, about 200 microns to about 900 microns, about 500 microns to about 900 microns, about microns to about 850 microns, about 100 microns to about 850 microns, about 150 microns to about 850 microns, about 160 microns to about 850 microns, about 170 microns to about 850 microns, about 180 microns to about 850 microns, about 190 microns to about 850 microns, about 200 microns to about 850 microns, about 500 microns to about 850 microns, about 50 microns to about 800 microns, about 100 microns to about 800 microns, about 150 microns to about 800 microns, about 160 microns to about 800 microns, about 170 microns to about 800 microns, about 180 microns to about 800 microns, about 190 microns to about 800 microns, about 200 microns to about 800 microns, about 500 microns to about 800 microns, about 50 microns to about 750 microns, about 100 microns to about 750 microns, about 150 microns to about 750 microns, about 160 microns to about 750 microns, about 170 microns to about 750 microns, about 180 microns to about 750 microns, about 190 microns to about 750 microns, about 200 microns to about 750 microns, about 500 microns to about 750 microns, about 50 microns to about 500 microns, about 100 microns to about 500 microns, about 150 microns to about 500 microns, about 160 microns to about 500 microns, about 170 microns to about 500 microns, about 180 microns to about 500 microns, about 190 microns to about 500 microns, about 200 microns to about 500 microns, about 500 microns to about 600 microns. The mycelium may be milled using a 20-80 standard mesh. The milled mycelium can be filled into capsules, made into tablets, tinctures, or further used as a base for a medicinal product effective as an antimicrobial and/or for potentiating a host mediated response.

The method may include incubating a powder of the mushroom mycelium and/or fruit body mixture in a solvent, forming a solution. The method may further comprise extracting aqueous compounds from the solution in a buffered solution, extracting non-aqueous compounds from the solution in an ethanol solution, and extracting a solid fraction from the solution. The ethanol solution may be about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% ethanol. In some embodiments, the solid fraction may include insoluble fractions of the powder of the mushroom mycelium and/or fruit body mixture.

In some embodiments, the mushroom mycelium and/or fruit body mixture may include *Agaricus brasiliensis* f. *blazei*, *Cordyceps militaris*, *Flammulina velutipes*, *Fomes fomentarius*, *Fomitopsis officinalis*, *Ganoderma applanatum*, *Ganoderma lucidum* s.l., *Ganoderma oregonense* s.l., *Grifola frondosa*, *Hericium erinaceus*, *Inonotus obliquus*, *Lentinula edodes*, *Phellinus linteus*, *Piptoporus betulinus*, *Pleurotus ostreatus*, *Schizophyllum commune*, and/or *Trametes versicolor* or a pharmaceutically acceptable salt, hydrate, solvate, prodrug, stereoisomer, or tautomer thereof, or a combination thereof.

It will be apparent to one of ordinary skill in the relevant art that suitable modifications and adaptations to the compositions, formulations, methods, processes, and applications described herein can be made without departing from the scope of any embodiments or aspects thereof. The compositions and methods provided are exemplary and are not intended to limit the scope of any of the specified embodiments. All of the various embodiments, aspects, and options disclosed herein can be combined in any variations or iterations. The scope of the compositions, formulations, methods, and processes described herein include all actual or potential combinations of embodiments, aspects, options, examples, and preferences herein described. The exemplary compositions and formulations described herein may omit any component, substitute any component disclosed herein, or include any component disclosed elsewhere herein. The ratios of the mass of any component of any of the compositions or formulations disclosed herein to the mass of any other component in the formulation or to the total mass of the other components in the formulation are hereby disclosed as if they were expressly disclosed. Should the meaning of any terms in any of the patents or publications incorporated by reference conflict with the meaning of the terms used in this disclosure, the meanings of the terms or phrases in this disclosure are controlling. Furthermore, the foregoing discussion discloses and describes merely exemplary embodiments. All patents and publications cited herein are incorporated by reference herein for the specific teachings thereof.

EXAMPLES

Example 1

Reagents

Roswell Park Memorial Institute 1640 medium, penicillin-streptomycin 100×, interleukin-2 (IL-2), phosphate-buffered saline, and lipopolysaccharide (LPS) from *Salmonella enterica* were purchased from Sigma-Aldrich Co. (St Louis, MO, USA). CD69 fluorescein isothiocyanate, CD56 phycoerythrin, CD3 peridinin chlorophyll protein, and heparin Vacutainer tubes were purchased from Becton-Dickinson (Franklin Lakes, NJ, USA). Customized Bio-Plex Pro™ human cytokine arrays were purchased from Bio-Rad Laboratories Inc. (Hercules, CA, USA).

Figure 1:
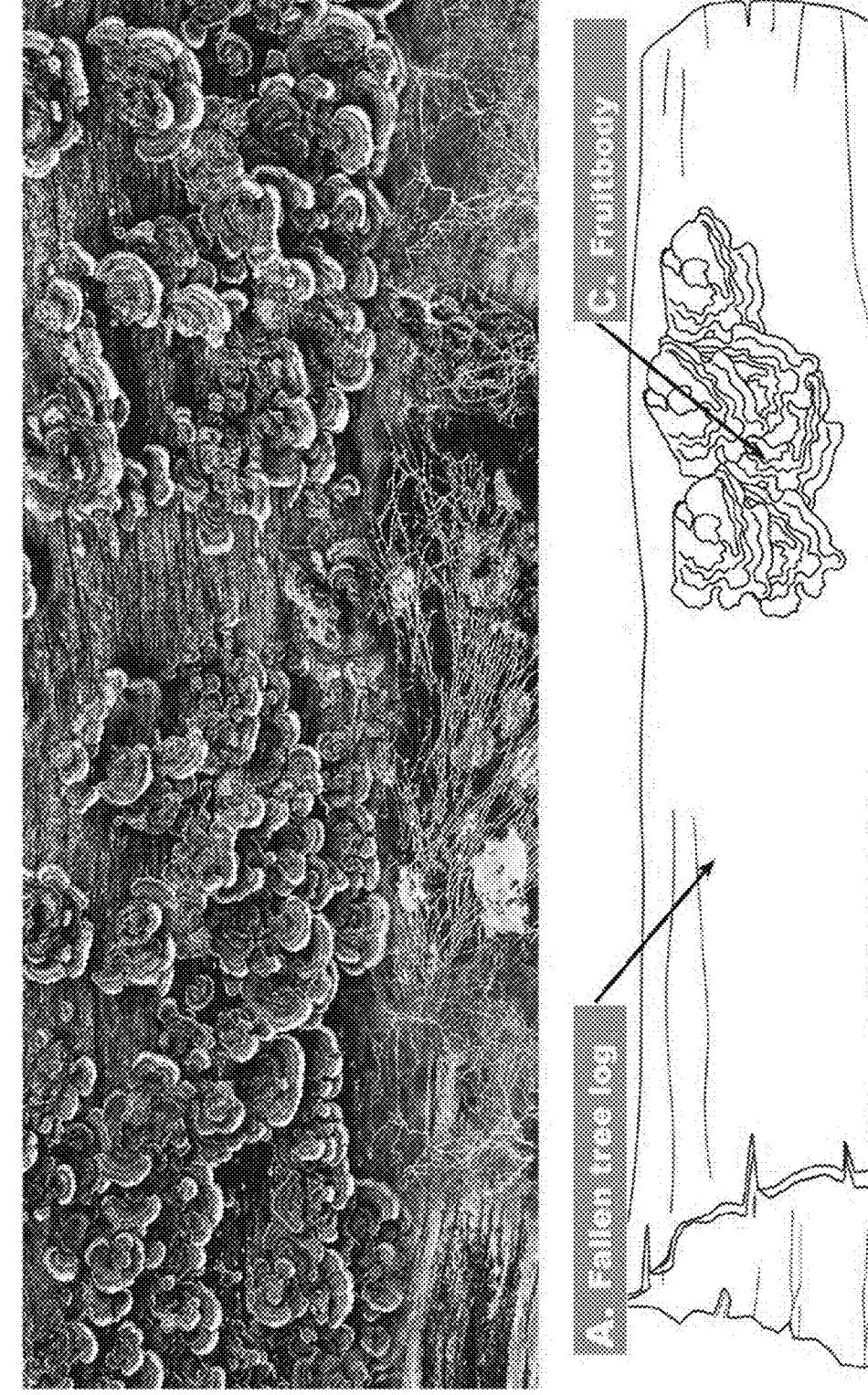
FIG. 1 shows decomposition of a fallen tree log by *Trametes versicolor* (Tv). Arrow A. Fallen tree log, presenting fresh organic plant matter. Arrow B. Tv mycelium is growing inside the log, decomposing the plant biomass by fermentation, in a highly dynamic exchange of solubilized nutrients from the tree log, resulting from secreted fungal enzymes, combined with anti-microbial defense compounds to protect the mycelial territory. Arrow C. Fruitbodies serve to spread the spores of the Tv mushrooms, and have a narrower chemical composition, focused on beta-glucans, spores, attractants to animals that may eat and transport the spores, and protectants to protect the fruitbodies from bacteria and other fungi.
Figures 2A, 2B:
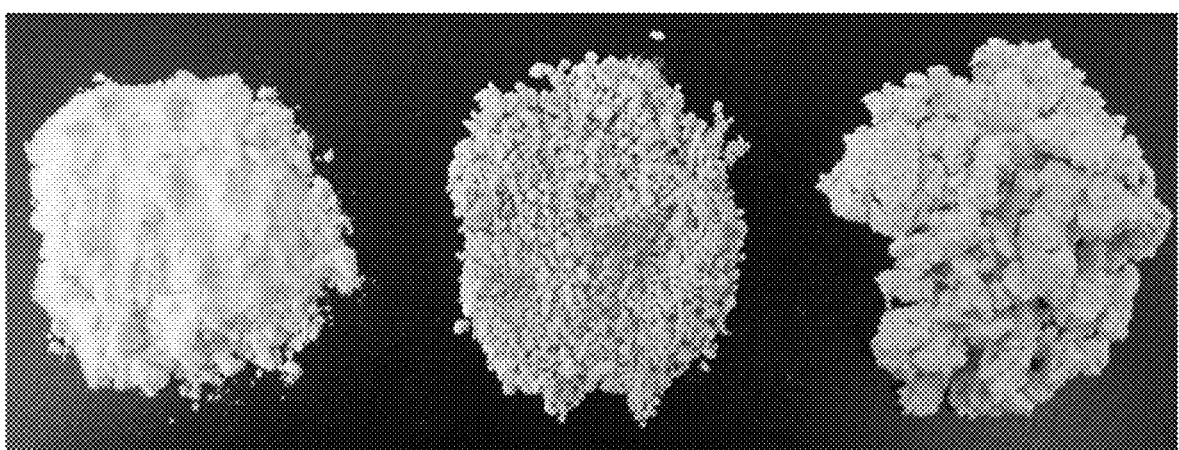
FIG. 2A and FIG. 2B show *Trametes versicolor* (Tv) used as an experimental model to isolate and compare the mycelium and its fermented substrate.

*Trametes versicolor* (Turkey Tail) Culture and Separation of Mycelial and Fermented Substrate The mycelial culture work and sample processing was performed at Fungi Perfecti LLC, following a three-step process of substrate preparation, mycelial culturing, and sample separation (FIG. 2A). Certified organic rice flour (Azure Farms, Dufur, Oregon, USA) mixed with water to form a paste and sterilized by autoclaving at 1 bar for 60 min. This resulted in a solid biscuit-like disc of rice grain media (0.4-0.45 g/g water content; aw 0.99). This material constituted the initial substrate (IS). A Petri dish containing 60 g (dry mass) of the milled and sterilized rice flour was inoculated with 50 mg of *Trametes versicolor* agar media spawn. The resulting inoculated media disc solid substrate fermentation microcosm was stored at 20-24° C. for 42 days in a class 1000 clean room. The *Trametes versicolor* mycelium spread radially over the growth substrate, preferentially developing biomass on the surface of the substrate where gas exchange was highest. Mycelium was separated mechanically by removing the surface mycelium from the underlying substrate with a scalpel.

Preparation of Mycelium and Substrate for In Vitro Testing

The three powders were handled in the following manner: (1) Liquid extraction using phosphate-buffered saline (PBS) and referred to as the aqueous fraction; (2) Harvesting the non-aqueous, solid fractions left after aqueous extractions were completed, and passing them through homogenization spin columns (QIAshredder, Qiagen, Hercules, CA). The aqueous fractions were filtered through a 0.22-μm filter before adding to cell cultures. The solid fractions were not filtered through a 0.22-μm filter. This provided two "test products/fractions" from each product, namely the aqueous fraction and the solid fraction. From each fraction, serial dilutions were made in phosphate-buffered saline.

Dry Weight Determinations of Aqueous Extracts

The aqueous extracts were produced by cold-water extraction, and not using heat or pressure. This is in contrast to other types of fungal extracts and teas, where heat and sometimes pressure is applied to produce the extract. Examples include the use of batch reactors and subcritical water extraction, with heat up to 300° C., to produce mushroom extracts. The data graphs show the biological activities per gram starting material. However, in order to understand the relative contributions from aqueous constituents, dry weight assessments were performed for the aqueous fractions. From each of the three powders, a 100 g/L suspension was prepared in distilled $H_2O$. The powder was allowed to hydrate, and water-soluble compounds were extracted for 1 h under gentle agitation. Solids were precipitated by centrifugation in conical polypropylene vials for 10 min at 400 g. The liquid fraction was harvested, passed through a 0.22-μm cellulose acetate filter, and dried at 100° C. The weights of the filtrates were 45 mg/g (4.5% w/w) for the initial substrate, 110 mg/g (11% w/w) for the fermented substrate, and 120 mg/g (12% w/w) for the mycelium.

Immune Cell Activation

Peripheral venous blood was drawn from three healthy human donors upon written informed consent, as approval by the Sky Lakes Medical Center Institutional Review Board, Federalwide Assurance 2603. The blood was drawn into heparin vacutainer vials, and the peripheral blood mononuclear cells (PBMC) isolated using Lympholyte Poly (Cedarlane Labs, Burlington, Ontario, CA) by centrifugation for 35 min at 450 g. The PBMC were washed twice in PBS, counted, and the density adjusted to establish cultures with a cell density at $10^6$/mL, using Roswell Park Memorial Institute 1640 medium containing penicillin—streptomycin and 10% heat-inactivated fetal bovine serum (Gibco, Thermo Fisher Scientific, Asheville, NC).

Serial dilutions of products or LPS were added to cultures at a volume of 20 μL, and cultures were then incubated at 37° C., 5% $CO_2$ for 24 h. The highly inflammatory LPS from *Salmonella enterica* was used as a positive control for immune-cell activation at a dose of 10 ng/mL. In parallel, IL-2 was used as a positive control for natural killer (NK)-cell activation, at a concentration of 100 IU/mL. Untreated negative control cultures consisted of PBMC exposed to phosphate-buffered saline in the absence of test products. All treatments, including each dose of test product and each positive and negative control, were tested in triplicate. After 24 h, blood cells were isolated from each culture well and stained for 10 min with fluorochrome-labeled antibodies at the recommended concentration. PBMC were then fixed using 0.5% formalin. The fluorescence intensities for CD3, CD56, and CD69 were measured by flow cytometry, using an Attune acoustic-focusing flow cytometer (Thermo Fisher Scientific).

During data analysis, gating on forward and side scatter facilitated evaluation of the levels of CD69 expression on lymphocyte and monocyte subsets. The lymphocyte subpopulation was further analyzed for CD69 expression on CD3+ T lymphocytes, CD3+ CD56+ NKT lymphocytes, and CD3− CD56+ NK cells.

Production of Cytokines, Chemokines, and Growth Factors

After 24 h of incubation, the supernatants were harvested from the PBMC cultures described above. Levels of 10 cytokines and chemokines were quantified (IL-1ra, IL-2, IL-4, IL-6, IL-8 (CXCL8), IL-10, interferon gamma (IFN-γ), tumor necrosis factor alpha (TNF-α), MIP-1α (CCL3), and G-CSF) using Bio-Plex Pro™ multiplex immunoassays (Bio-Rad Laboratories, Hercules, CA) and utilizing xMAP technology (Luminex, Austin, TX, USA).

Statistical Analysis

Average and standard deviation for each data set was calculated using Microsoft Excel. Statistical analysis of in vitro data was performed using the 2-tailed, independent t-test. Statistical significance was set at P<0.05, and a high level of significance at P<0.01.

Example 2

Induction of the CD69 Activation Marker on Immune Cell Subsets

Figure 3A:
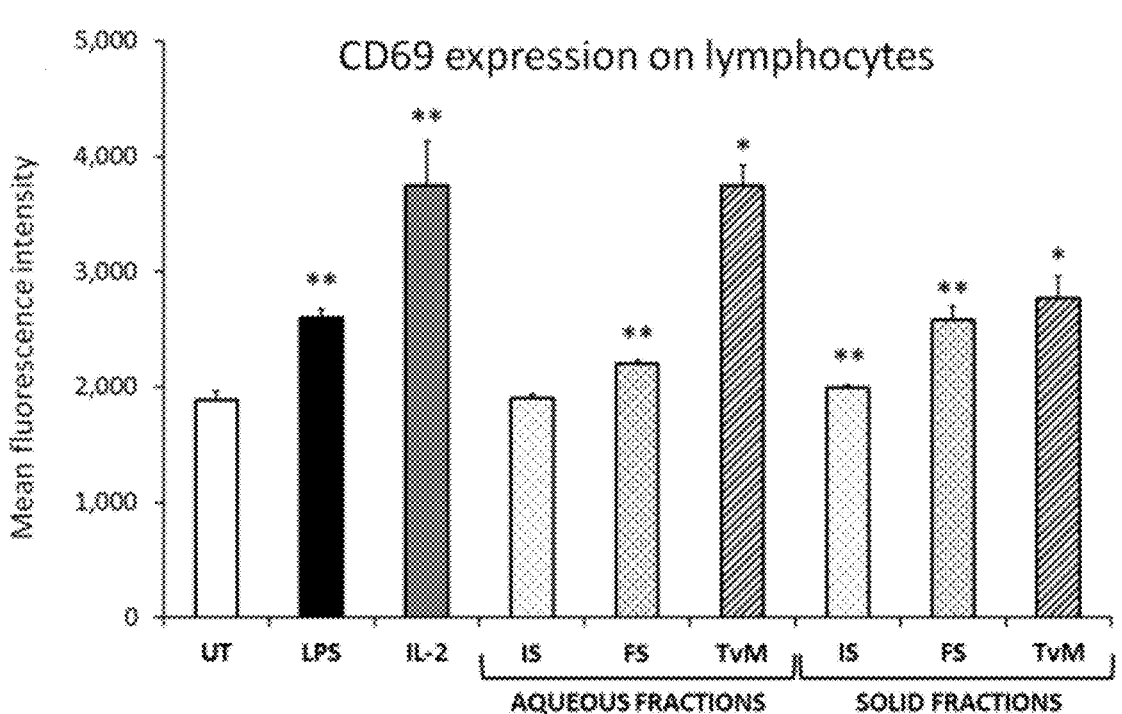
FIG. 3A and FIG. 3B show the induction of the CD69 cellular activation marker on lymphocyte (FIG. 3A) and monocyte (FIG. 3B) subsets in human PBMC cultures. The PBMC cultures were treated for 24 h in the presence of the aqueous versus solid fractions of initial substrate (IS), fermented substrate (FS), and *Trametes versicolor* mycelium (TvM). Data are shown for the highest dose tested (2 mg/mL), where the dose represents the amount of starting material used to produce a given fraction. Data are presented as mean±standard deviation of the mean fluorescence intensities in triplicate cultures and represents one of three separate experiments using PBMC cells from three different healthy human donors. Positive controls included lipopolysaccharide (LPS, 10 ng/mL) and Interleukin-2 (IL-2, 100 IU/mL). Statistical significance is indicated as * for $P<0.05$ and ** for $P<0.01$.
Figure 3B:
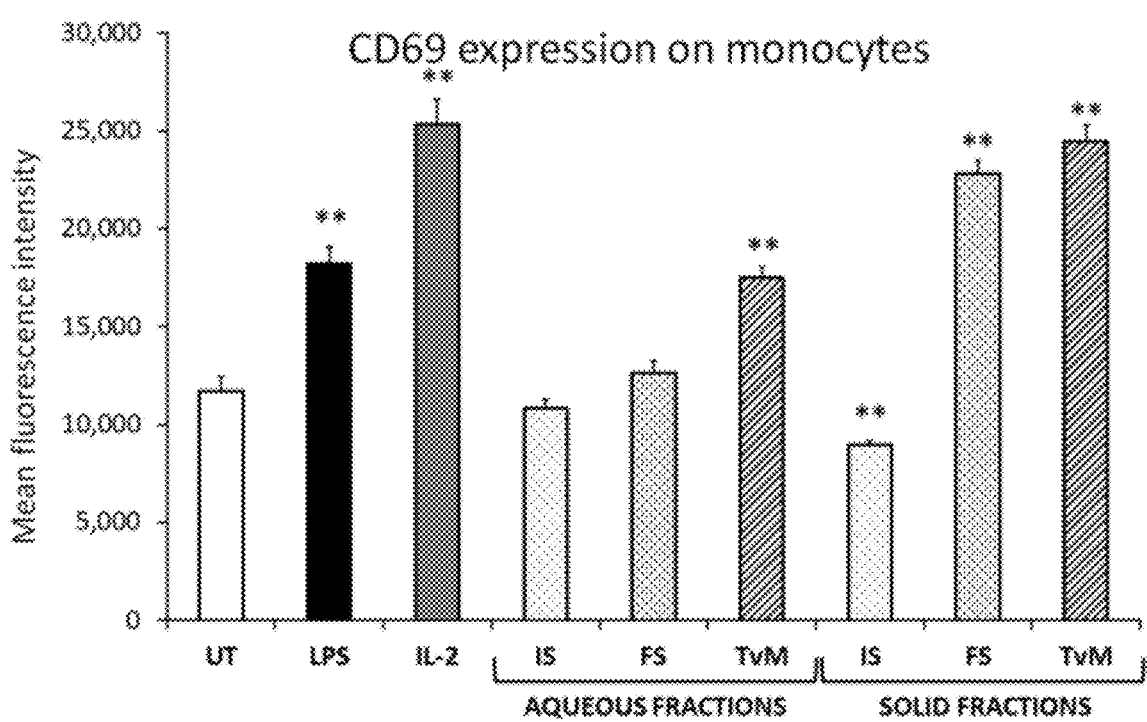

The cell surface expression of the early activation marker CD69 was measured on peripheral blood mononuclear cells (PBMC), after 24 h incubation in the absence or presence of initial substrate (IS), fermented substrate (FS), and *Trametes versicolor* mycelium (TvM). Representative results from one blood donor are shown in FIGS. 3 and 4. During flow cytometric data analysis, gating on the physical characteristics of the cell subsets, allowed analysis on lymphocytes versus monocytes (FIG. 3A and FIG. 3B). The aqueous fraction of IS showed no effect on CD69 expression (FIG. 3A). The solid fraction showed a minor increase in CD69 expression on lymphocytes, and a significant suppression of CD69 expression on monocytes (P<0.001) (FIG. 3B).

The induction of CD69 on human lymphocytes by the aqueous and solid fractions of FS showed higher CD69 induction by the solid fraction than the induction seen by the aqueous fraction. The difference in CD69 induction by the aqueous and solid fractions of FS was statistically significant (P<0.03).

The treatment of human lymphocytes with both the aqueous and the solid fractions of TvM resulted in a robust and statistically significant increase of the CD69 marker, indicating immune cell activation (FIG. 3A). The induction of CD69 on human lymphocytes by the TvM aqueous fraction was more robust than the induction seen by the TvM solid fraction (FIG. 3A), where the difference between the TvM aqueous and solid fractions was statistically significant (P<0.02).

In contrast, the induction of CD69 on human monocytes by the TvM solid fraction was more robust than the induction seen by the TvM aqueous fraction (FIG. 3B), where the difference between the TvM aqueous and solid fractions was highly significant (P<0.001).

The lymphocyte subset was further analyzed for expression of the CD69 activation marker of CD3+ T cells, CD3+ CD56+ NKT lymphocytes, and CD3− CD56+ Natural Killer (NK) cells (FIG. 4). It was found that the aqueous extract from TvM triggered a very potent activation of NKT cells (FIG. 4C), and a more moderate activation of T cells and NK cells (FIGS. 4A and E). The aqueous extract of the fermented substrate only induced minor increases in CD69 on all three cell types, and the aqueous extract of the initial substrate did not induce CD69 on any of the three cell types (FIG. 4A, C, E).

Figure 4A:
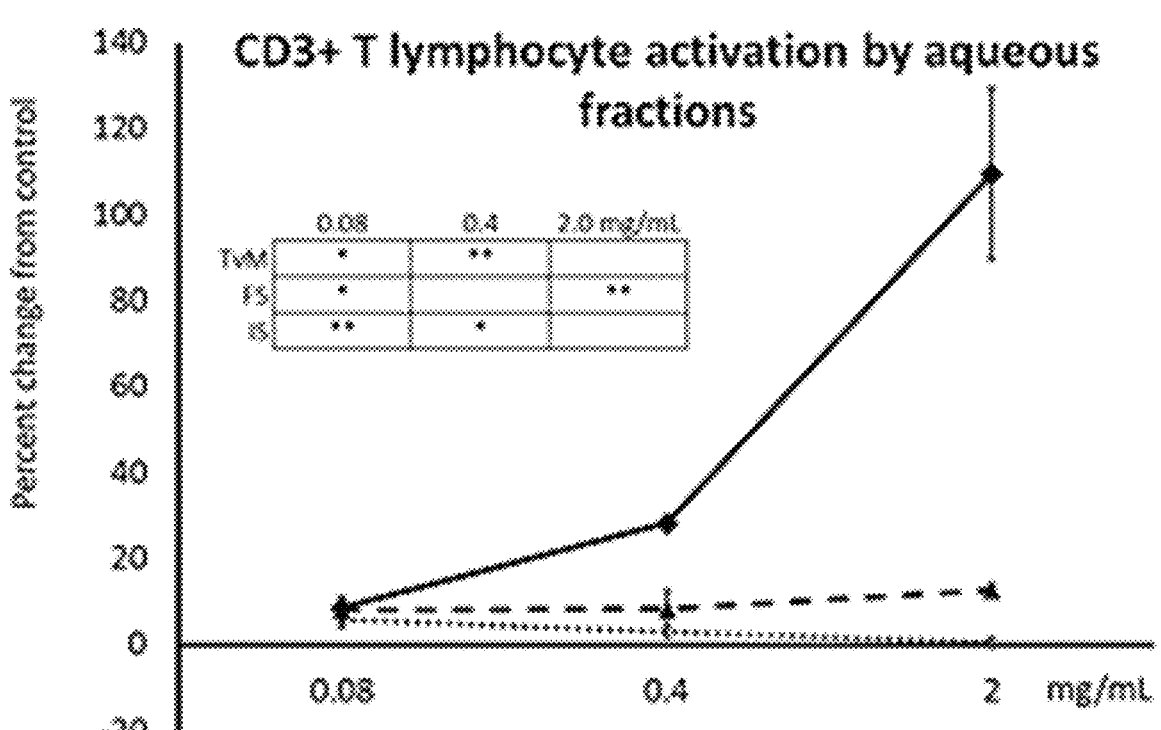
FIG. 4A-F show the induction of the CD69 cellular activation marker on immune cell subsets in human PBMC cultures. The PBMC cultures were treated for 24 h in the presence of serial dilutions of *Trametes versicolor* mycelium (TvM), fermented substrate (FS), or initial substrate (IS). The percent change when compared to untreated control cultures is shown for T lymphocytes (FIG. 4A and FIG. 4B), NKT cells (FIG. 4C and FIG. 4D), and NK cells (FIG. 4E and FIG. 4F). The effects of aqueous extracts are shown in FIG. 4A, FIG. 4C, and FIG. 4E, and the effects of the solid fractions are shown in FIG. 4B, FIG. 4D, and FIG. 4F. Data are shown for three doses tested (0.08, 0.4, and 2 mg/mL), where the doses represent the amount of starting material used to produce a given fraction. Data are presented as mean±standard deviation of the percent change seen in triplicate cultures and represents one of three separate experiments using PBMC cells from three different healthy human donors. Positive controls included LPS and IL-2. The mean±standard deviation percent change induced by LPS were 19±2.1% for T lymphocytes, 54±8.3% for NKT cells, and 114±10% for NK cells. The mean±standard deviation percent change induced by IL-2 were 39±0.9% for T lymphocytes, 150±25% for NKT cells, and 446±60.0% for NK cells. Inserted tables: Statistical significance is indicated as * for $P<0.05$ and ** for $P<0.01$.
Figure 4B:
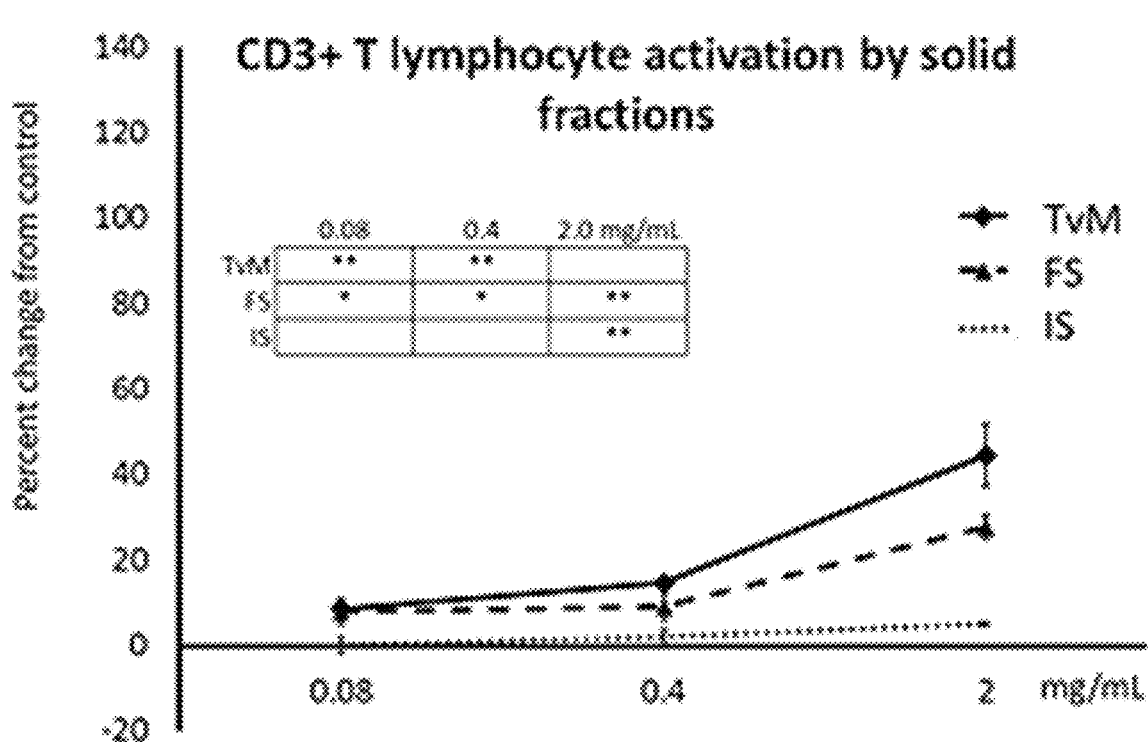
Figure 4C:
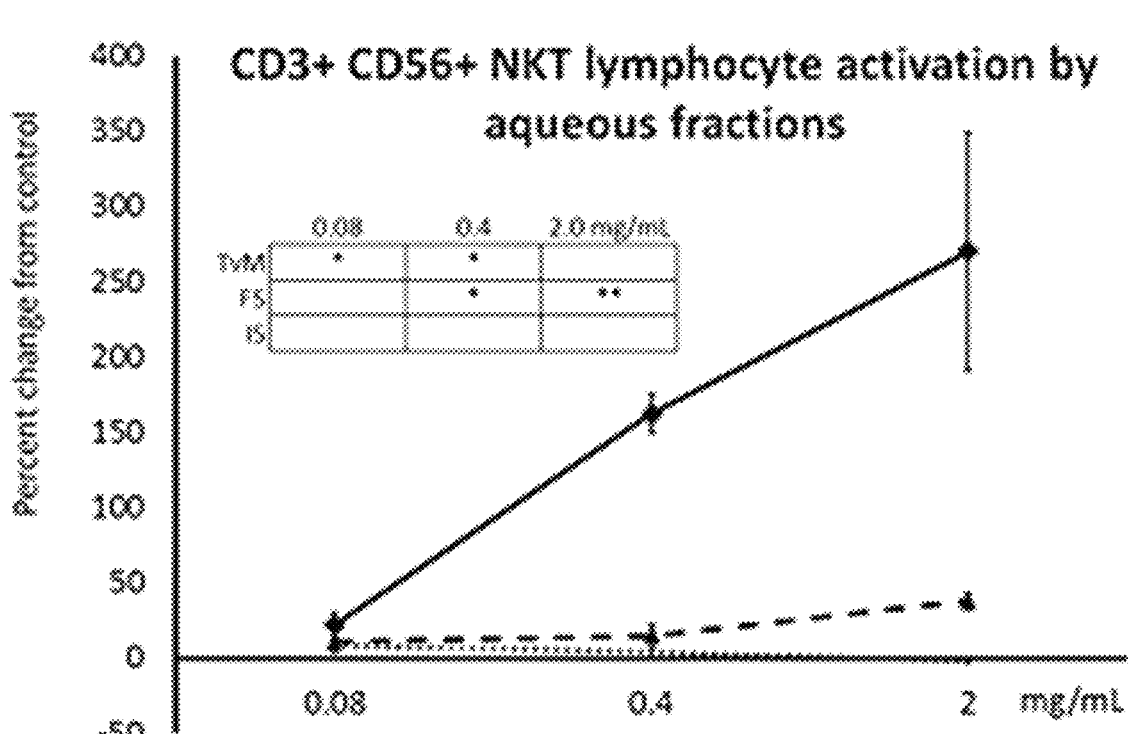
Figure 4D:
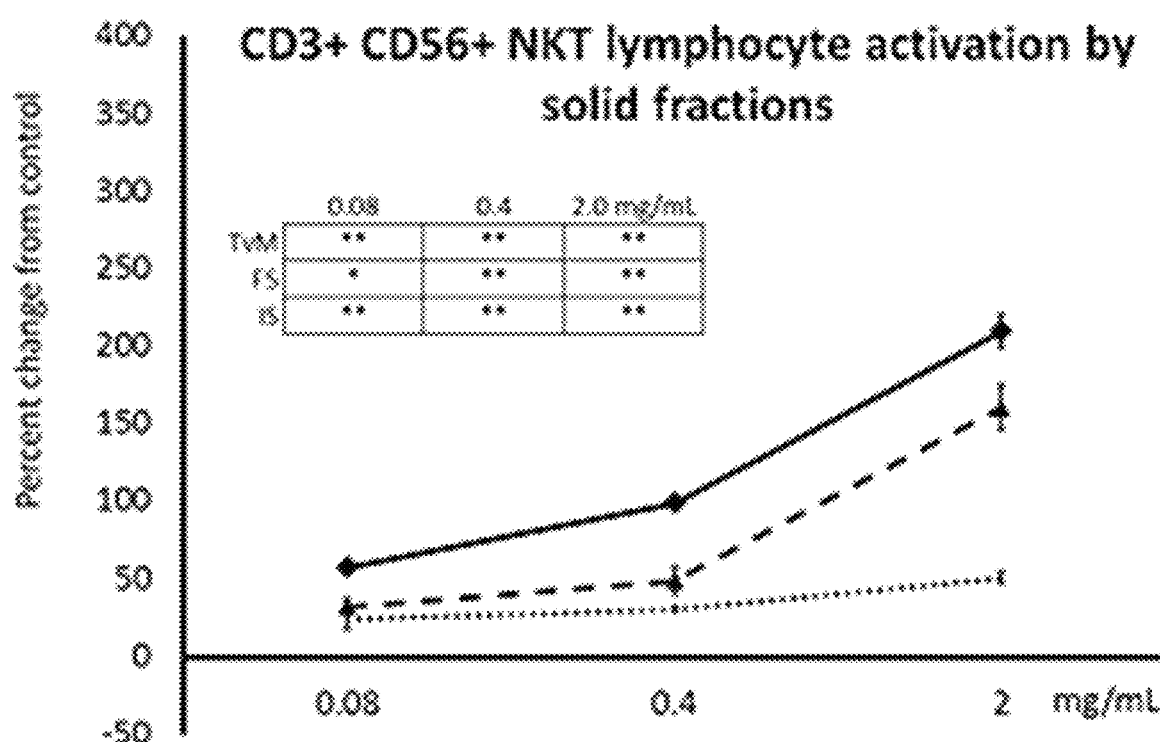
Figure 4E:
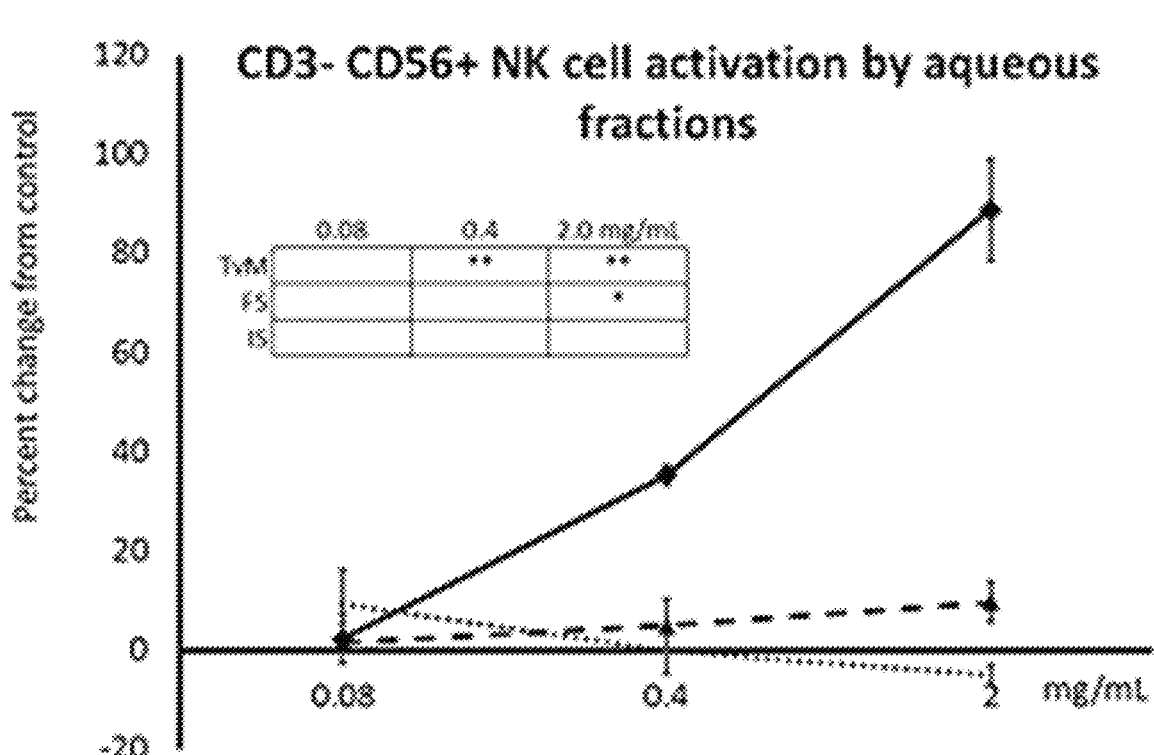
Figure 4F:
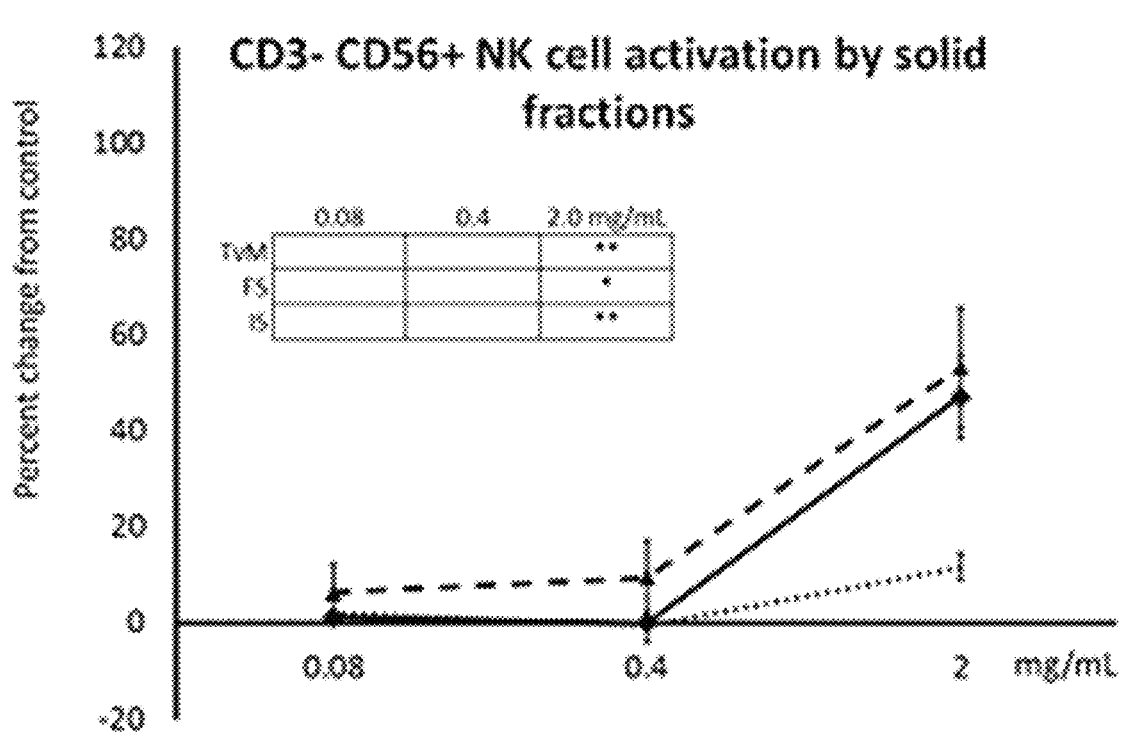

In contrast, the solid fractions of TvM and FS induced comparable levels of cellular activation, as measured by increased CD69 expression (FIG. 4B, D, F). The activation was not as strong as what was seen for the aqueous extract of the mycelium but was stronger than the cell activation by the aqueous extract of the fermented substrate. The solid fraction from the initial substrate showed minor activation of NK cells and NKT cells (FIG. 4D, F).

Overall, the TvM-mediated induction of CD69 expression on lymphocytes and monocytes was triggered by both aqueous and solid fractions, however, the CD69 expression on lymphocytes was more robust when cells were treated with the aqueous fraction than the solid fraction, with the aqueous fraction comparable to the induction caused by LPS. Given that the aqueous fraction contained almost 10 times less material than the solid fraction, this further demonstrates the potency of the aqueous compounds in the mycelium. For monocytes, this was reversed, where the solid fraction triggered a stronger CD69 expression than the aqueous fraction of the TvM.

Increased Production of Pro-Inflammatory, Immune-Activating Cytokines

Figure 5A:
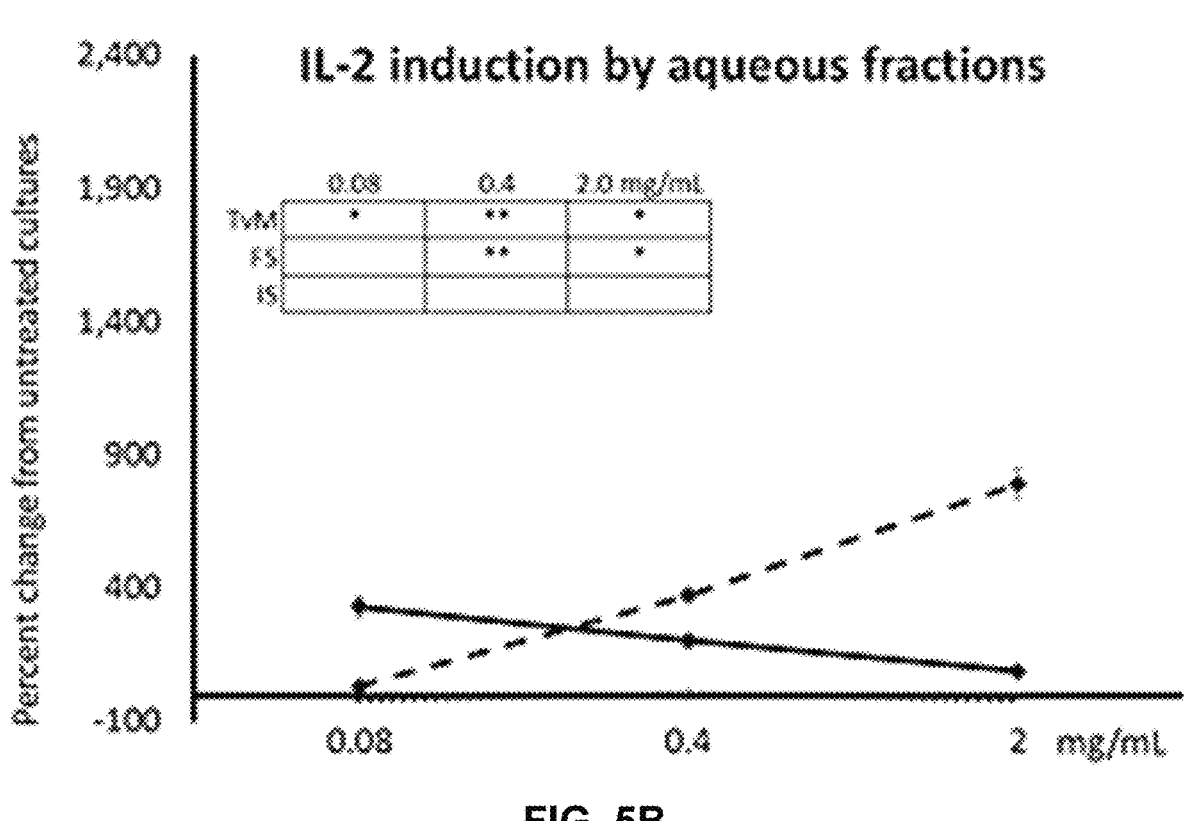
FIG. 5A-D show changes in levels of the cytokines Interleukin-2 (IL-2) and Interleukin-6 (IL-6) in supernatants from human PBMC cultures. The PBMC were cultured for 24 h in the presence of serial dilutions on *Trametes versicolor* mycelium (TvM), fermented substrate (FS), or initial substrate (IS). The effects on IL-2 and IL-6, cytokines involved in immune activation, of aqueous extracts shown in FIG. 5A and FIG. 5C, and of the solid fractions are shown in FIG. 5B and FIG. 5D. Data are shown for three doses (0.08, 0.4, and 2 mg/mL), where the doses represent the amount of starting material used to produce a given fraction. Data are presented as mean±standard deviation of the percent change seen in triplicate cultures and represents one of three separate experiments using PBMC cells from three different healthy human donors. Inserted tables: Statistical significance is indicated as * for $P<0.05$ and ** for $P<0.01$.
Figure 5B:
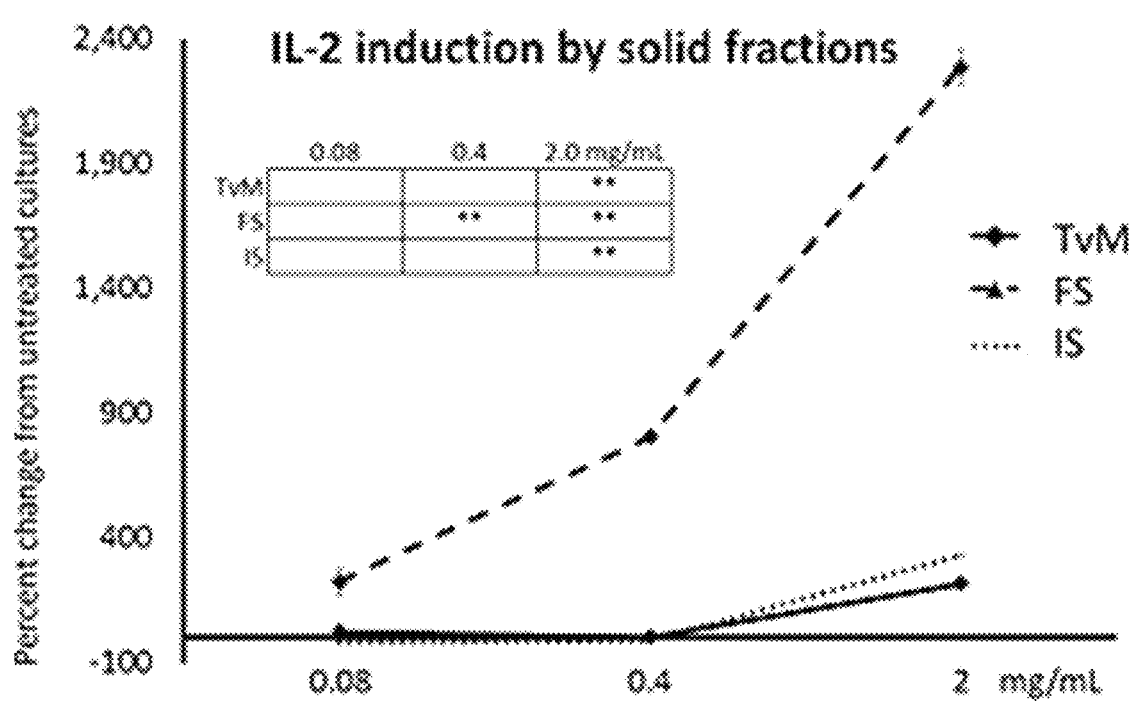
Figure 5C:
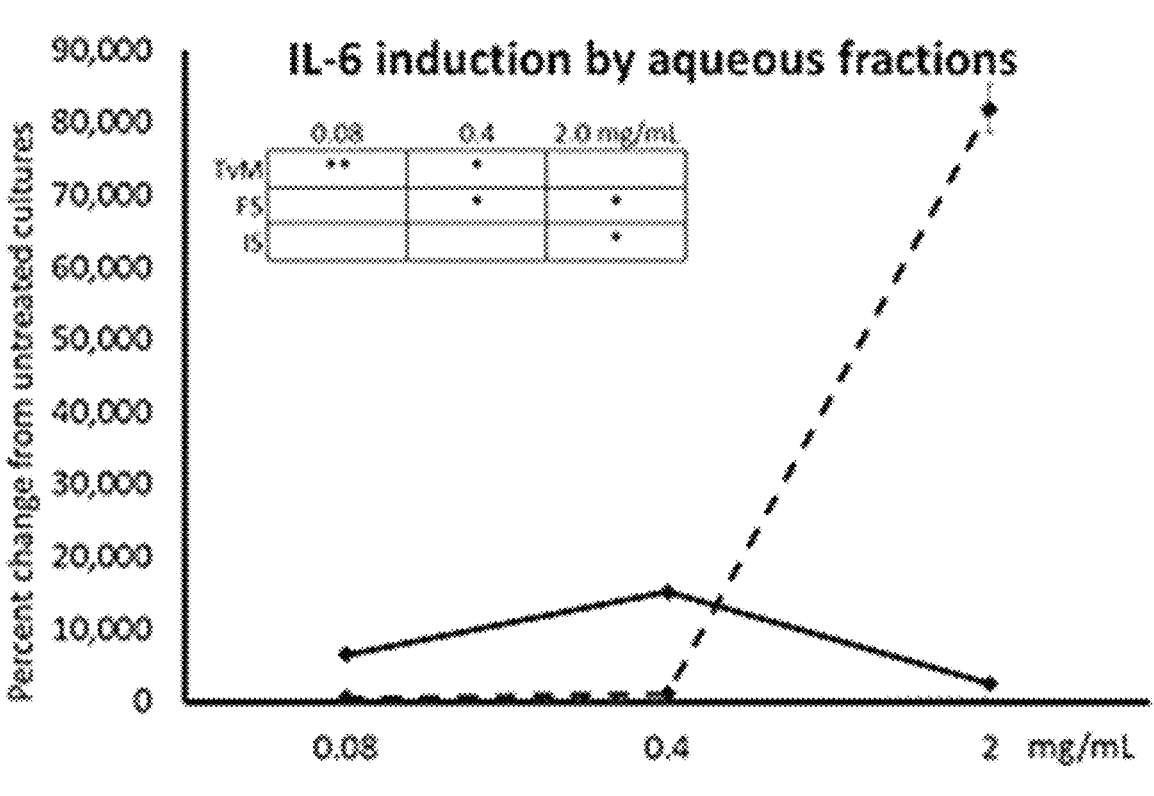
Figure 5D:
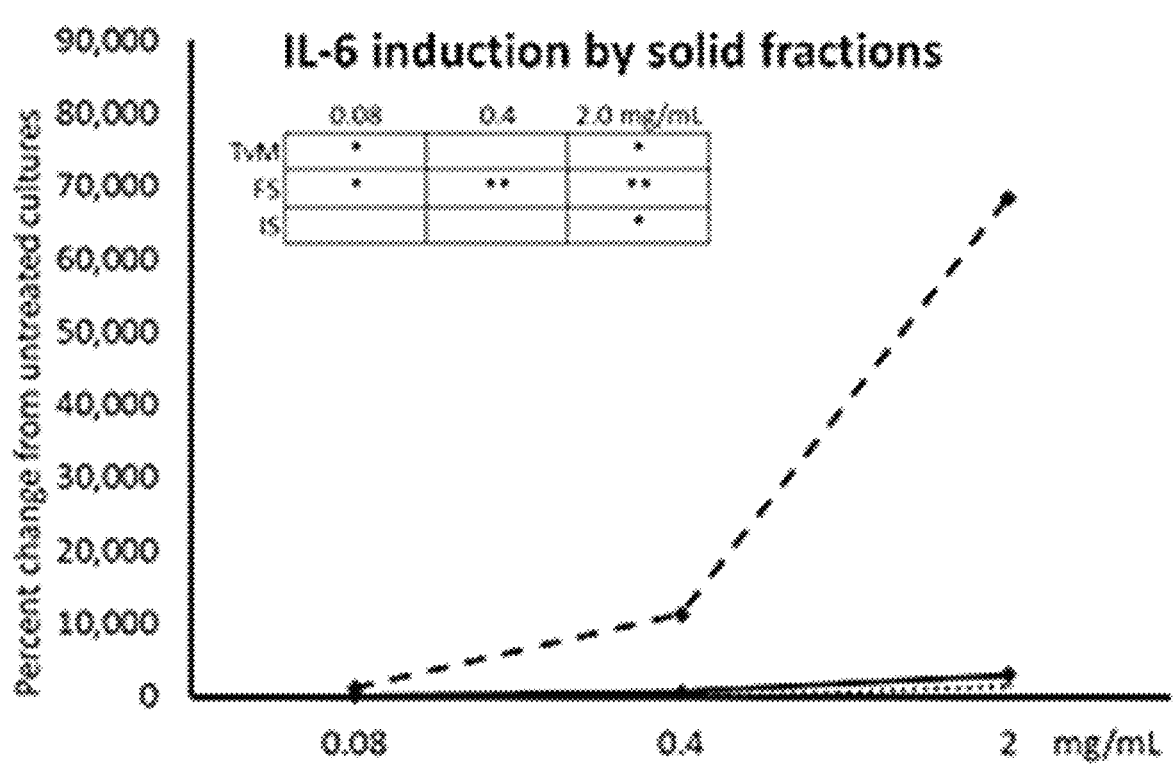

The culture supernatants from the PBMC cultures were tested for the levels of two cytokines involved in immune cell activation, Interleukin-2 (IL-2) and Interleukin-6 (IL-6). Representative results from one blood donor are shown in FIG. 5A-D. Both the aqueous and the solid fractions of the fermented substrate (FS) induced robust increases in IL-2 and IL-6 levels (FIG. 5A-D). The aqueous fraction of *Trametes versicolor* mycelium (TvM) also induced IL-2 and IL-6 but was more potent at doing so at lower doses (FIG. 5A, C). The solid fraction of TvM had mild effects on IL-2 and IL-6 production in the cultures, and the induction was comparable to the solid fraction of the initial substrate (FIG. 5B, D). The aqueous fraction of the initial substrate did not have any effect on IL-2 or IL-6 induction (FIG. 5A, C).

The cytokine induction by aqueous and insoluble compounds in the FS was seen in the absence of CD69 upregulation, suggesting activation via alternate pathways that may involve upregulation of the Interleukin-2 receptor CD25 (i.e. increased cell proliferation).

Increased Anti-Viral Cytokine Production

Figure 6A:
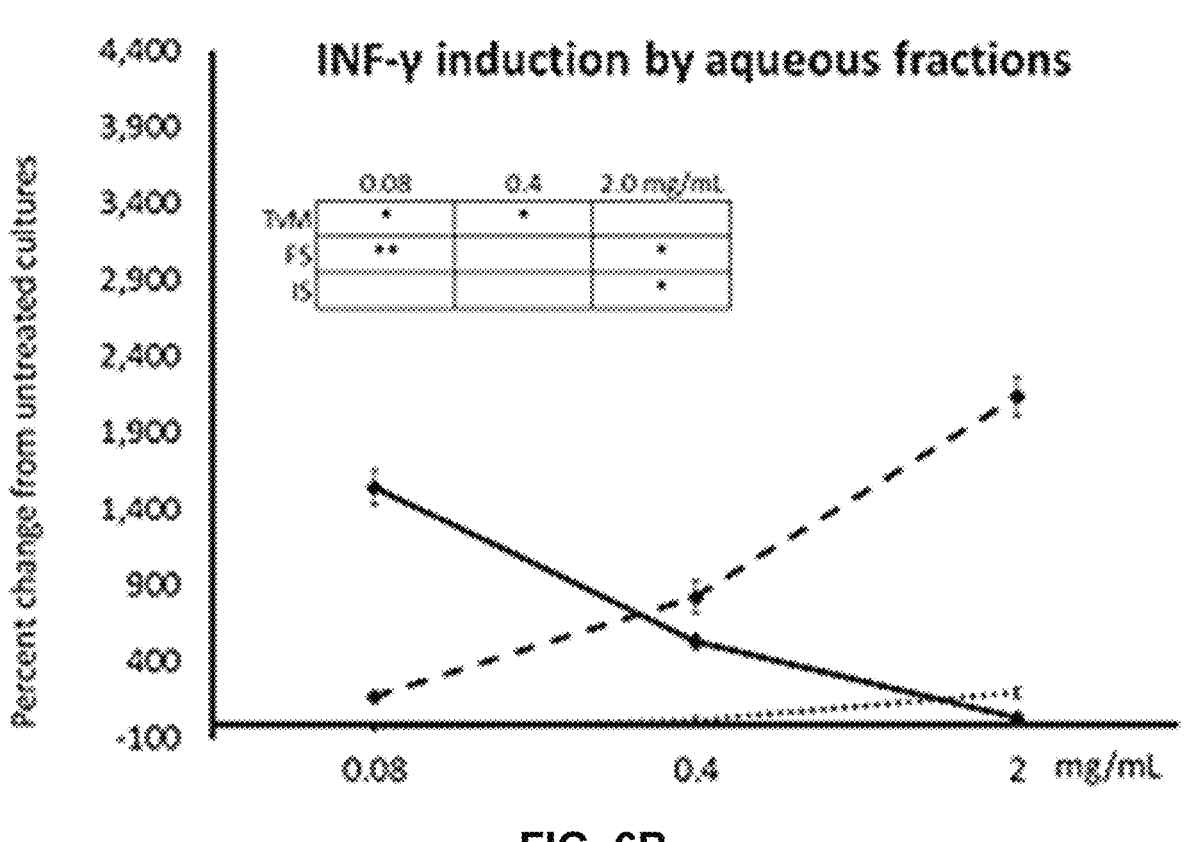
FIG. 6A-D show changes in levels of the cytokines Interferon-gamma (IFN-γ) and Macrophage Inflammatory Protein-1-alpha (MIP-1α) in supernatants from human PBMC cultures. The PBMC were cultured for 24 h in the presence of serial dilutions of *Trametes versicolor* mycelium (TvM), fermented substrate (FS), or initial substrate (IS). The effects on IFN-γ and MIP-1α, cytokines involved in anti-viral immune defense activity, of aqueous extracts shown in FIG. 6A and FIG. 6C, and of the solid fractions are shown in FIG. 6B and FIG. 6D. Data are shown for three doses (0.08, 0.4, and 2 mg/mL), where the doses represent the amount of starting material used to produce a given fraction. Data are presented as mean±standard deviation of the percent change seen in triplicate cultures and represents one of three separate experiments using PBMC cells from three different healthy human donors. Inserted tables: Statistical significance is indicated as * for P<0.05 and ** for P<0.01.
Figure 6B:
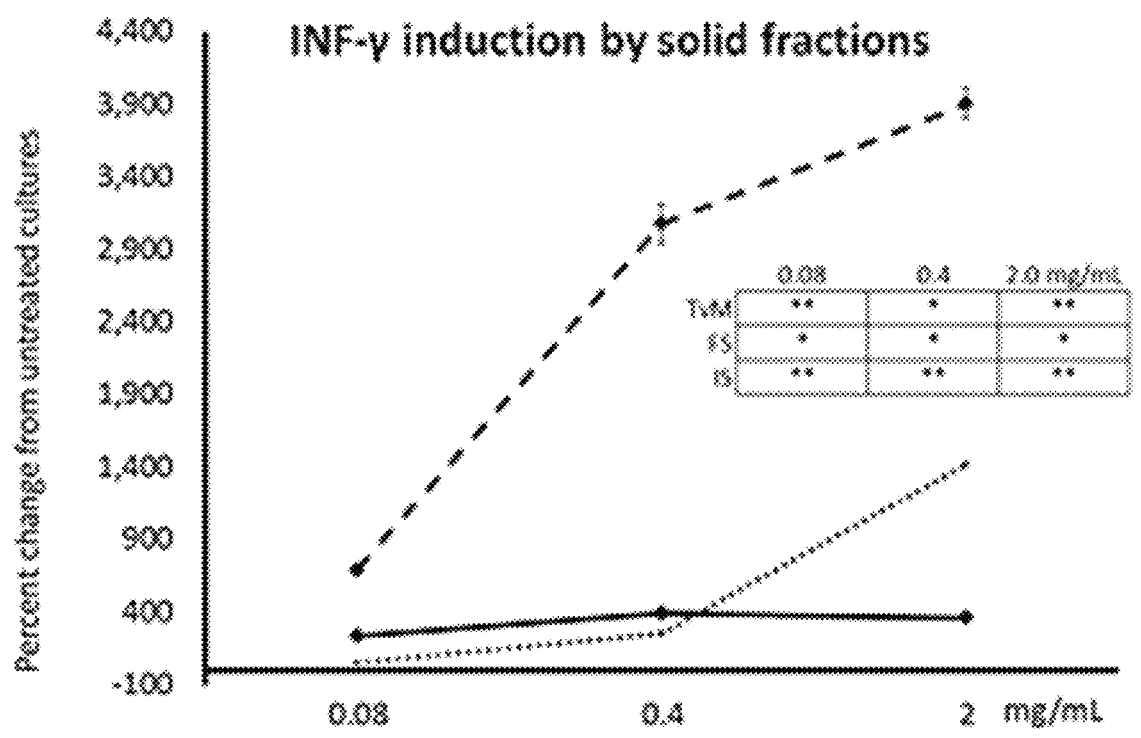
Figure 6C:
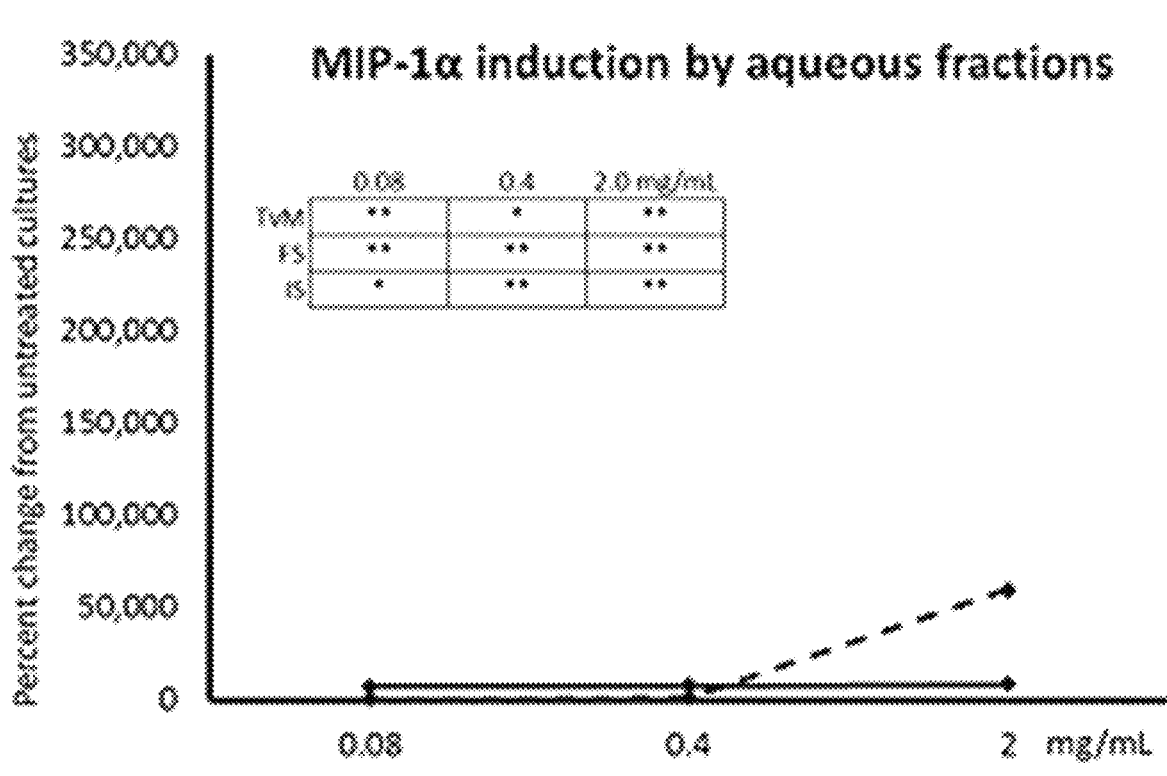
Figure 6D:
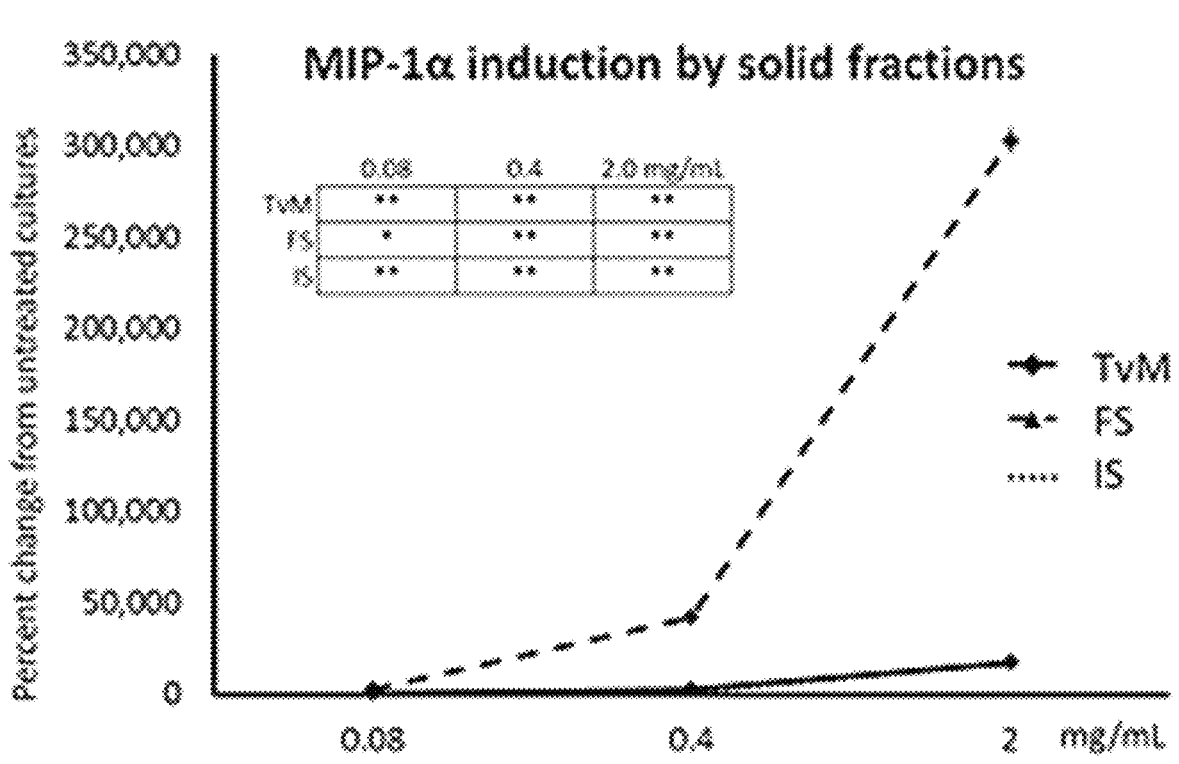

The treatment of human PBMC with the fungal extracts triggered increased production of two anti-viral cytokines, namely Interferon-gamma (IFN-γ) and MIP-1α (FIG. 6A-D). Representative results from one blood donor are shown in FIG. 6A-D. Both the aqueous and solid fractions from the fermented substrate triggered robust increases in these two cytokines, whereas treatment of cultures with the *Trametes versicolor* mycelium (TvM) led to modest increases in these cytokines. The aqueous fraction of TvM showed more potent effect on IFN-γ at lower doses than at higher doses (FIG. 6A). Treatment of human PBMC with the solid fraction of the initial substrate showed a minor increase in IFN-γ and MIP-1α production. The induction of IFN-γ exceeded that induced by the solid fraction of TvM (FIG. 6B). The MIP-1α induced by both aqueous and solid fractions of TvM and the initial substrate were similar in magnitude (FIG. 6C, D).

Increased Anti-Inflammatory Cytokine Production

Figure 7A:
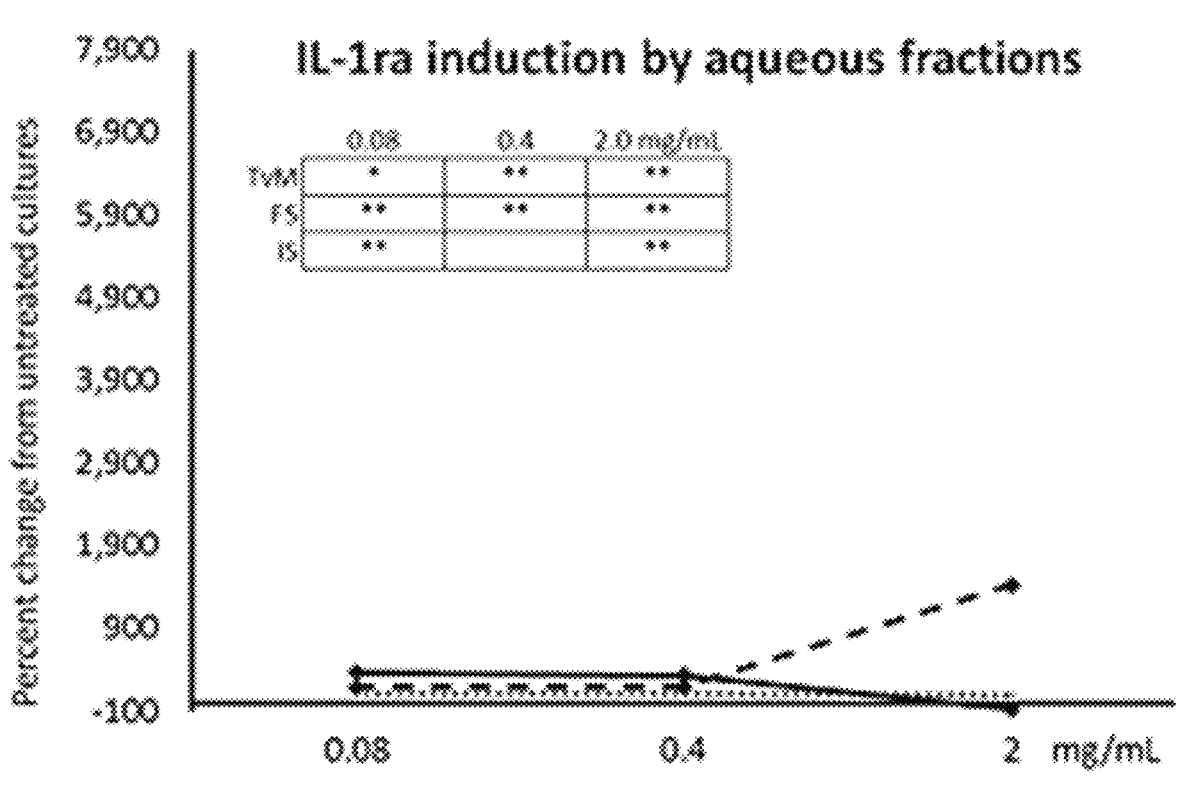
FIG. 7A-D show changes in levels of the cytokines Interleukin-1 receptor antagonist (IL-1ra) and Interleukin-10 in supernatants from human PBMC cultures. The PBMC were cultured for 24 h in the presence of serial dilutions of *Trametes versicolor* mycelium (TvM), fermented substrate (FS), or initial substrate (IS). The effects on IL-1ra and IL-10, both involved in anti-inflammatory processes as part of the resolution of inflammatory processes, of aqueous extracts are shown in FIG. 7A and FIG. 7C, and of the solid fractions are shown in FIG. 7B and FIG. 7D. Data are shown for three doses (0.08, 0.4, and 2 mg/mL), where the doses represent the amount of starting material used to produce a given fraction. Data are presented as mean±standard deviation of the percent change seen in triplicate cultures and represents one of three separate experiments using PBMC cells from three different healthy human donors. Inserted tables: Statistical significance is indicated as * for P<0.05 and ** for P<0.01.
Figure 7B:
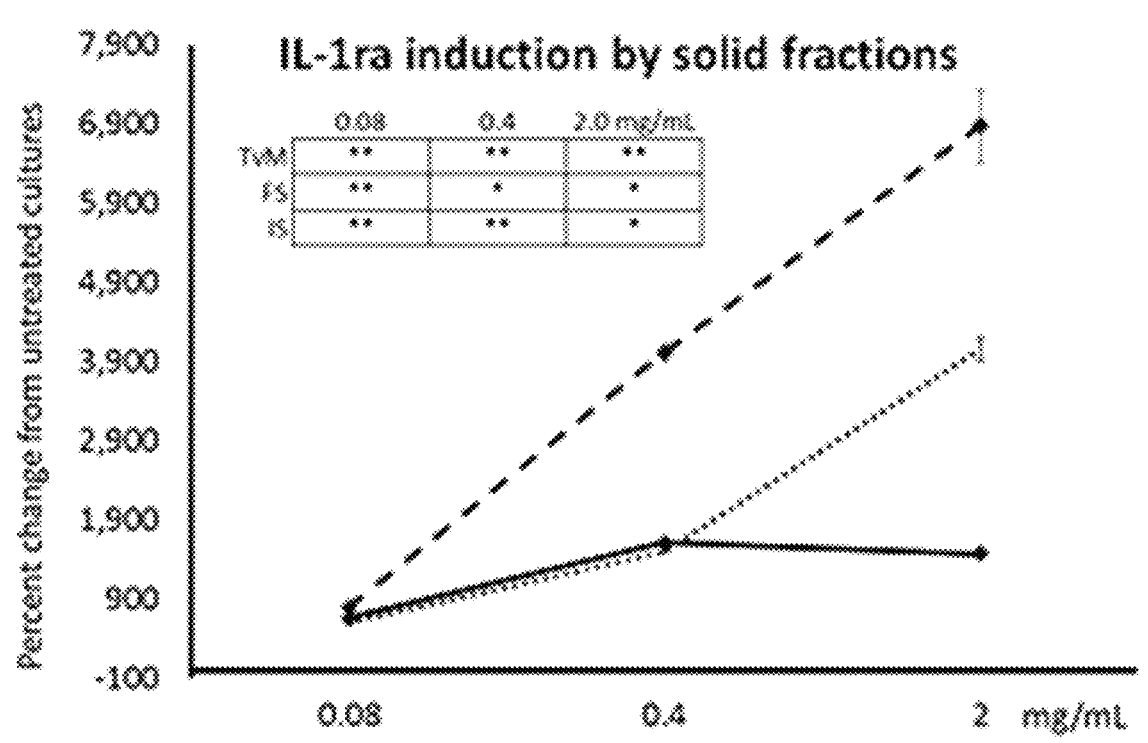
Figure 7C:
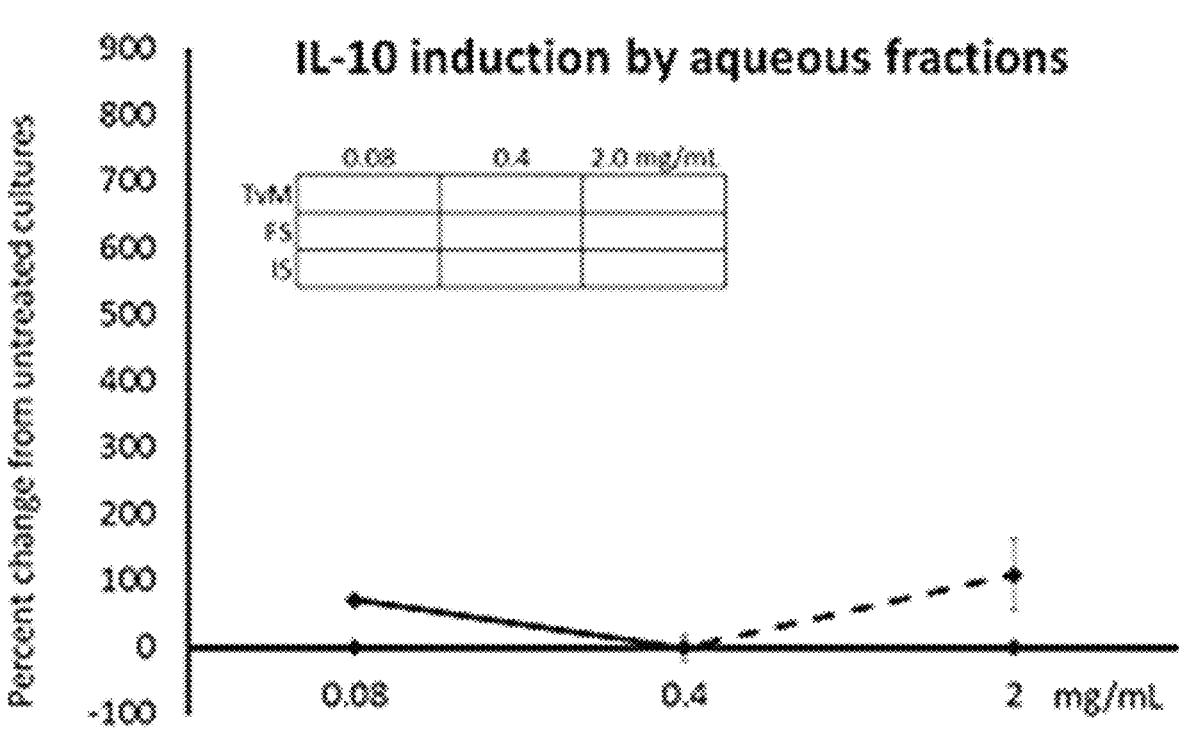
Figure 7D:
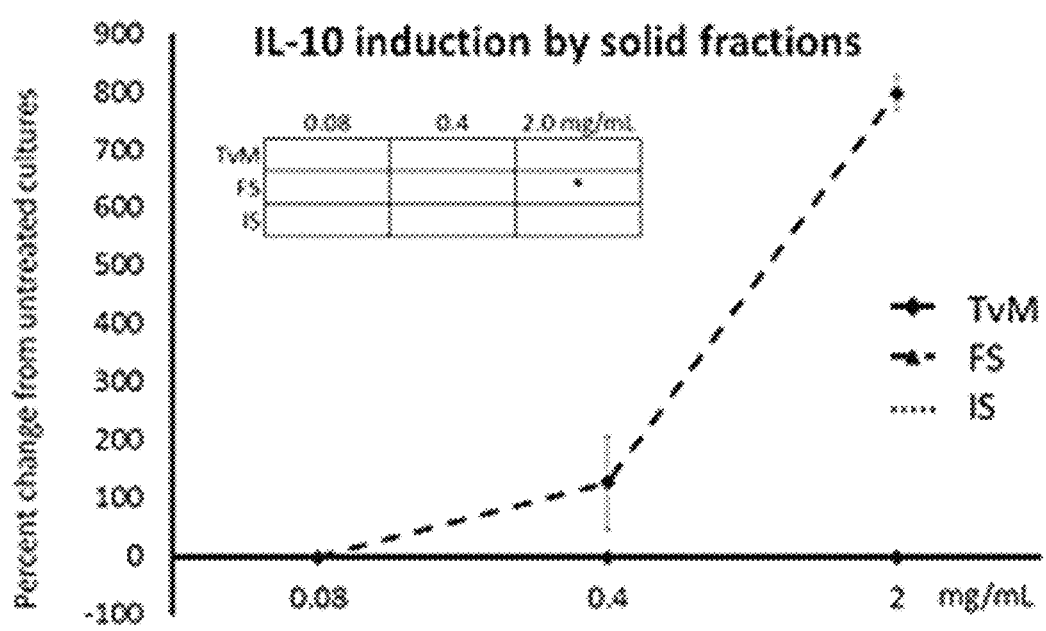

The treatment of human PBMC with the fungal extracts triggered increased production of two anti-inflammatory cytokines, namely Interleukin-1-Receptor Antagonist (IL-1ra) and Interleukin-10 (IL-10) (FIG. 7A-D). Representative results from one blood donor are shown in FIG. 7A-D. Both the aqueous and solid fractions from the fermented substrate triggered increases in both these two cytokines, with the most robust induction being associated with the solid fraction. The aqueous fraction of *Trametes versicolor* mycelium (TvM) showed more potent effect on both IL-1ra and IL-10 at lower doses than at higher doses (FIG. 7A, C). Interestingly, treatment of human PBMC with the solid fraction of the initial substrate showed a moderate increase in IL-1ra production, exceeding that induced by the solid fraction of TvM (FIG. 7B).

46

Increased Production of Markers Involved in Regenerative Processes

Figure 8A:
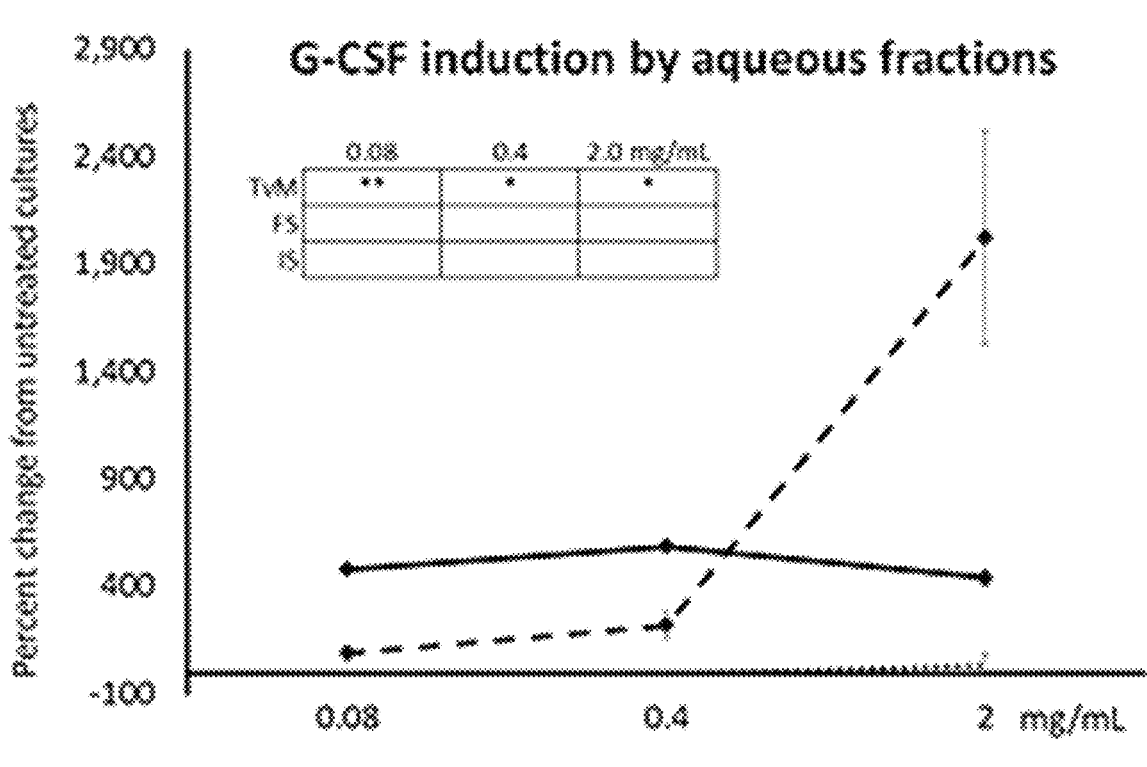
FIG. 8A-D show changes in levels of the growth factor Granulocyte-Colony Stimulating Factor (G-CSF) and the cytokine Interleukin-8 (IL-8) in supernatants from human PBMC cultures. The PBMC were cultured for 24 h in the presence of serial dilutions of *Trametes versicolor* mycelium (TvM), fermented substrate (FS), or initial substrate (IS). The effects on the stem cell mobilizing growth factor G-CSF and IL-8 of aqueous extracts are shown in FIG. 8A and FIG. 8C, and of the solid fractions are shown in FIG. 8B and FIG. 8D. Data are shown for three doses (0.08, 0.4, and 2 mg/mL), where the doses represent the amount of starting material used to produce a given fraction. Data are presented as mean±standard deviation of the percent change seen in triplicate cultures and represents one of three separate experiments using PBMC cells from three different healthy human donors. Inserted tables: Statistical significance is indicated as * for P<0.05 and ** for P<0.01.
Figure 8B:
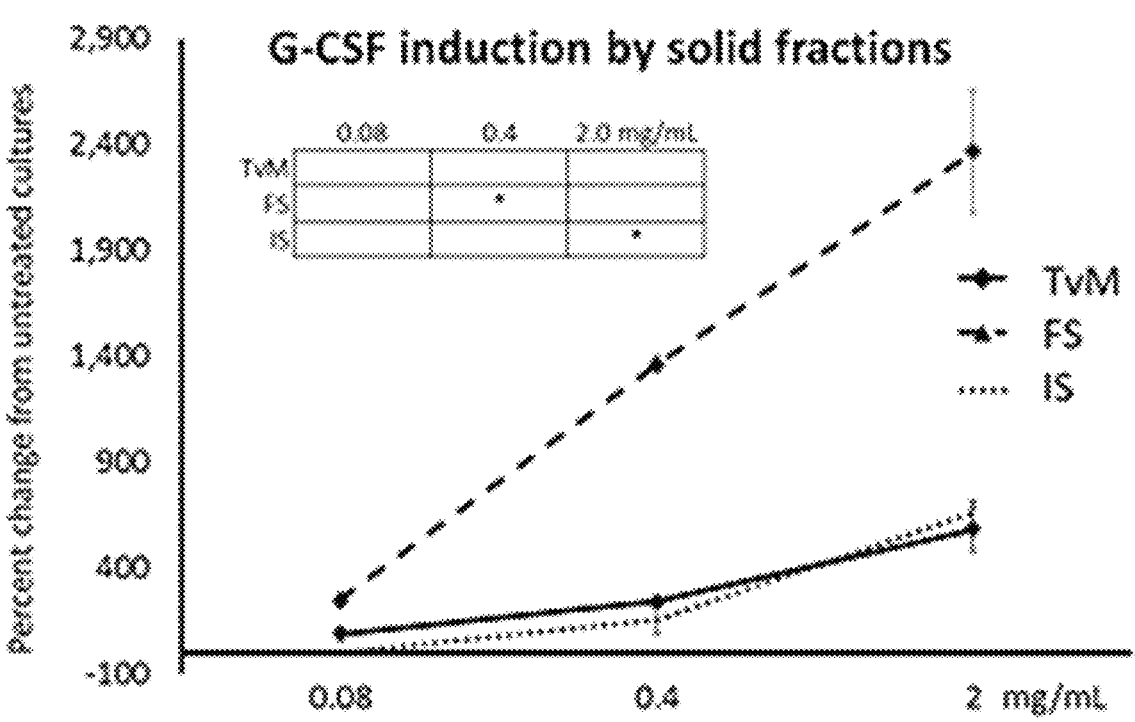
Figure 8C:
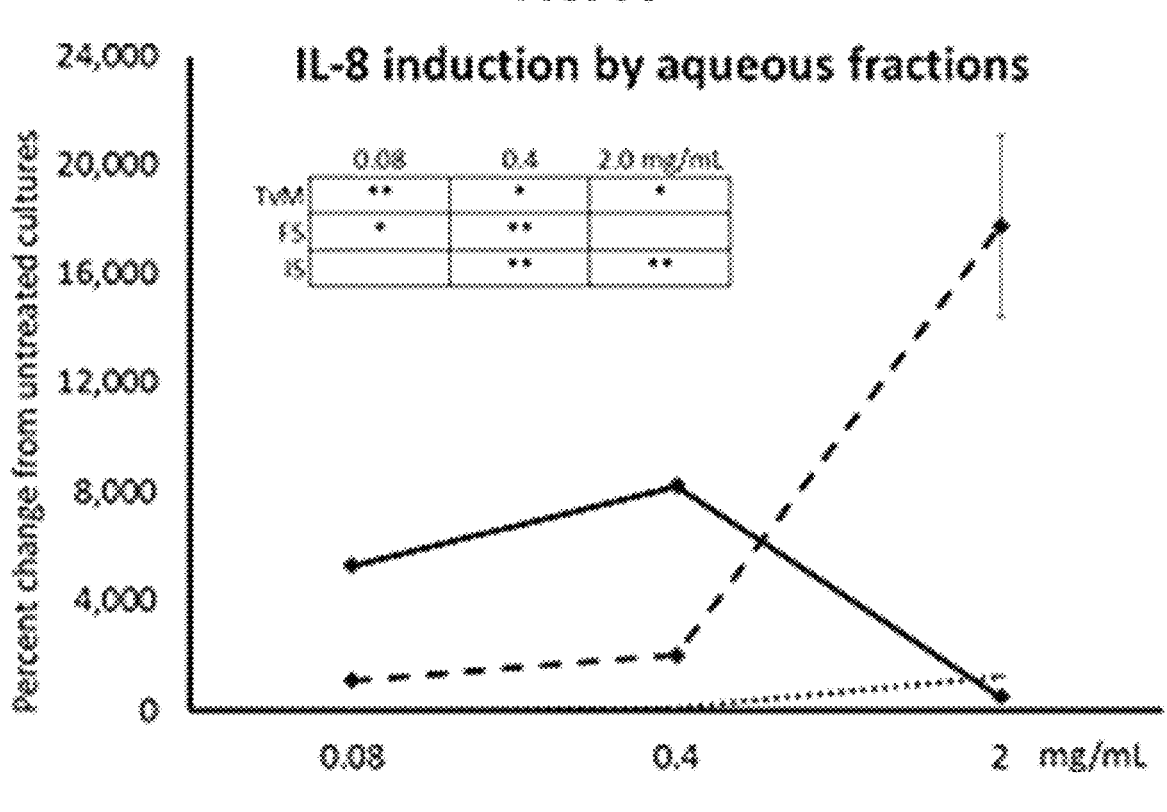
Figure 8D:
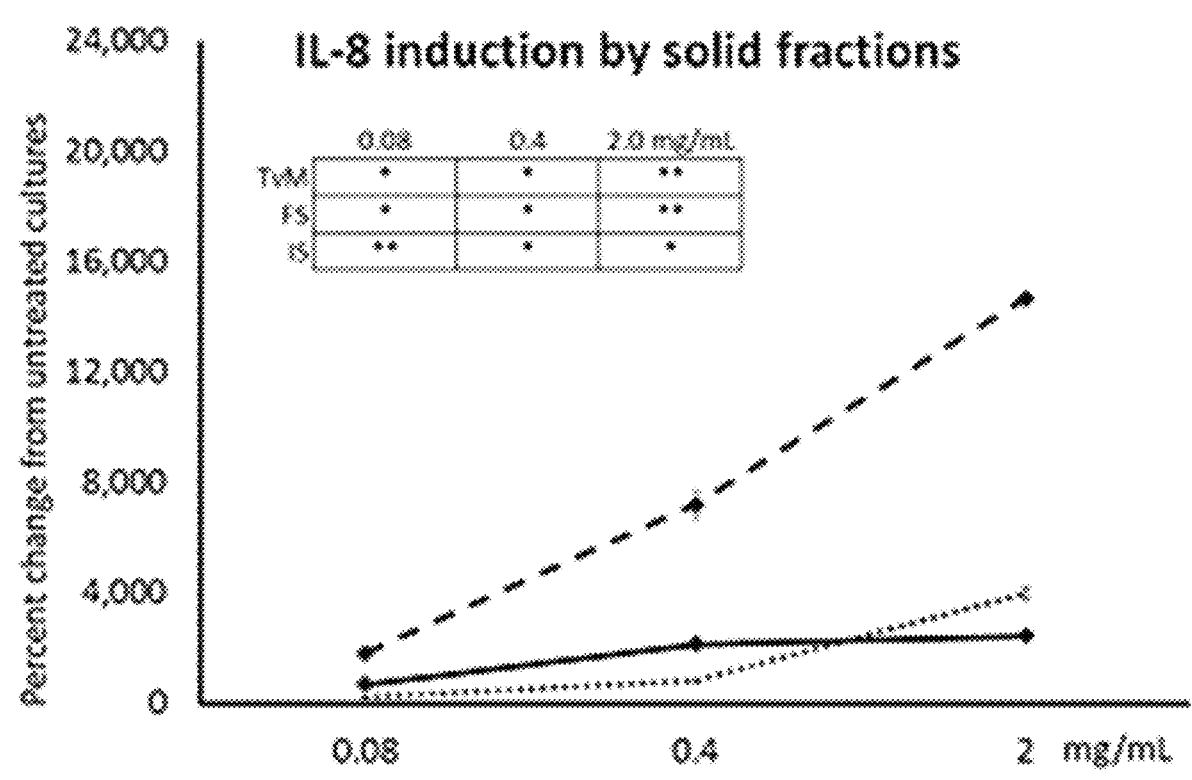

The treatment of human PBMC with the fungal extracts triggered increased production of two biomarkers involved in regenerative processes involving stem cells, Granulocyte Colony-Stimulating Factor (G-CSF) and Interleukin-8 (IL-8) (FIG. 8A-D). Representative results from one blood donor are shown in FIG. 8A-D. For the fermented substrate, both the aqueous and solid fractions triggered increases in both these two markers. The aqueous fraction of *Trametes versicolor* mycelium (TvM) showed effects at a broad dose range (FIG. 8A, C), whereas the effects of the solid fraction from the TvM showed similar effects as the solid fraction from the initial substrate (FIG. 8B, D).

The cytokine production results demonstrate that most of the bioactivity for cytokine induction lies in the fermented substrate. The fermented substrate likely represents a broad array of fungal products, in conjunction with breakdown products from the substrate.

The principal finding of the work reported here was a highly differentiated immune activating effect by the *Tram-* other medicinal mushrooms, and this model can help mycology research in the isolation and identification of bioactive compounds. There may be potentially pharmaceutical uses of isolated novel compounds from both mycelium and fermentate.

Example 3

The purpose of this study was to investigate the differential immunological effects of aqueous, ethanol, and solid fractions of MMB in vitro, to determine the differences in biological activity between the soluble and insoluble fractions of a complex medicinal mushroom blend (MMB), a blend of 17 mushroom species (Table 2). The study of a complex blend rather than isolated single compounds was of importance. The experimental model included effects on multiple immune cell types in vitro, because of parallels to events in the gut mucosal tissue where dendritic cells and macrophages sample antigens in the gut lumen, and present to lymphocytes in the gut-associated mucosal tissue, leading to local immune cell activation, and cytokine secretion that has systemic effects.

TABLE 2

Mushroom species in the medicinal mushroom blend

| Common name | Botanical name | Other names | Material | Primary medicinal use(s) |
|---|---|---|---|---|
| Royal Sun Blazei | *Agaricus blazei* | Himematsutake | M | Aox, IM |
| Cordyceps | *Cordyceps militaris* | | M | IM |
| Enokitake | *Flammulina velutipes* | | M | IM |
| Amadou | *Fomes fomentarius* | Tinder conk | M | IM |
| Agarikon | *Fomitopsis officinalis* | Lacriformes | M | Aox, IM |
| Artist Conk | *Ganoderma applanatum s.l.* | | M | IM, AI |
| Reishi | *Ganoderma lucidum s.l.* | Ling Zhi | M | Aox, AI, IM |
| Oregon Ganoderma | *Ganoderma oregonense s.l.* | | M | Aox, AI, IM |
| Maitake | *Grifola frondosa* | Hen of the woods | M/FB | IM |
| Lion's Mane | *Hericium erinaceus* | Yamabushitake | M | Neurological support |
| Chaga | *Inonotus obliquus* | | M | Aox, IM |
| Shiitake | *Lentinula edodes* | | M | IM |
| Mesima | *Phellinus linteus* | | M | Aox, IM |
| Birch Polypore | *Piptoporus betulinus* | | M | Aox, IM |
| Pearl Oyster | *Pleurotus ostreatus* | | M | IM |
| Split Gill Polypore | *Schizophyllum commune* | | M | IM |
| Turkey Tail | *Trametes versicolor* | | M | IM |

Abbreviations: M: Mycelium, FB: Fruiting body, IM: immunomodulator, Aox: Antioxidant, AI: anti-inflammatory, SC:stem cell modulator.

*etes versicolor* mycelium (TvM) when compared to its fermented substrate (FS). It was noteworthy that both aqueous and solid fractions of both materials had potent immune modulating activities. The results suggest that overall medicinal effects are associated both with the mycelium itself (including insoluble beta-glucans, but also water-soluble components), and the highly bioactive fermented substrate.

Interestingly, the initial un-fermented substrate was not very bioactive, devoid of aqueous bioactive compounds, and only minor effects on cytokine induction by the solid fraction. This further helps demonstrate the uniqueness of the fermented substrate, in terms of fermentation of the rice along with fungal exudates. This is important for the many consumable products that are produced from mycelia along with their fermented substrates.

Tv has proved to be an effective model for demonstrating the bioactivities of mycelium versus its fermented substrate. This model will be useful for further evaluation of Tv and Reagents Phosphate-buffered saline, Roswell Park Memorial Institute (RPMI) 1640 medium, penicillin-streptomycin 100×, interleukin-2 (IL-2), and lipopolysaccharide (LPS) from *Salmonella enterica* were purchased from Sigma-Aldrich Co. (St Louis, MO, USA). Lympholyte-Poly was obtained from Thermo-Fisher Scientific (Waltham MA, USA). CD69 fluorescein isothiocyanate, CD56 phycoerythrin, CD3 peridinin chlorophyll protein, and heparin Vacutainer tubes were purchased from Becton-Dickinson (Franklin Lakes, NJ, USA). Bio-Plex Pro™ human cytokine arrays were purchased from Bio-Rad Laboratories Inc. (Hercules, CA, USA).

Medicinal Mushroom Blend

The medicinal mushroom blend MyCommunity is sold internationally under the brand Host Defense® Mushrooms™ and was obtained from the manufacturer—Fungi Perfecti, LLC, Olympia, WA. It is a certified organic freeze-dried blend of 17 medicinal mushroom species (mycelium/ fruiting bodies) for immune system health: Royal sun blazei (*Agaricus brasiliensis* f. *blazei*), cordyceps (*Cordyceps militaris*), enokitake (*Flammulina velutipes*), amadou (*Fomes fomentarius*), agarikon (*Fomitopsis officinalis*), artist conk (*Ganoderma applanatum*), reishi (*Ganoderma lucidum* s.l.), Oregon ganoderma (*Ganoderma oregonense* s.l.), maitake (*Grifola frondosa*), lion's mane (*Hericium erinaceus*), chaga (*Inonotus obliquus*), shiitake (*Lentinula edodes*), mesima (*Phellinus linteus*), birch polypore (*Piptoporus betulinus*), pearl oyster (*Pleurotus ostreatus*), split gill polypore (*Schizophyllum commune*), and turkey tail (*Trametes versicolor*). See Table 2.

Testing for Endotoxins

The MMB powder was tested for endotoxin levels at Associates of Cape Cod Inc., East Falmouth MA, using the quantitative kinetic turbidimetric method for the detection of Gram-negative bacterial endotoxin, and reported in Endotoxin Units (EU).

Testing for Beta-Glucans

The whole MMB powder, as well as the freeze-dried solids of the aqueous and ethanol MMB fractions, were each tested for beta-glucan content by the Megazyme® assay at Venture Laboratories (Lexington, KY). This analysis involves total glucan hydrolysis by sulfuric acid and alpha-glucan hydrolysis by various enzymes. Total glucan and α-glucan content are measured spectrophotometrically, and β-glucans are estimated mathematically by the difference of these two values. All materials submitted for analysis were from the same lot number of material used in the immunological testing.

Preparation of Mushroom Fractions for Immune Bioassays

Figure 9:
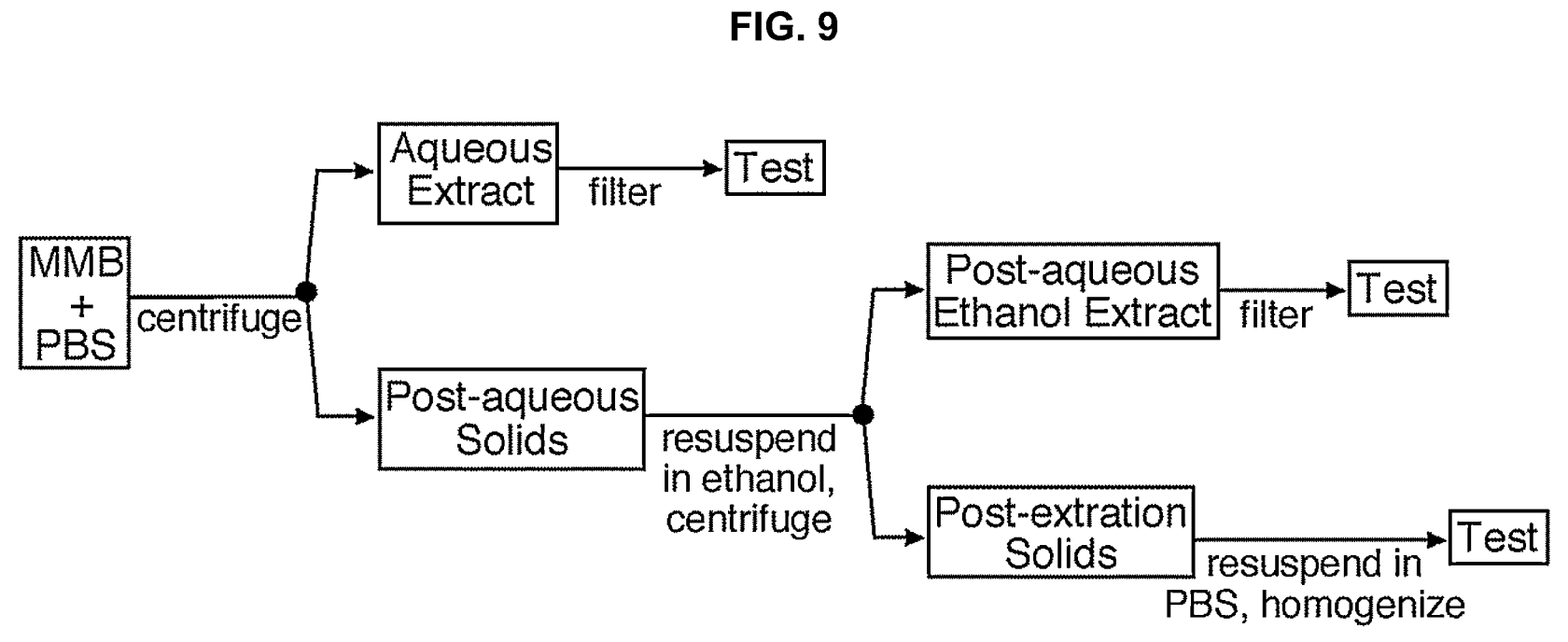

The powder was handled in the following manner, using pyrogen-free disposables: A 100 mg/mL suspension was prepared in phosphate-buffered saline (PBS) and allowed to rehydrate and extract aqueous compounds for 1 hour at 20° C. under gentle agitation. The suspension was centrifuged at 400 g for 10 minutes, and the aqueous fraction harvested. Ethanol (95%) was added to the pellet and vortexed, and extraction of non-aqueous, ethanol-soluble compounds allowed for 1 hour at 20° C. under gentle agitation. The suspension was centrifuged at 400 g for 10 minutes, and the ethanol fraction harvested. The remaining solid pellet was resuspended in PBS. The aqueous and ethanol fractions were filtered through a 0.22-micron syringe filter before adding to cell cultures. The solid fraction was passed through homogenization spin columns (QIAshredder, Qiagen, Hercules, CA), but were not filtered through a 0.22-micron filter. From each fraction, serial dilutions were made in pyrogen-free physiological saline. See also FIG. 9.

Immune Cell Activation

Peripheral venous blood was drawn from three healthy human donors upon written informed consent, as approval by the Sky Lakes Medical Center Institutional Review Board, Federalwide Assurance 2603. The blood was drawn into heparin vacutainer vials, and the peripheral blood mononuclear cells (PBMC) isolated using Lympholyte Poly by centrifugation for 35 minutes at 400×g. The PBMC were washed twice in PBS, counted, and the density adjusted to establish cultures with a cell density of 10⁶/mL, using Roswell Park Memorial Institute (RPMI) 1640 medium containing penicillin, streptomycin, and fetal bovine serum.

The highly inflammatory lipopolysaccharide (LPS) from *Salmonella enterica* was used as a positive control for immune-cell activation. Serial dilutions of products or LPS (10 ng/mL) were added to cultures at a volume of 20 μL, and cultures were then incubated at 37° C., 5% CO₂ for 24 hours. In parallel, IL-2 was used as a positive control for natural killer (NK)-cell activation, at a concentration of 100 IU/mL. Untreated negative control cultures consisted of PBMC exposed to phosphate-buffered saline in the absence of test products. All treatments, including each dose of test product and each positive and negative control, were tested in triplicate. After 24 hours, cells were transferred to V-bottom microtiter plates, washed in PBS containing bovine serum albumin and sodium azide, and stained for 10 minutes with fluorochrome-labeled anti-CD3, anti-CD56, and anti-CD69 monoclonal antibodies at the recommended concentration. PBMC were then fixed in formalin. The fluorescence intensities for CD3, CD56, and CD69 were measured by flow cytometry, using an Attune acoustic-focusing flow cytometer (Thermo Fisher Scientific, Waltham, MA, USA). Data analysis utilized gating on forward and side scatter to evaluate CD69 expression on lymphocyte versus monocyte/macrophage subsets. The lymphocyte subpopulation was further analyzed for CD69 expression on CD3–CD56+ NK cells, CD3+CD56+ NKT cells, CD3+CD56– T cells, and non-NK non-T lymphocytes.

Production of Cytokines, Chemokines, and Growth Factors

After 24 hours of incubation, after transfer to V-bottom microtiter plates and before cells were stained for flow cytometry analysis, the culture supernatants were harvested from the PBMC cultures described above. Levels of cytokines, chemokines, and growth factors were quantified using Bio-Plex protein arrays (Bio-Rad Laboratories Inc., Hercules CA, USA) and utilizing xMAP technology (Luminex, Austin, TX, USA).

Statistical Analysis

Data organization, exploration, and analysis were conducted using the statistical computing language R (version 3.5.2) implemented in the RStudio (version 1.0.143) software environment. Most data handling was conducted using the base package, with additional functions from the dplyr package (version 0.7.8) used in the reorganization of the raw data (Wickham, et al., A Grammar of Data Manipulation). Statistical analysis was implemented using the R 'stats' (version 3.5.2) and 'car' (version 3.0-2) packages (Fox and Weisberg, An {R} Companion to Applied Regression, 2$^{nd}$ ed.), as well as the packages 'vegan' (version 2.5-4), and 'vegan3d' (version 1.1-2) for multivariate ordination plots and Non-metric Multidimensional Scaling (NMDS) (Oksanen et al., Vegan: Community Ecology Package; Oksanen et al., vegan3d: Static and Dynamic 3D Plots for the 'vegan' Package. R package version 1.1-2 (2018). Multiple comparison test after Kruskal-Wallis used the 'pgirmess' package (version 1.6.9), and the 'RVAideMemoire' package (version 0.9-72) was used for pairwise permutational MANOVA with Bonferroni correction (Giraudoux, pgirmess: Spatial Analysis and Data Mining for Field Ecologists. R package version 1.6.9 (2018); Hervé, RVAideMemoire: Testing and Plotting Procedures for Biostatistics. R package version 0.9-72 (2019).

Example 4

Immune Activation

Figure 10A:
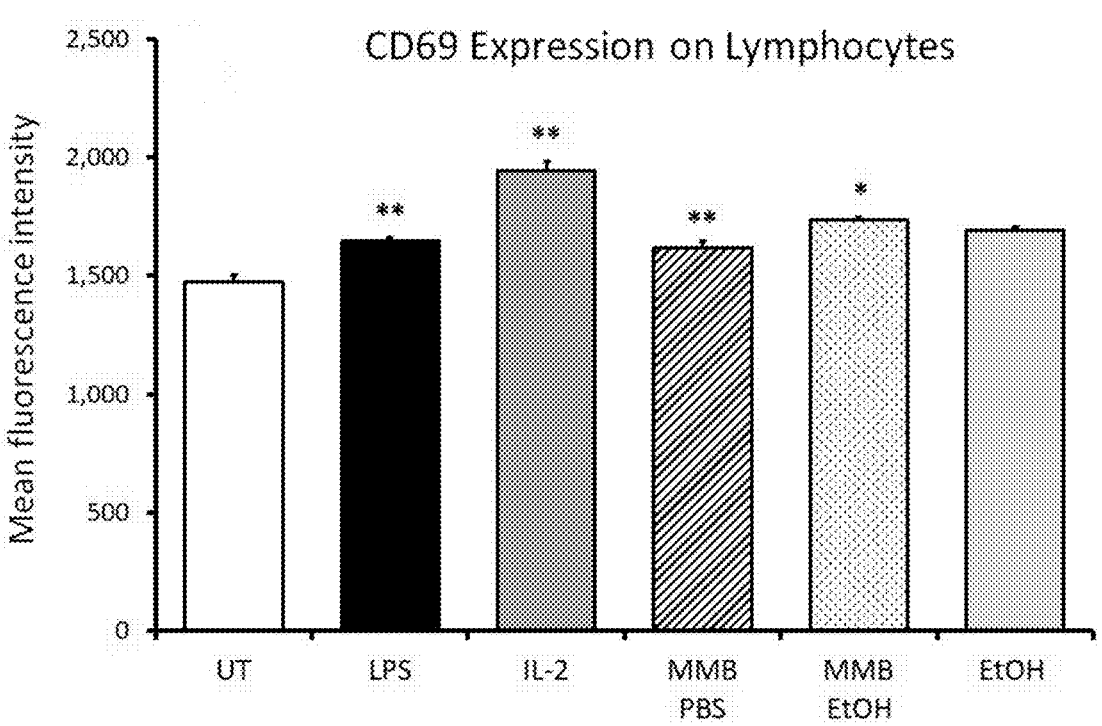
FIG. 10A and FIG. 10B show the expression of the early activation marker CD69 on lymphocytes and monocytes, *P<0.05; **P<0.01. CD69 expression on lymphocytes (FIG. 10A) and monocytes (FIG. 10B) in human PBMC cultures treated for 24 hours with serial dilutions of MMB aqueous extract in PBS (MMB PBS) and MMB ethanol extract (MMB EtOH). Results are shown for the 2 g/L dose. Mean fluorescence intensity for CD69 expression is shown. Data presented as mean±standard from triplicate cultures and represents data from PBMC cell cultures from one of the three different healthy human donors.
Figure 10B:
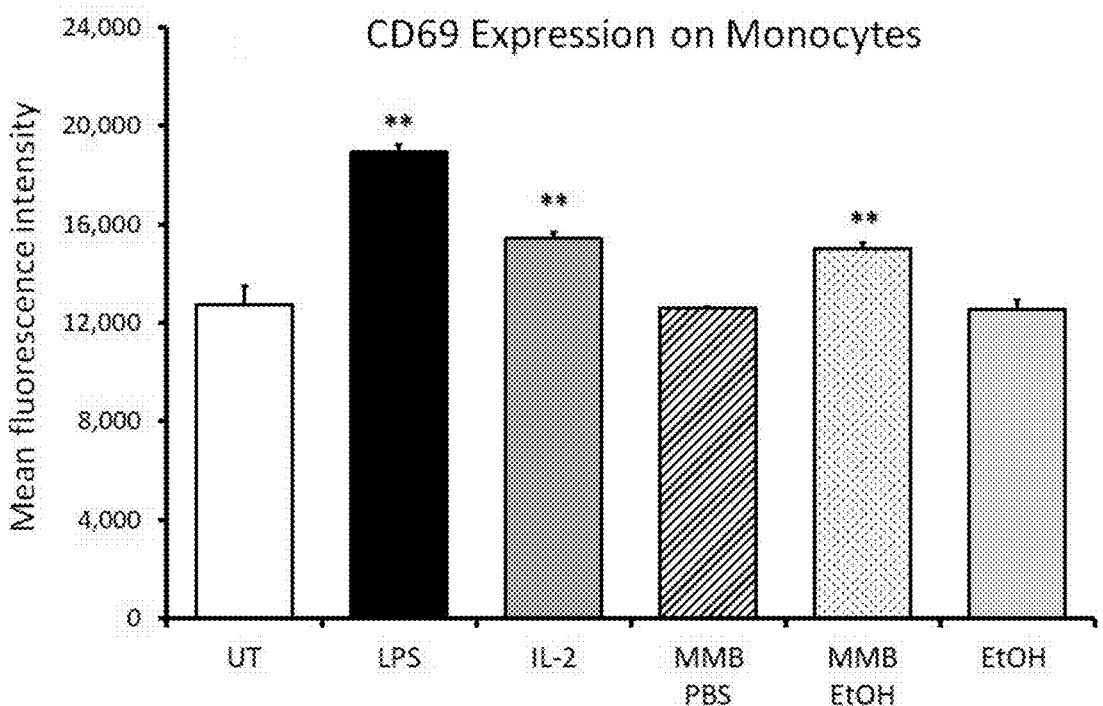

The aqueous and the ethanol fractions of the MMB blend were tested for immune cell activation in cultures of peripheral blood mononuclear cells (PBMC) from healthy donors (FIGS. 10-12). Whereas the aqueous fraction triggered upregulation of CD69 expression on lymphocytes (FIGS. 10A, 12A), the ethanol fraction triggered up-regulation of CD69 on monocytes (FIGS. 10B, 12B). Within the lymphocyte subset treated with the aqueous extract of MMB, only minor increases in CD69 expression were observed on NK cells

49

Figure 11A:
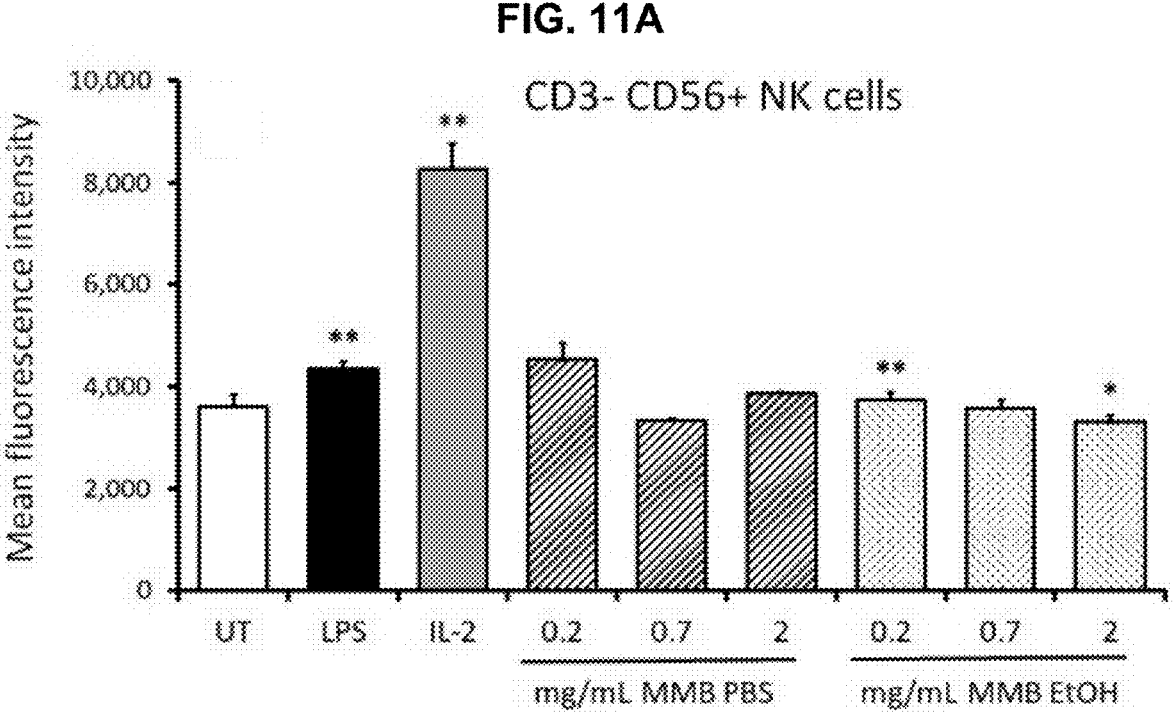
FIG. 11A-D show the expression of the early activation marker CD69 on lymphocyte sub-populations, *P<0.05; **P<0.01. CD69 expression on NK cells (FIG. 11A), NKT cells (FIG. 11B), non-NK non-T lymphocytes (FIG. 11C), and T cells (FIG. 11D) in human PBMC cultures treated for 24 hours with serial dilutions of MMB aqueous extract in PBS (MMB PBS) and MMB ethanol extract (MMB EtOH). Mean fluorescence intensity for CD69 expression is shown. Data presented as mean±standard deviation from triplicate cultures and represents one of three separate experiments using PBMC cells from three different healthy human donors.
Figure 11B:
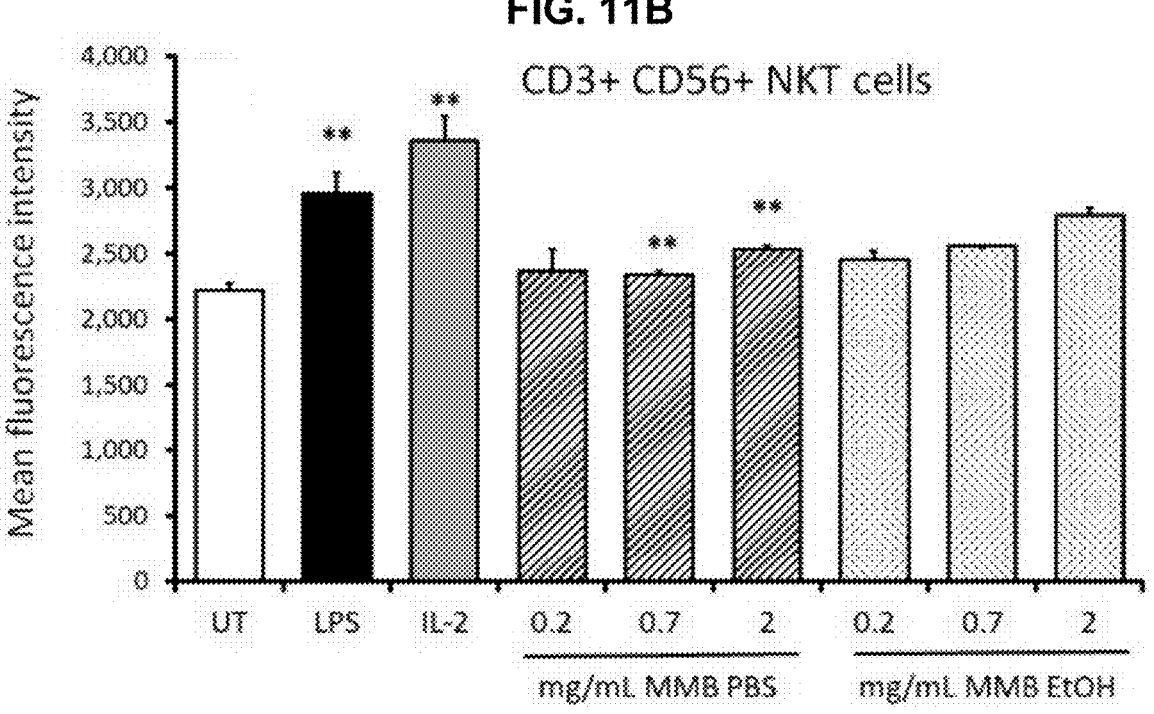
Figure 11C:
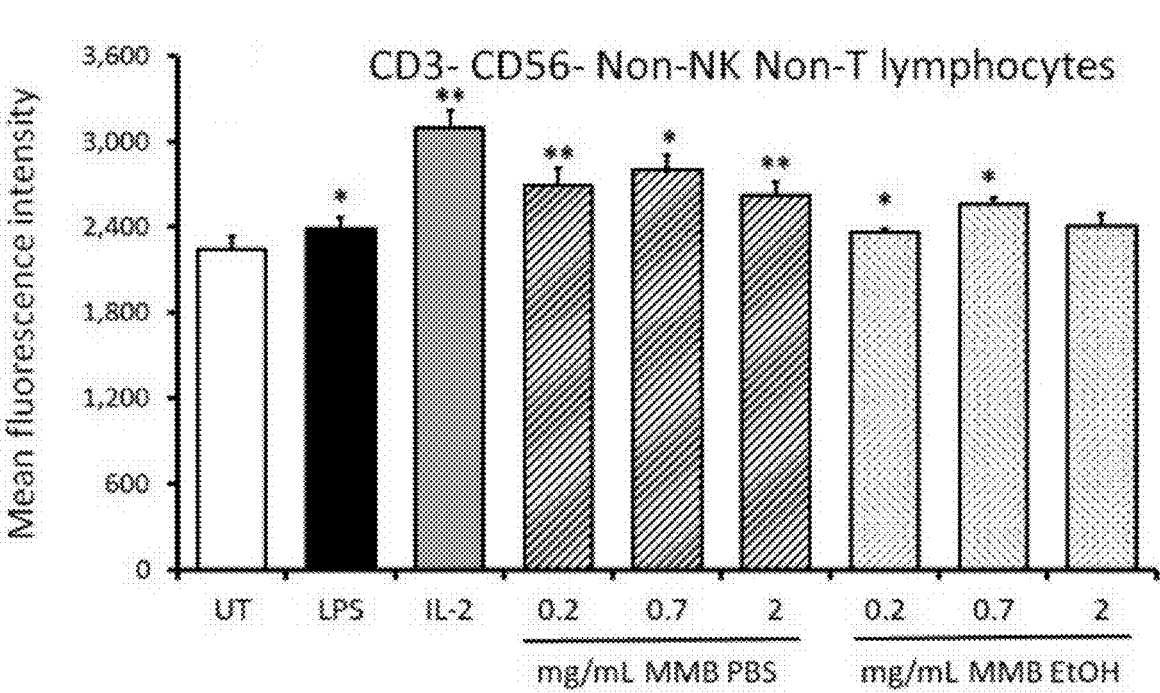
Figure 11D:
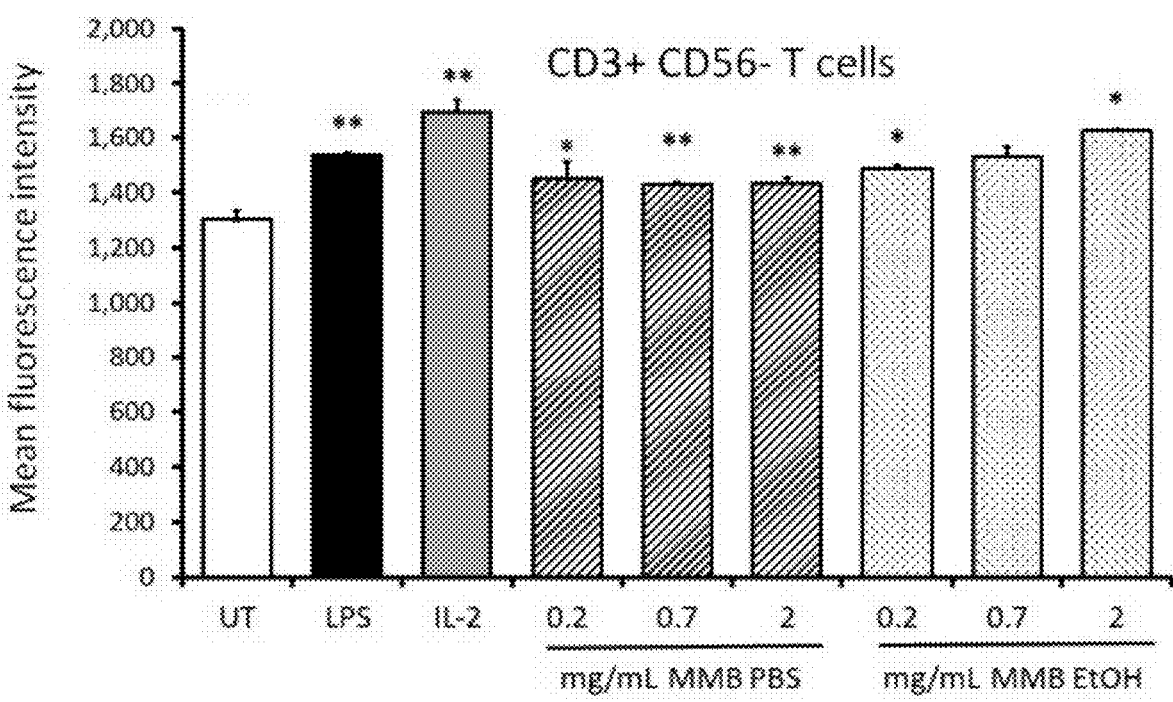
Figure 12A:
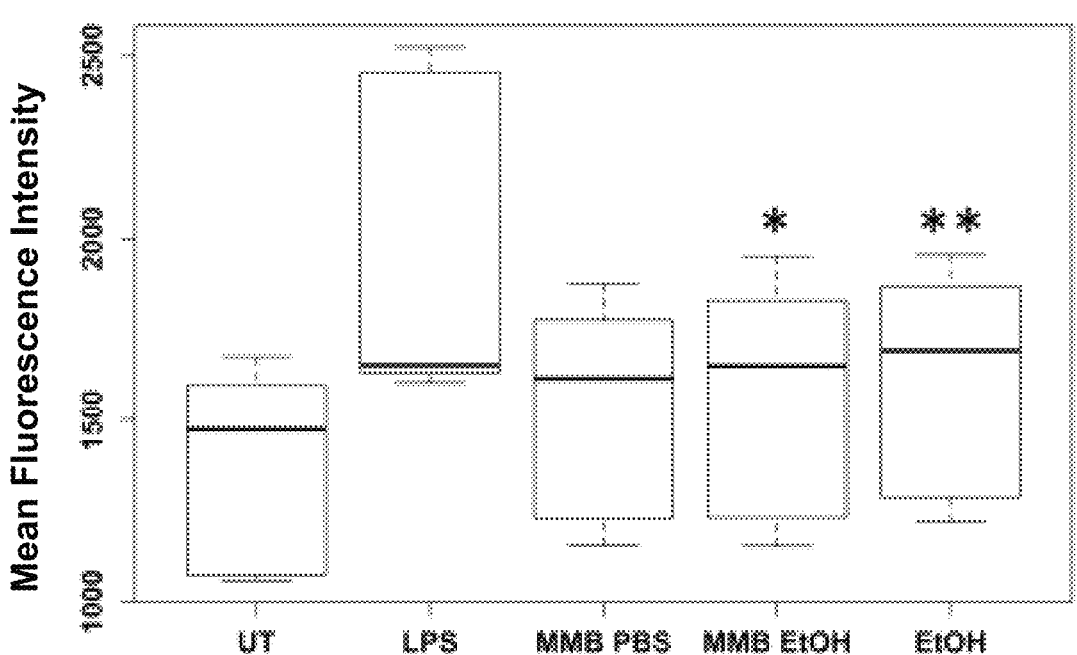
FIG. 12A-F show the expression levels of the CD69 early marker across white blood cell types, *P<0.05; P<0.01, *P<0.001. Mean fluorescence intensity resulting from immunostaining of the CD69 early activation marker, plotted with respect to cell type and treatment group for the two highest concentrations pooled across all donors. Fluorescence responses that followed a normal distribution (FIG. 12B, FIG. 12D, FIG. 12E) were statistically evaluated with ANOVA followed by a Tukey Honest Significant Difference post-hoc test. Non-normal fluorescence responses that could not be analyzed by ANOVA were evaluated using a Kurskal-Wallis Rank Sum Test followed by a multiple comparison post-hoc test with Bonferroni correction. Statistical significance is indicated as the difference between untreated cells and treatments with a family-wise error rate indicated by p<0.05 (*); p<0.01 (); p<0.001 (*).
Figure 12B:
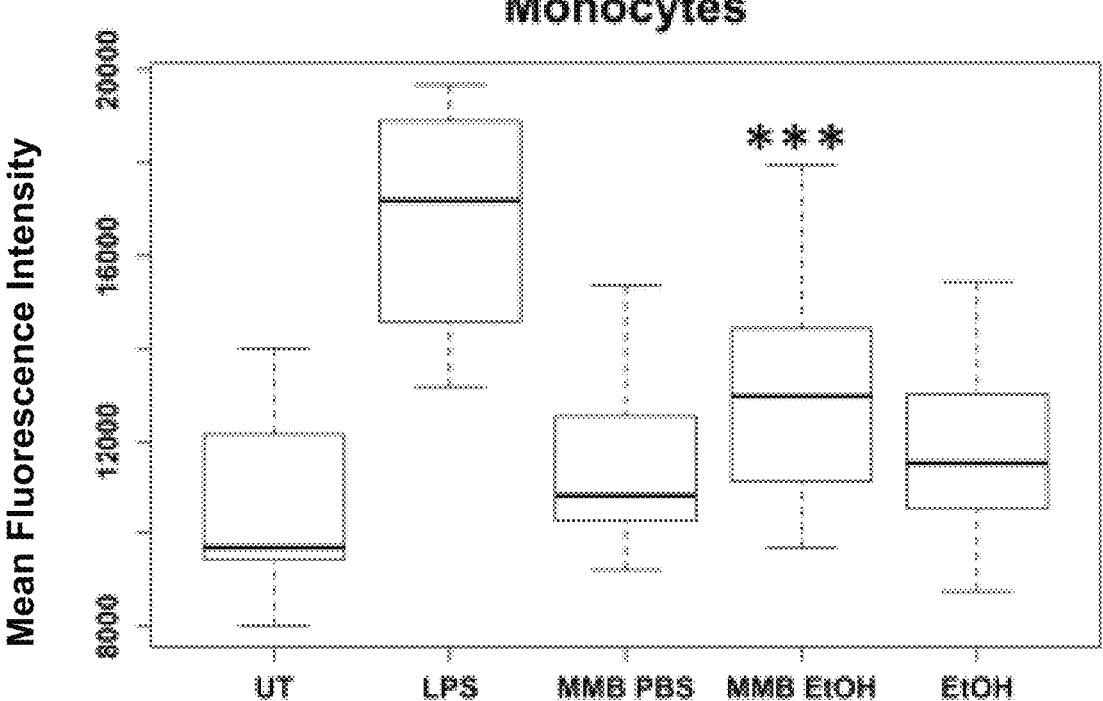
Figure 12C:
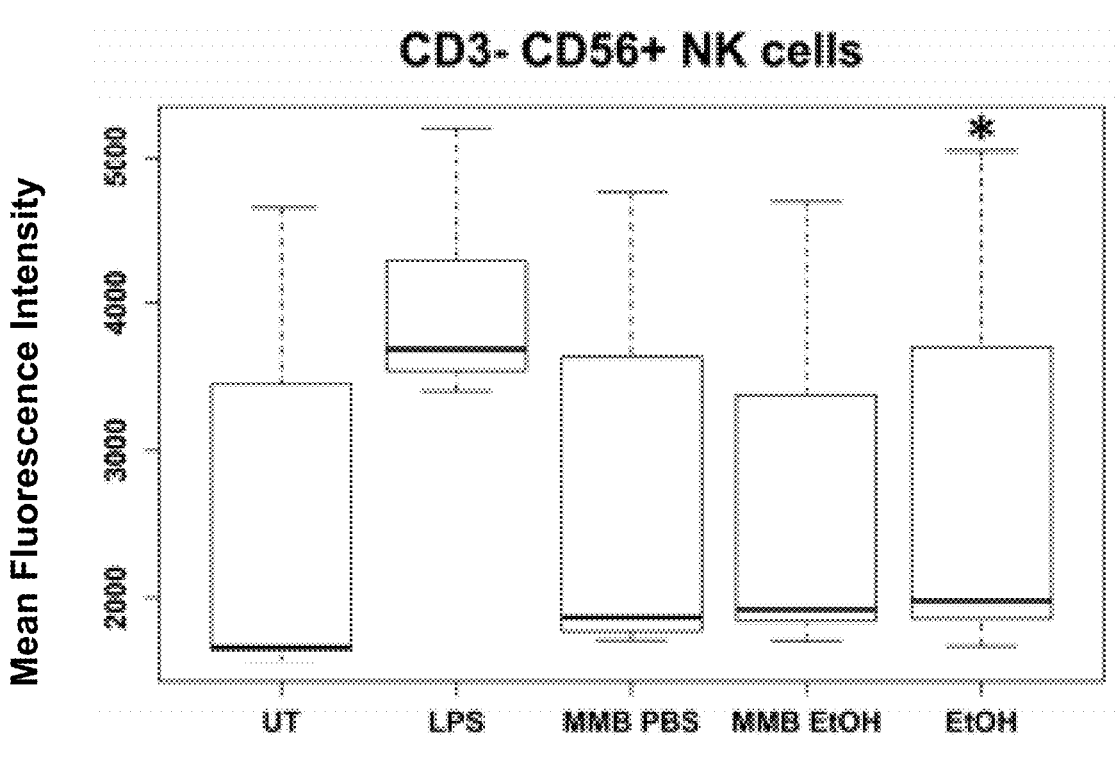
Figure 12D:
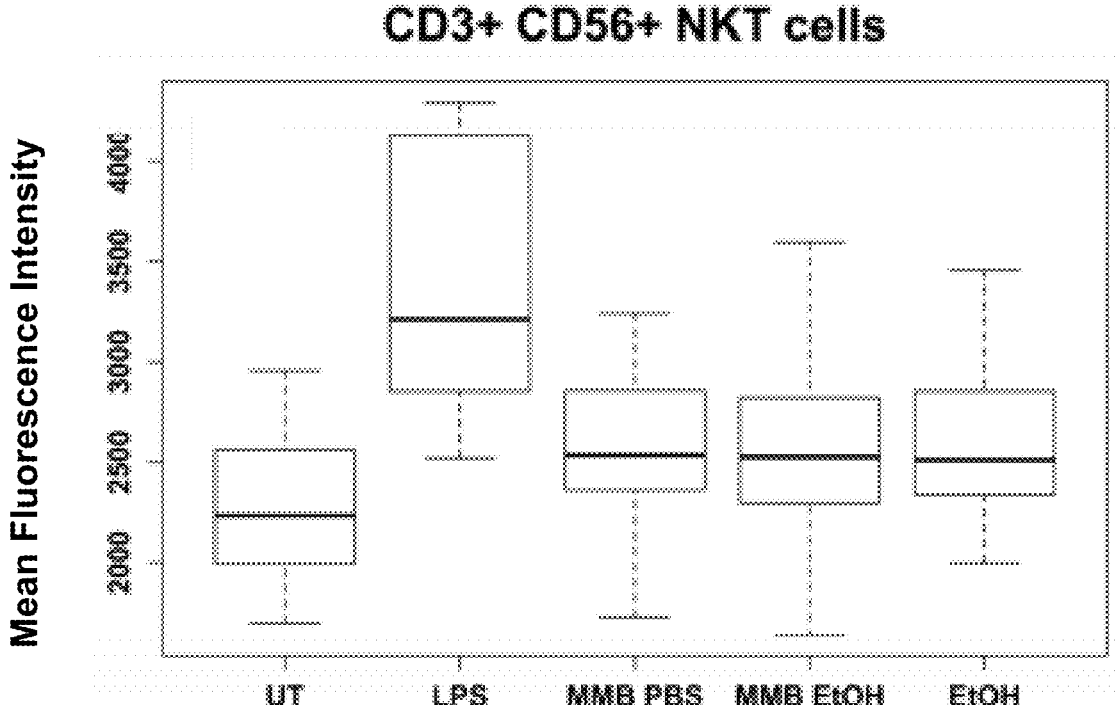
Figure 12E:
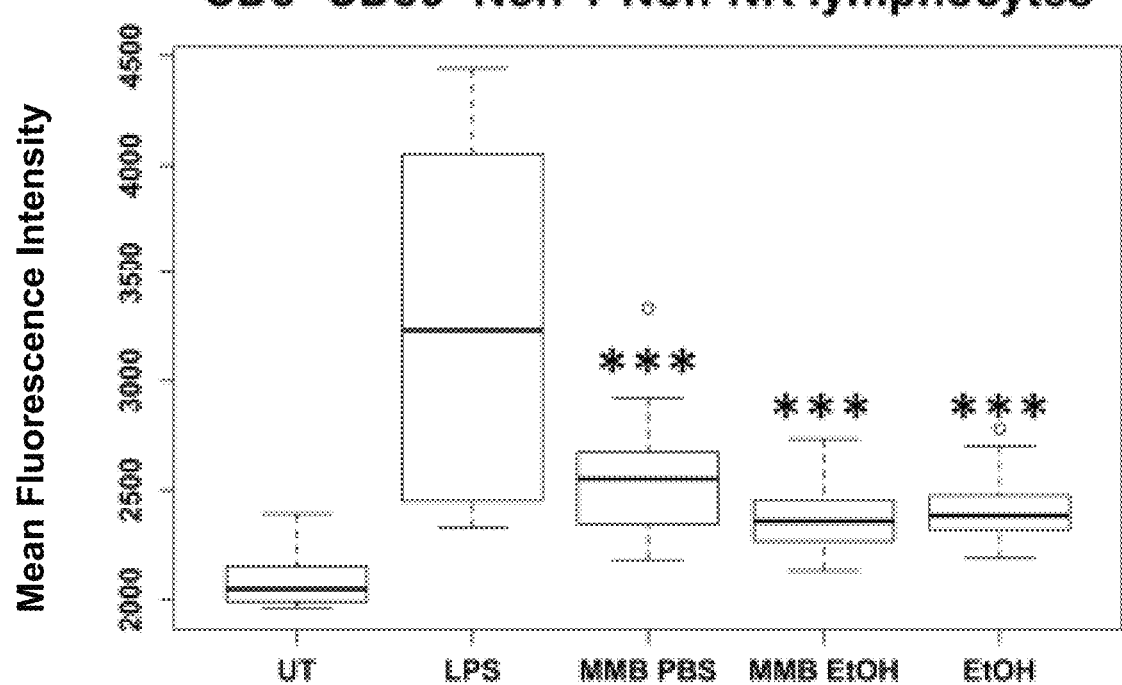
Figure 12F:
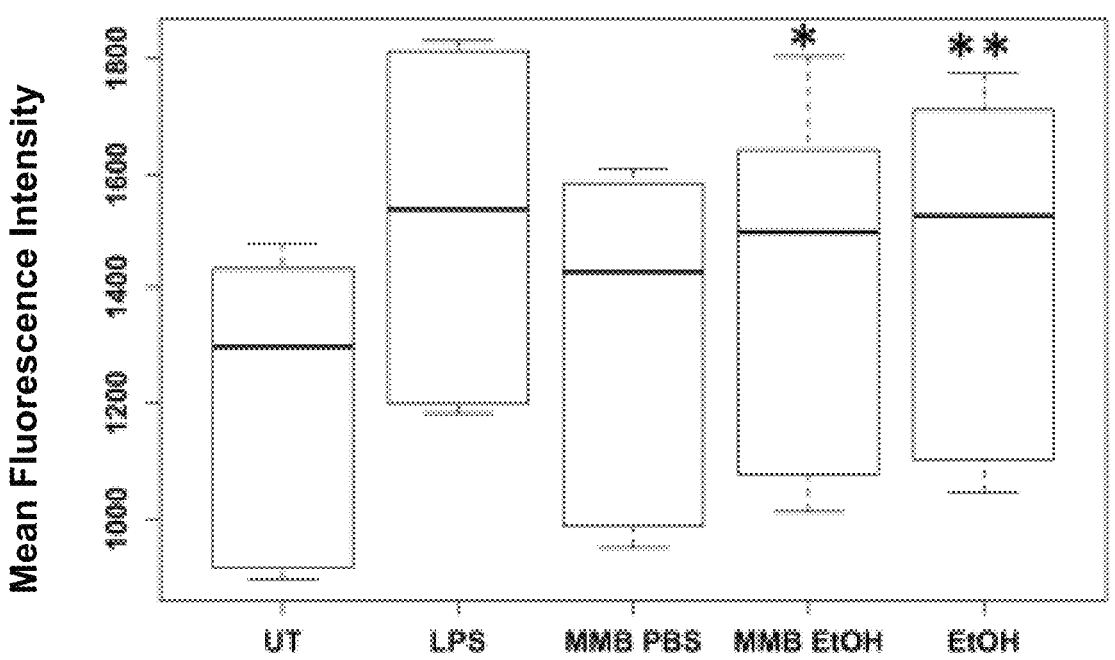

(FIGS. 11A, 12C), NKT (FIGS. 11B, 12D), and T cells (FIGS. 11D, 12F). The most robust increase in CD69 expression was seen for the CD3− CD56− non-NK non-T lymphocytes where the increase was statistically significant across all doses tested (FIG. 11C) and across all donors (FIG. 12E). This CD3− CD56− population contains dendritic cells and B lymphocytes, and stem cells, all which may express CD69.

The CD69 expression across all sub-populations of peripheral blood mononuclear cells were analyzed for the untreated cultures from all three donors and compared to CD69 expression in cultures treated with the two highest doses of MMB (2 mg/mL and 0.4 mg/mL). The analysis demonstrated the difference in induction of CD69 expression between the aqueous and the post-aqueous ethanol-based extracts (FIG. 12A-F). In these univariate box plots, the implicit statistical assumption is that the response of each cell type is independent of the response by each other cell type.

In addition to evaluation of cellular activation and CD69 expression on different cell types by standard univariate methodology, non-metric multidimensional scaling (NMDS)—a statistical technique borrowed from quantitative ecology—and permutational MANOVA were performed. This is based on the rationale that the PBMC cultures contain many cell types that interact and affect each other dynamically. These interactions affect the transcriptional landscape within each culture. This can be analyzed in the same way as ecologists study changes in flora and fauna abundance across diverse landscapes. The method was also applied to enable comparison of responses across the PBMC cultures from all three donors. In this analogy, each donor is like an ecological research site, each cytokine and growth factor is like a plant or animal type, and each MMB extract treatment is like a different type of land management practice (e.g. controlled burn forest vs. untended forest vs. open range forest). In the multivariate ordination plots, an assumption of independence among cell types (in the case of CD69 expression) or assumed statistical independence among co-induced cytokines is no longer necessary or appropriate. This is because the contemporaneously collected data is a snapshot of the aggregate PBMC response and it can be analyzed to account for covariance of responses among cell types or cytokines. The differences between the treatment groups is apparent when the covariance structure of the data set is represented using NMDS (FIG. 13).

Figure 13:
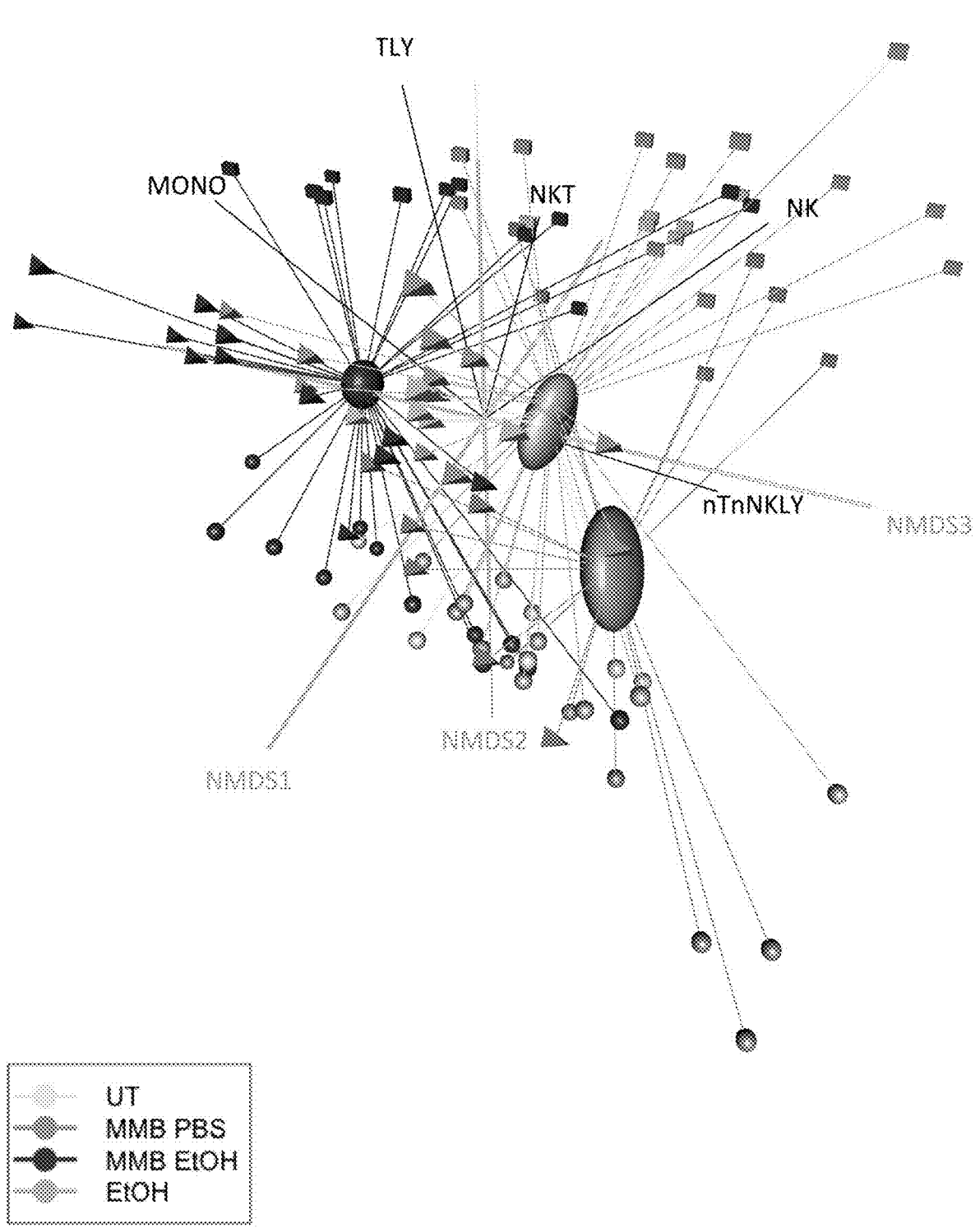
FIG. 13 shows the Non-metric Multi-dimensional Scaling (NMDS) ordination plot of CD69 expression by treatment and cell type. Ordination plot of NMDS site scores representing Bray-Curtis distance dissimilarities. The three-dimensions of the plot provide an excellent representation of the data in reduced dimensions (stress<0.05). The CD69 activation of each cell type is displayed as NMDS species vectors, with the vector direction and length indicating the strength of the correlation. Ovals represent the standard error of each treatment groups' data centroid within the multivariate data space.

In the NMDS ordination plot in FIG. 13, each dot represents the "Cartesian coordinate" location of each PBMC treatment well in a 5-dimensional data space (one dimension for each cell type), where the distance between points is proportional to the dissimilarity between each measurement. The dissimilarity between measurements was calculated using Bray-Curtis method to create a statistical distance matrix (Ricotta and Podani, *Ecological Complexity* 2017 31: 201-205). This 5-dimensional data space is then projected into a plot where each axis is an eigenvector of the distance matrix. An eigenvector is a transect through the data space that explains the greatest proportion of variance in the data. FIG. 13 is a 3-dimensional projection along the three eigenvectors (NMDS1, NMDS2, and NMDS3) that explain the greatest proportion of the variances. The overall "goodness of fit" statistic for this multivariate representation, known as stress, indicates that the projection in 3-dimensions provides an excellent representation of the underlying relationships (stress=0.043).

Permutational MANOVA and post-hoc pairwise comparisons with Bonferroni correction revealed that when considered collectively across cell types, the CD69 expression induced by MMB PBS was significantly different from the Untreated PBS (p<0.1), the MMB EtOH was different from the Untreated EtOH (p<0.05), and the MMB PBS extract was different from the MMB EtOH extract (p<0.05). Notably, the proportion of the variance in CD69 expression levels that can be explained by each treatment type was distinct for different white blood cell types (Table 3).

TABLE 3

Summary statistics for correlation between cell type and CD69 induction

| Cell type | $r^2$ | p-value | Ordinates toward |
|---|---|---|---|
| Monocyte | 0.73 | <0.001 | EtOH |
| Natural Killer | 0.47 | <0.001 | PBS/Untreated |
| Natural Killer T | 0.73 | <0.001 | EtOH |
| non-T non-NK Lymphocyte | 0.24 | <0.001 | PBS |
| T Lymphocyte | 0.88 | <0.001 | EtOH |

The NMDS ordination also confirmed the general trends identified in the univariate analysis: monocyte activation was strongly associated with the ethanol extract; non-T non-NK lymphocyte activation strongly correlated with the aqueous extract; and NKT cell, and T lymphocyte cell activation having a weaker but detectable activation by both the aqueous and ethanol extracts.

Immune Activating Cytokines

Figure 14A:
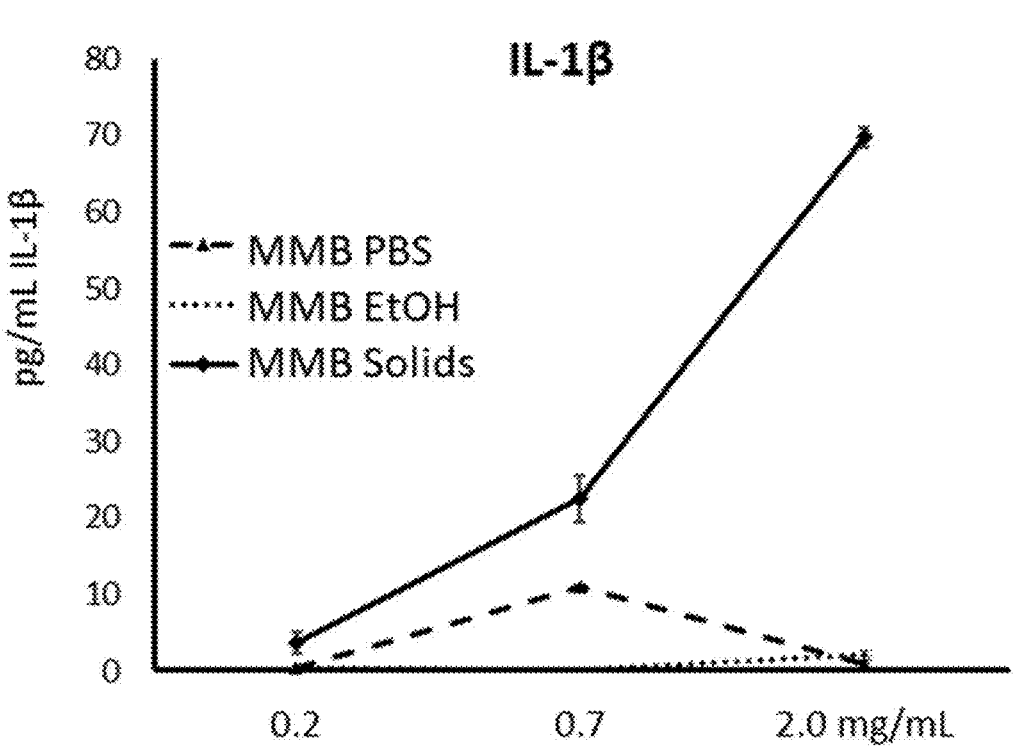
FIG. 14A and FIG. 14B show changes in immune-activating pro-inflammatory cytokine levels in human PBMC cultures. Changes in cytokine levels in human PBMC cultures treated for 24 hours with serial dilutions of MMB aqueous extract in PBS (MMB PBS), MMB post-aqueous ethanol extract (MMB EtOH), and the solid fraction (MMB solids). Data are presented as picogram per milliliter (pg/mL) based on the mean±standard deviation from triplicate cultures and represents one of three experiments using PBMC from three different healthy human donors. Cytokine levels for LPS-treated control cultures were as follows.
Figure 14B:
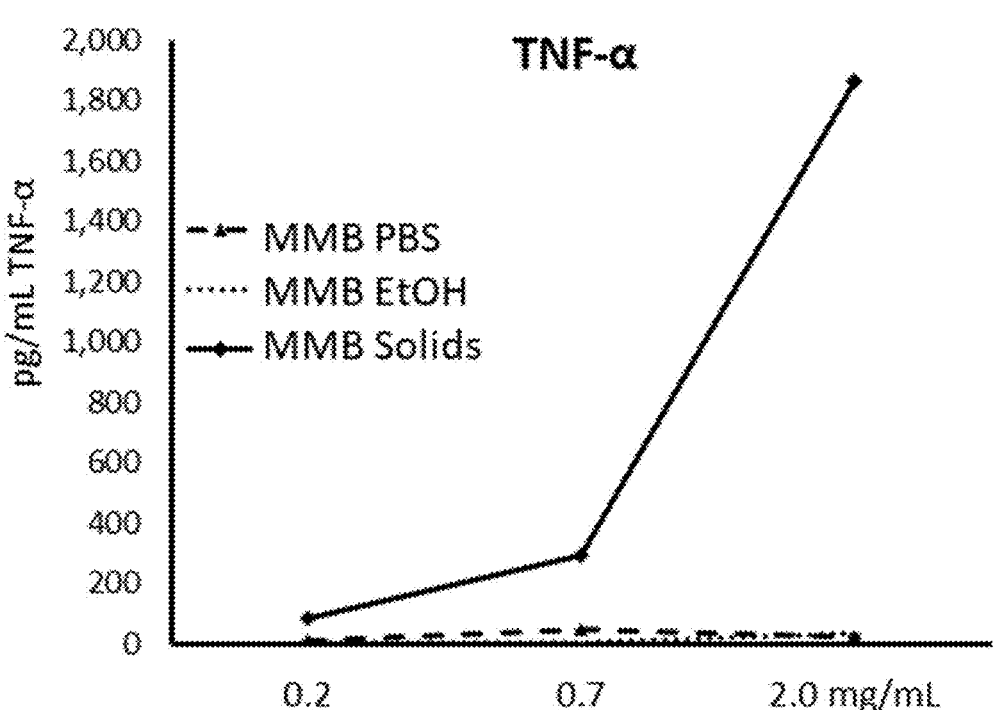

Supernatants from the PBMC cultures exposed to various doses of the MMB fractions for 24 hours were assayed for the levels of cytokines, chemokines, and growth factors, using a magnetic bead-based array and Luminex xMAP technology. Increases in the levels of immune activating cytokines included robust upregulation of specific pro-inflammatory cytokines, including IL-1β and TNF-α (FIG. 14A and FIG. 14B). The solid fraction of MMB (MMB solids) showed the most robust immune activating properties, but the aqueous extract (MMB PBS), free of insoluble β-glucans, also showed induction of immune activating cytokines. The post-aqueous ethanol extract (MMB EtOH) of the solids remaining after aqueous extraction showed only very minor effects on these cytokines.

Anti-Viral Cytokines

The MMB solid fraction triggered increases in the production of four specific cytokines and chemokines that are specifically associated with anti-viral activities and cellular recruitment (FIG. 15A-D). Interferon-γ (IFN-γ) was moderately induced by the MMB solid fraction (FIG. 15A). The monocyte chemoattractant protein-1 (MCP-1) and macrophage inflammatory proteins 1α and 1β were strongly increased by MMB solid fraction (FIG. 15 B, C, D). No changes to the biomarkers were apparent in the univariate analysis of the aqueous or post-aqueous ethanol extracts.

Anti-Inflammatory Cytokines

The MMB solid fraction was a very strong inducer of the anti-inflammatory cytokine IL-1ra (FIG. 16A), which functions as an IL-1 receptor antagonist, a strong anti-inflammatory protein due to its ability to prevent IL-1 in engaging in receptor binding and cellular signaling. To a much lesser extent, MMB solids triggered increased levels of IL-10 (FIG. 16B); however, this was not statistically significant in the multivariate data analysis. The aqueous fraction triggered a mild induction of both anti-inflammatory cytokines. The post-aqueous ethanol extract of MMB did not trigger changes to either cytokine.

Cytokines with Effects on Regenerative Functions

The effects of the MMB fractions on three cytokines with regenerative functions were clearly apparent in the univariate analysis of a representative donor, namely Granulocyte-Colony stimulating Factor (G-CSF), basic Fibroblast Growth Factor (bFGF), and Vascular Endothelial Growth Factor (VEGF) (FIG. 17A-C). Both the aqueous and the solid fractions induced increases in these three cytokines (FIG. 17A-C), with the MMB solid fraction showing the stronger effect.

Multivariate Analysis of Cytokine Activation

Because the levels of cytokines, chemokines, and growth factors were all quantified simultaneously using bead-based protein arrays, the meaning of expression levels of an individual analyte are more appropriately analyzed in the context of the other contemporaneously induced signaling molecules. Mathematically, this means the variance-covariance structure of the immune analytes must be considered. In the cytokine NMDS, the concentrations (pg/mL) of all 27 monitored cytokines and growth factors from the two highest MMB doses for all three fractions and including all three donors were analyzed simultaneously. The NMDS ordination visualization (FIG. 18) and summary statistics (Table 4) illustrate the strength of the solid fraction in inducing an immune response. Permutational MANOVA and post-hoc pairwise comparisons with Bonferroni correction revealed that when considered collectively across cytokines and growth factor expression, the MMB PBS was different from the Untreated PBS (p=0.02), and the MMB Solids were different from the Untreated PBS (p=0.02), the MMB PBS (p=0.02), and MMB EtOH (p=0.03). The net effect of the MMB EtOH on cytokines and growth factors was not significantly different from the Untreated PBS, the Untreated EtOH, or the MMB PBS.

regulating events after consumption. When a medicinal mushroom powder is ingested, it is assumed that aqueous compounds easily dissolve and are absorbed into the gastrointestinal mucosa. Compounds that are not water soluble either remain solids or get broken down by digestive enzymes and pH changes. The experimental post-aqueous ethanol fraction used for this project represents a method to test some compounds that may be released during the digestive process. The remaining solid fraction represents material that may get into direct contact with mucosal immune cells such as dendritic cells, known to extend trans-mucosal dendrites into the gut lumen, as well as absorption via transmucosal transport mechanisms to engage with tissue-residing gut mucosal immune cells.

The strong induction of IL-1β, TNF-α, and IFN-γ, in combination with induction of G-CSF, suggests that a cascade of events is triggered by exposure of cells to MMB fractions, potentially involving mesenchymal stem cells as a pivotal regulating cell type. Mesenchymal stem cells can cross the blood-brain barrier and contribute to repair of brain injuries such as stroke. Mesenchymal stem cells respond to inflammation in a manner that leads to events to counteract inflammation and promote homeostasis. When mesenchymal stem cells from healthy human donors were treated with the inflammatory cytokines IL-1, TNF-α, and IFN-γ, these cells responded with a strong increase in G-CSF production. Redondo-Castro et al., *Stem Cell Res Ther.* 8(1):79 (2017). This response was able to reprogram highly inflamed LPS-activated microglial cells to reduce the production of inflammatory mediators.

Endotoxin Testing

The level of endotoxin was 3.97 Endotoxin Units (EU)/mg MMB powder. Using the same assay, purified LPS results in 10 EU/ng, equivalent to 10,000,000 EU/mg puri-

TABLE 4

| Multivariate Redundancy Analysis: Summary Statistics by Cytokine and Growth Factor | | | |
|---|---|---|---|
| Cytokine/Growth Factor | Abbreviation | $r^2$ | p-value |
| Interferon-gamma | IFN-γ | 0.73 | <0.001 |
| Interleukin-1β | IL-1β | 0.64 | <0.001 |
| Interleukin-5 | IL-5 | 0.78 | <0.001 |
| Interleukin-6 | IL-6 | 0.68 | <0.001 |
| Interleukin-8 | IL-8 | 0.92 | <0.001 |
| Monocyte chemoattractant protein-1 | MCP-1 | 0.64 | <0.001 |
| Macrophage inflammatory protein-1α | MIP-1α | 0.95 | <0.001 |
| Macrophage inflammatory protein-1β | MIP-1β | 0.85 | <0.001 |
| Tumor Necrosis factor- a | TNF-α | 0.94 | <0.001 |
| Interleukin-1 receptor antagonist-a | IL-1ra | 0.76 | 0.002 |
| Interleukin-2 | IL-2 | 0.89 | <0.001 |
| Interleukin-4 | IL-4 | 0.82 | <0.001 |
| Interleukin-9 | IL-9 | 0.69 | <0.001 |
| Interleukin-15 | IL-15 | 0.79 | <0.001 |
| Basic Fibroblast Growth Factor | bFGF | 0.87 | <0.001 |
| Granulocyte-Colony Stimulating Factor | G-CSF | 0.93 | <0.001 |
| Chemokine (C-C motif) ligand 5 (CCL-5) | RANTES* | 0.33 | 0.014 |
| Vascular Endothelial Growth Factor | VEGF | 0.54 | <0.001 |

*RANTES: "regulated upon activation, normal T cell expressed and secreted"

The post-aqueous ethanol fraction showed a more selective immune regulating activity. It supported a stronger monocyte activation than the aqueous extract and comparable induction of IL-6, IL-9, and MIP-1β. This suggests that hydrophobic ethanol-soluble compounds in this fraction have immune activating and anti-viral properties, while also supporting selective aspects of regenerative functions related to IL-9.

This selective effect of the three MMB fractions is of interest when discussing the potential differential immune fied LPS. This 2.5 million-fold difference shows a much lower content of endotoxin in MMB compared to LPS and serves as a foundation upon which the immune activation data can be interpreted, since LPS was used as a positive control in the immune cell cultures. In several data sets below (FIG. 12C, FIG. 16A), the immune activating properties of MMB fractions exceeded that of a 10 ng/mL dose of LPS, suggesting that endotoxins in MMB would not be a major contributing factor to the induction of immune cell activation and cytokine production.

Beta-Glucan Testing

The whole MMB powder was tested for beta-glucan content by the Megazyme® assay and showed 38% (w/w) beta-glucan. The water and ethanol fractions used in the immune assays were measured by the same assay at 2.0% w/w and 1.1% w/w respectively. The solid fraction gave inconclusive results when tested in the Megazyme® assay, though it assumed that the difference between the whole MMB powder (38% beta-glucan) and the liquid extract beta-glucan yields the remaining insoluble beta-glucan in the solid fraction at approximately 35% w/w. Thus, the solid fraction contained 38% insoluble beta-glucans, while the aqueous and post-aqueous ethanol fractions contained small amounts of soluble beta-glucans accounting for very little content on a mass basis. The comparison showed that while the aqueous fraction was able to induce CD69 expression on lymphocytes, the post-aqueous ethanol fraction induced CD69 on monocytes, thus exhibiting complementary immune modulating activities. The solid fraction provided a highly robust effect on cytokine and growth factor production.

What is claimed is:

1. A method for treating, prophylaxis of, or ameliorating symptoms of an infectious disease in a subject in need thereof comprising:

administering to the subject a therapeutically effective amount of a composition comprising:

200-1,800 mg of an aqueous or solid fraction of *Trametes versicolor* mycelium, a fermented substrate thereof, or a combination thereof; and 200-1,800 mg of an aqueous or solid fraction of *Fomitopsis officinalis* mycelium, a fermented substrate thereof, or a combination thereof.

2. The method of claim 1, wherein the aqueous or solid fraction comprises beta-glucans.

3. The method of claim 1, wherein the composition further comprises one or more preservatives, flavorings, colorings, stabilizers, emulsifiers, or other pharmaceutically acceptable excipients.

4. The method of claim 1, wherein the infectious disease comprises one or more symptoms comprising shortness of breath, wheezing, coughing, yellow mucus, green mucus, blood-tinged mucus, chest pain, breathlessness, rapid breathing, hypoxia, inflammation of the lung tissue, rapid heart rate, or increased blood pressure, or decreased blood pressure.

5. The method of claim 1, wherein the infectious disease comprises a bacterial infection.

6. The method of claim 5, wherein the bacterial infection comprises one or more of *Streptococcus pneumoniae, Mycobacterium tuberculosis, Bordetella pertussis, Haemophilus influenzae, Moraxella catarrhalis, Pseudomonas aeruginosa, Stenotrophomonas maltophila, Staphylococcus aureus, Streptococcus pyogenes, Neisseria meningitidis, Klebsiella pneumoniae*, or Non-tuberculosis *Mycobacterium*.

7. The method of claim 1, wherein the infectious disease comprises a viral infection.

8. The method of claim 7, wherein the viral infection comprises one or more of Paramyxoviridae (respiratory syncytial virus (RSV), parainfluenza virus (PIV), metapneumovirus (MPV), enteroviruses), Picornaviridae (Rhinovirus, RV), Coronaviridae (CoV), Adenoviridae (Adenovirus), Parvoviridae (HBOV), Orthomyxoviridae (influenza A, B, C, D, Isavirus, Thogotovirus, Quaranjavirus), or Herpesviridae (human herpes viruses, *Varicella zoster* virus, Epstein-Barr virus, cytomegalovirus).

9. The method of claim 8, wherein the CoV comprises one or more of Severe Acute Respiratory Syndrome (SARS-CoV), Middle East Respiratory Syndrome (MERS-CoV), COVID-19 (2019-nCoV, SARS-CoV-2), 229E, NL63, OC43, or HKU1.

10. The method of claim 1, wherein the symptoms of an infectious disease comprise an inflammatory response associated with a bacterial or viral infection.

11. The method of claim 1, wherein the administration modulates one or more of cytokine storms, neuroinflammation, or blood clotting.

12. The method of claim 1, wherein a dose of the composition is administered to the subject 3 times per day.

13. The method of claim 1, wherein the composition is in the form of a capsule.

14. The method of claim 13, wherein the dose comprises at least 4 capsules.

15. The method of claim 1, wherein the composition is administered to the subject for about 10 to 30 consecutive days.

16. The method of claim 1, wherein the composition is administered to the subject for about 14 days.

17. The method of claim 1, wherein the subject has COPD, Cardiovascular disease, diabetes mellitus, hypertension, or a combination thereof.

18. The method of claim 1, wherein the subject is at least 60 years old.

19. The method of claim 1, wherein the composition is administered orally.

* * * * *